United States Patent
Frey et al.

(10) Patent No.: US 9,642,633 B2
(45) Date of Patent: *May 9, 2017

(54) PATIENT-MATCHED APPARATUS AND METHODS FOR PERFORMING SURGICAL PROCEDURES

(71) Applicant: MIGHTY OAK MEDICAL, INC., Englewood, CO (US)

(72) Inventors: George Frey, Englewood, CO (US); Paul Ginzburg, Centennnial, CO (US); Geoff Lai, Lakewood, CO (US); Caleb Voelkel, Lakewood, CO (US)

(73) Assignee: MIGHTY OAK MEDICAL, INC., Englewood, CO (US)

( * ) Notice: Subject to any disclaimer, the term of this patent is extended or adjusted under 35 U.S.C. 154(b) by 96 days.

This patent is subject to a terminal disclaimer.

(21) Appl. No.: 14/883,299

(22) Filed: Oct. 14, 2015

(65) Prior Publication Data

US 2016/0030067 A1 Feb. 4, 2016

Related U.S. Application Data

(63) Continuation-in-part of application No. 14/298,634, filed on Jun. 6, 2014, now Pat. No. 9,198,678, which
(Continued)

(51) Int. Cl.
*A61B 17/58* (2006.01)
*A61B 17/17* (2006.01)
(Continued)

(52) U.S. Cl.
CPC .......... *A61B 17/1757* (2013.01); *A61B 17/15* (2013.01); *A61B 17/151* (2013.01);
(Continued)

(58) Field of Classification Search
CPC ..... A61B 17/1757; A61B 50/33; A61B 34/10; A61B 17/8863; A61B 17/15;
(Continued)

(56) References Cited

U.S. PATENT DOCUMENTS 3,151,392 A 10/1964 Chambers
5,201,734 A 4/1993 Cozad et al.
(Continued)

FOREIGN PATENT DOCUMENTS

CN 201275138 7/2009
CN 201404283 2/2010
(Continued)

OTHER PUBLICATIONS

Extended Search Report for European Patent Application No. 13778164.7, dated Feb. 17, 2016 10 pages.
(Continued)

*Primary Examiner* — Sanjay Cattungal
(74) *Attorney, Agent, or Firm* — Sheridan Ross P.C.

(57) ABSTRACT

A system and method for developing customized apparatus for use in one or more surgical procedures is disclosed. The system and method incorporates a patient's unique anatomical features or morphology, which may be derived from capturing MRI data or CT data, to fabricate at least one custom apparatus. According to a preferred embodiment, the customized apparatus comprises a plurality of complementary surfaces based on a plurality of data points from the MRI or CT data. Thus, each apparatus may be matched in duplicate and oriented around the patient's own anatomy, and may further provide any desired axial alignments or insertional trajectories. In an alternate embodiment, the apparatus may further be aligned and/or matched with at least one other apparatus used during the surgical procedure.

22 Claims, 60 Drawing Sheets

Related U.S. Application Data is a continuation-in-part of application No. 13/841,069, filed on Mar. 15, 2013, now Pat. No. 8,870,889, which is a continuation-in-part of application No. 13/172,683, filed on Jun. 29, 2011, now Pat. No. 8,758,357.

(60) Provisional application No. 62/162,466, filed on May 15, 2015, provisional application No. 61/832,583, filed on Jun. 7, 2013, provisional application No. 61/845,463, filed on Jul. 12, 2013, provisional application No. 61/877,837, filed on Sep. 13, 2013, provisional application No. 61/359,710, filed on Jun. 29, 2010, provisional application No. 61/393,695, filed on Oct. 15, 2010, provisional application No. 61/625,559, filed on Apr. 17, 2012.

(51) Int. Cl.
| | | |
|---|---|---|
| *A61B 17/70* | (2006.01) | |
| *A61B 17/15* | (2006.01) | |
| *A61B 17/88* | (2006.01) | |
| *G09B 23/30* | (2006.01) | |
| *A61B 50/33* | (2016.01) | |
| *A61B 34/10* | (2016.01) | |
| *A61B 17/56* | (2006.01) | |
| *A61F 2/30* | (2006.01) | |
| *A61F 2/44* | (2006.01) | |
| *A61F 2/46* | (2006.01) | |
| *A61B 17/00* | (2006.01) | |
| *A61B 90/00* | (2016.01) | |
| *A61B 50/30* | (2016.01) | |

(52) U.S. Cl.
CPC ...... *A61B 17/7074* (2013.01); *A61B 17/8863* (2013.01); *A61B 34/10* (2016.02); *A61B 50/33* (2016.02); *G09B 23/30* (2013.01); *A61B 2017/00526* (2013.01); *A61B 2017/568* (2013.01); *A61B 2034/107* (2016.02); *A61B 2034/108* (2016.02); *A61B 2050/3008* (2016.02); *A61B 2090/061* (2016.02); *A61B 2090/067* (2016.02); *A61F 2/30965* (2013.01); *A61F 2/4405* (2013.01); *A61F 2002/3095* (2013.01); *A61F 2002/30952* (2013.01); *A61F 2002/4687* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01)

(58) Field of Classification Search
CPC .............. A61B 17/151; A61B 17/7074; A61B 2090/061; A61B 2034/107; A61B 2090/067; A61B 2034/108; A61B 2050/3008; A61B 2017/00526; A61B 2017/568; G09B 23/30; A61F 2310/00023; A61F 2310/00017; A61F 2/4405; A61F 2002/3095; A61F 2002/30952; A61F 2310/00029; A61F 2/30965; A61F 2310/00059; A61F 2310/00047; A61F 2002/4687
USPC ........... 600/407–469; 606/79, 88–96; 602/26
See application file for complete search history.

(56) References Cited

U.S. PATENT DOCUMENTS

| | | |
|---|---|---|
| D359,557 S | 6/1995 | Hayes |
| 5,490,409 A | 2/1996 | Weber |
| D403,066 S | 12/1998 | DeFonzo |
| D412,032 S | 7/1999 | Mikula-Curtis et al. |
| 6,006,581 A | 12/1999 | Holmes |
| D420,132 S | 2/2000 | Bucholz et al. |
| 6,035,691 A | 3/2000 | Lin et al. |
| D428,989 S | 8/2000 | Segermark et al. |
| 6,221,077 B1 | 4/2001 | Rinner et al. |
| 6,644,087 B1 | 11/2003 | Ralph et al. |
| 6,711,432 B1* | 3/2004 | Krause ................... A61B 17/15 128/922 |
| 6,755,839 B2 | 6/2004 | Van Hoeck et al. |
| D532,515 S | 11/2006 | Buttler et al. |
| D533,664 S | 12/2006 | Buttler et al. |
| 7,235,076 B2 | 6/2007 | Pacheco |
| 7,454,939 B2 | 11/2008 | Garner et al. |
| 7,491,180 B2 | 2/2009 | Pacheco |
| 7,623,902 B2 | 11/2009 | Pacheco |
| D606,195 S | 12/2009 | Eisen et al. |
| 7,658,610 B2 | 2/2010 | Knopp |
| D618,796 S | 6/2010 | Cantu et al. |
| 7,844,356 B2 | 11/2010 | Matov et al. |
| 7,957,824 B2 | 6/2011 | Boronvinskih et al. |
| 7,957,831 B2 | 6/2011 | Isaacs |
| 8,159,753 B2 | 4/2012 | Ojeda et al. |
| 8,167,884 B2 | 5/2012 | Pacheco |
| 8,206,396 B2* | 6/2012 | Trabish ................. A61F 2/4609 606/86 R |
| 8,214,014 B2 | 7/2012 | Pacheco |
| 8,257,083 B2* | 9/2012 | Berckmans, III .... A61C 8/0001 433/213 |
| D669,176 S | 10/2012 | Frey |
| D669,984 S | 10/2012 | Cheney et al. |
| 8,277,461 B2 | 10/2012 | Pacheco |
| 8,298,242 B2 | 10/2012 | Justis et al. |
| D672,038 S | 12/2012 | Frey |
| 8,357,111 B2* | 1/2013 | Caillouette .......... A61B 5/1071 385/12 |
| 8,419,740 B2* | 4/2013 | Aram ................... A61B 17/155 606/86 R |
| D685,087 S | 6/2013 | Voic |
| 8,540,719 B2 | 9/2013 | Peukert et al. |
| 8,549,888 B2 | 10/2013 | Isaacs |
| 8,607,603 B2 | 12/2013 | Justis et al. |
| 8,668,700 B2 | 3/2014 | Catanzarite |
| D705,929 S | 5/2014 | Frey |
| 8,721,651 B2 | 5/2014 | Loke et al. |
| 8,758,357 B2 | 6/2014 | Frey |
| 8,870,889 B2 | 10/2014 | Frey |
| D718,862 S | 12/2014 | Matheny |
| D718,863 S | 12/2014 | Matheny |
| D718,864 S | 12/2014 | Matheny |
| D726,914 S | 4/2015 | Matheny |
| 9,044,285 B2 | 6/2015 | Harper |
| 9,066,816 B2 | 6/2015 | Allard et al. |
| D738,498 S | 9/2015 | Frey et al. |
| D745,671 S | 12/2015 | Frey et al. |
| D745,672 S | 12/2015 | Frey et al. |
| D745,673 S | 12/2015 | Frey et al. |
| 9,198,678 B2 | 12/2015 | Frey et al. |
| 9,451,973 B2* | 9/2016 | Heilman ............ A61B 17/1778 |
| 2004/0097925 A1 | 5/2004 | Boehm et al. |
| 2004/0144149 A1 | 7/2004 | Strippgen et al. |
| 2004/0243481 A1 | 12/2004 | Bradbury et al. |
| 2005/0148843 A1 | 7/2005 | Roose |
| 2005/0262911 A1 | 12/2005 | Dankowicz et al. |
| 2006/0084986 A1 | 4/2006 | Grinberg et al. |
| 2006/0095044 A1 | 5/2006 | Grady, Jr. et al. |
| 2006/0149375 A1 | 7/2006 | Yuan et al. |
| 2006/0241385 A1 | 10/2006 | Dietz |
| 2007/0227216 A1 | 10/2007 | Schalliol |
| 2007/0288030 A1 | 12/2007 | Metzger et al. |
| 2008/0086127 A1 | 4/2008 | Patterson et al. |
| 2008/0114370 A1* | 5/2008 | Schoenefeld ...... A61B 17/1721 606/96 |
| 2008/0161815 A1 | 7/2008 | Schoenefeld et al. |
| 2008/0183214 A1 | 7/2008 | Copp et al. |
| 2008/0257363 A1 | 10/2008 | Schoenefeld et al. |
| 2008/0275452 A1 | 11/2008 | Lang et al. |
| 2008/0306552 A1 | 12/2008 | Winslow |

(56) References Cited

U.S. PATENT DOCUMENTS

| | | |
|---|---|---|
| 2008/0312659 A1 | 12/2008 | Metzger et al. |
| 2008/0319491 A1 | 12/2008 | Schoenefeld |
| 2009/0087276 A1 | 4/2009 | Rose |
| 2009/0088674 A1* | 4/2009 | Caillouette .......... A61B 5/1071 602/26 |
| 2009/0088761 A1* | 4/2009 | Roose .................. A61B 17/155 606/87 |
| 2009/0088763 A1* | 4/2009 | Aram ................... A61B 17/155 606/88 |
| 2009/0093816 A1* | 4/2009 | Roose .................. A61B 17/155 606/87 |
| 2009/0099567 A1* | 4/2009 | Zajac ................... A61B 17/155 606/79 |
| 2009/0105760 A1 | 4/2009 | Frey |
| 2009/0110498 A1 | 4/2009 | Park |
| 2009/0138020 A1 | 5/2009 | Park et al. |
| 2009/0187194 A1 | 7/2009 | Hamada |
| 2009/0198277 A1 | 8/2009 | Gordon et al. |
| 2009/0254093 A1 | 10/2009 | White et al. |
| 2009/0270868 A1 | 10/2009 | Park et al. |
| 2010/0016984 A1 | 1/2010 | Trabish |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0100193 A1 | 4/2010 | White |
| 2010/0152782 A1 | 6/2010 | Stone et al. |
| 2010/0191244 A1 | 7/2010 | White et al. |
| 2010/0217270 A1 | 8/2010 | Polinski et al. |
| 2010/0217336 A1 | 8/2010 | Crawford et al. |
| 2010/0305700 A1 | 12/2010 | Ben-Arye et al. |
| 2010/0324692 A1 | 12/2010 | Uthgenannt et al. |
| 2011/0015636 A1 | 1/2011 | Katrana et al. |
| 2011/0015639 A1 | 1/2011 | Metzger et al. |
| 2011/0046735 A1 | 2/2011 | Metzger et al. |
| 2011/0054478 A1 | 3/2011 | Vanasse et al. |
| 2011/0071533 A1 | 3/2011 | Metzger et al. |
| 2011/0093023 A1 | 4/2011 | Lee et al. |
| 2011/0093086 A1 | 4/2011 | Witt et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0213376 A1 | 9/2011 | Maxson et al. |
| 2011/0218545 A1 | 9/2011 | Catanzarite et al. |
| 2011/0224674 A1 | 9/2011 | White et al. |
| 2011/0288433 A1 | 11/2011 | Kelleher et al. |
| 2011/0319745 A1* | 12/2011 | Frey ....................... A61B 17/15 600/407 |
| 2012/0041445 A1* | 2/2012 | Roose ................ A61B 17/1746 606/96 |
| 2012/0130434 A1 | 5/2012 | Stemniski et al. |
| 2012/0179259 A1 | 7/2012 | McDonough et al. |
| 2012/0215315 A1 | 8/2012 | Hochschuler et al. |
| 2013/0006251 A1 | 1/2013 | Aram et al. |
| 2013/0053854 A1 | 2/2013 | Schoenefeld et al. |
| 2013/0110174 A1 | 5/2013 | Marik |
| 2013/0123850 A1 | 5/2013 | Schoenefeld et al. |
| 2014/0137618 A1 | 5/2014 | Isaacs |
| 2015/0047410 A1 | 2/2015 | Petit et al. |
| 2015/0127053 A1 | 5/2015 | Maruenda Paulino et al. |
| 2015/0297249 A1 | 10/2015 | Catanzarite |

FOREIGN PATENT DOCUMENTS

| | | |
|---|---|---|
| CN | 101390773 | 11/2010 |
| CN | 101953713 | 1/2011 |
| EP | 2168507 | 3/2010 |
| JP | 2008-514362 | 5/2008 |
| JP | D1508406 | 10/2014 |
| WO | WO 2006/039266 | 4/2006 |
| WO | WO 2007/145937 | 12/2007 |
| WO | WO 2008/027549 | 3/2008 |
| WO | WO 2009/035358 | 3/2009 |
| WO | WO 2009/129063 | 10/2009 |
| WO | WO 2009/105106 | 12/2009 |
| WO | WO 2010/033431 | 3/2010 |
| WO | WO 2010/148103 | 12/2010 |
| WO | WO 2011/041398 | 4/2011 |
| WO | WO 2011/080260 | 7/2011 |
| WO | WO 2011/106711 | 9/2011 |
| WO | WO 2011/109260 | 9/2011 |
| WO | WO 2012/152900 | 11/2012 |
| WO | WO 2013/041618 | 3/2013 |
| WO | WO 2013/104682 | 7/2013 |
| WO | WO 2014/088801 | 6/2014 |
| WO | WO 2014/143762 | 9/2014 |

OTHER PUBLICATIONS

Official Action with English Translation for China Patent Application No. 201380030638.3, dated May 25, 2016 11 pages.
International Preliminary Report on Patentability for International (PCT) Patent Application No. PCT/US2014/041379, mailed Dec. 17, 2015 6 pages.
U.S. Appl. No. 29/538,633, filed Sep. 4, 2015, Frey et al.
Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).
Lu et al. "A Novel Patient-Specific Navigational Template for Cervical Pedicle Screw Placement," Spine, Dec. 15, 2009, vol. 34, No. 26, pp. E959-E966 (Abstract Only).
Owen et al. "Rapid prototype patient-specific drill template for cervical pedicle screw placement." Computer Aided Surgery, Sep. 2007, vol. 12, No. 5, pp. 303-308 (Abstract Only).
Ryken et al. "Image-based drill templates for cervical pedicle screw placement Laboratory investigation," Journal of Neurosurgery, Jan. 2009, vol. 10, No. 1 (Abstract Only).
Yin et al. "Computer aid designed digital targeting template of pedicle of vertebral arch for atlantoaxial nailing," IT in Medicine & Education, 2009. !ITIME '09. Aug. 14-16, 2009, vol. 1 (Abstract Only).
International Search Report and Written Opinion for International (PCT) Patent Application No. PCT/US11/42412 mailed Nov. 8, 2011, 8 pages.
International Preliminary Report on Patentability for International (PCT) Patent Application No. PCT/US11/42412 mailed Jan. 17, 2013, 7 pages.
Official Action for Australian Patent Application No. 2011276468 dated Apr. 10, 2013, 3 pages.
Partial Search Report for European Patent Application No. 11804191.2, dated Jan. 20, 2015 6 pages.
Extended Search Report for European Patent Application No. 11804191.2, dated May 7, 2015 8 pages.
Official Action with English Translation for Japan Patent Application No. 2013-518663, mailed May 12, 2015 4 pages.
Notice of Allowance with English Translation for Japan Patent Application No. 2013-518663, mailed Dec. 8, 2015 4 pages.
International Search Report and Written Opinion for International (PCT) Patent Application No. PCT/US2013/036535, mailed Jun. 26, 2013 8 pages.
International Preliminary Report on Patentability for International (PCT) Patent Application No. PCT/US2013/036535, mailed Oct. 30, 2014 7 pages.
International Search Report and Written Opinion for International (PCT) Patent Application No. PCT/US15/32356, mailed Oct. 28, 2015 10 pages.
International Search Report and Written Opinion for International (PCT) Patent Application No. PCT/US2014/041379, mailed Oct. 28, 2014 7 pages.

(56) References Cited

OTHER PUBLICATIONS

Official Action for U.S. Appl. No. 13/172,683, mailed Sep. 10, 2013 7 pages.
Official Action for U.S. Appl. No. 13/172,683, mailed Feb. 24, 2014, 10 pages.
Notice of Allowance for U.S. Appl. No. 13/172,683 mailed Apr. 23, 2014, 7 pages.
Notice of Allowance for U.S. Appl. No. 29/409,734, mailed May 11, 2012 8 pages.
Notice of Allowance for U.S. Appl. No. 29/427,918, mailed Oct. 15, 2012 9 pages.
Notice of Allowance for U.S. Appl. No. 29/432,668 mailed Nov. 27, 2013, 11 pages.
Notice of Allowance for U.S. Appl. No. 29/476,709, mailed Nov. 6, 2015 8 pages.
Notice of Allowance for U.S. Appl. No. 29/476,705, mailed Oct. 7, 2015 8 pages.
Notice of Allowance for U.S. Appl. No. 29/476,699, mailed Oct. 2, 2015 8 pages.
Notice of Allowance for U.S. Appl. No. 29/496,231, mailed Jul. 23, 2015 10 pages.
Notice of Allowance for U.S. Appl. No. 29/538,633, mailed Jan. 6, 2016 10 pages.
Official Action for U.S. Appl. No. 13/841,069, mailed Jul. 31, 2014 9 pages.
Notice of Allowance for U.S. Appl. No. 13/841,069, mailed Sep. 18, 2014 7 pages.
Official Action for U.S. Appl. No. 14/298,634, mailed Apr. 27, 2015 8 pages.
Official Action for U.S. Appl. No. 14/298,634, mailed Jul. 7, 2015 6 pages.
Notice of Allowance for U.S. Appl. No. 14/298,624, mailed Oct. 7, 2015 7 pages.

* cited by examiner

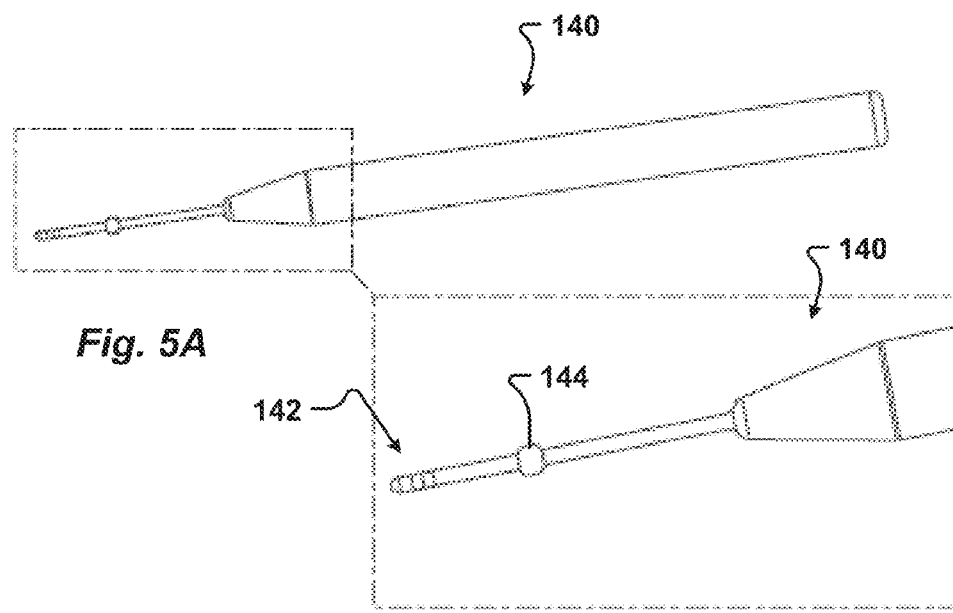
Fig. 5A
Fig. 5B
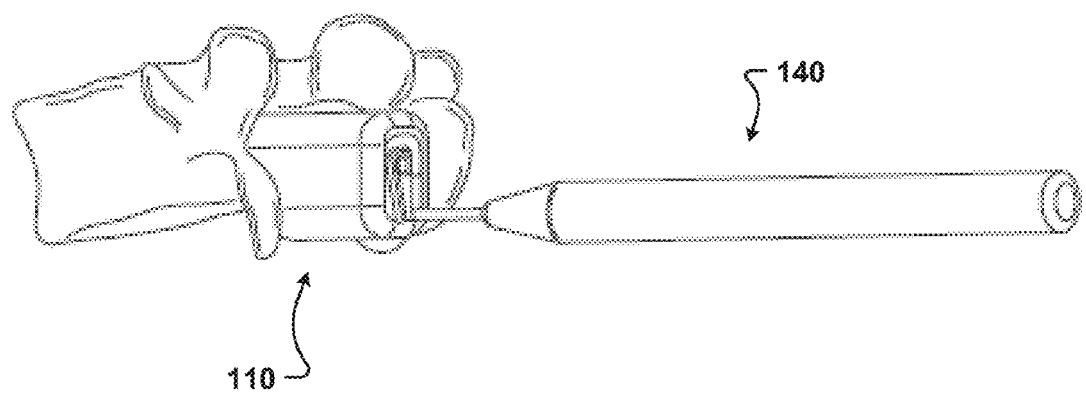
Fig. 5C

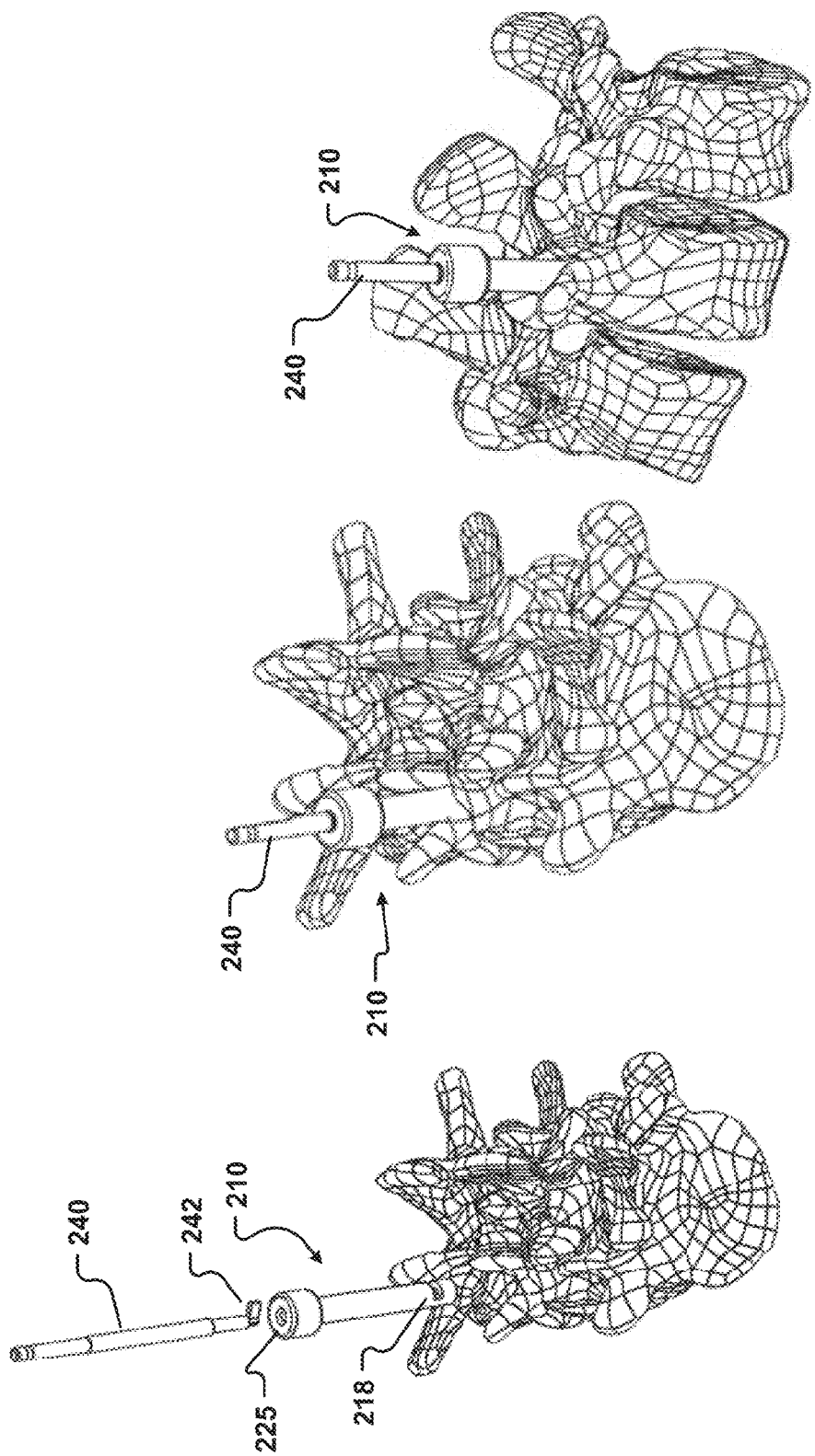

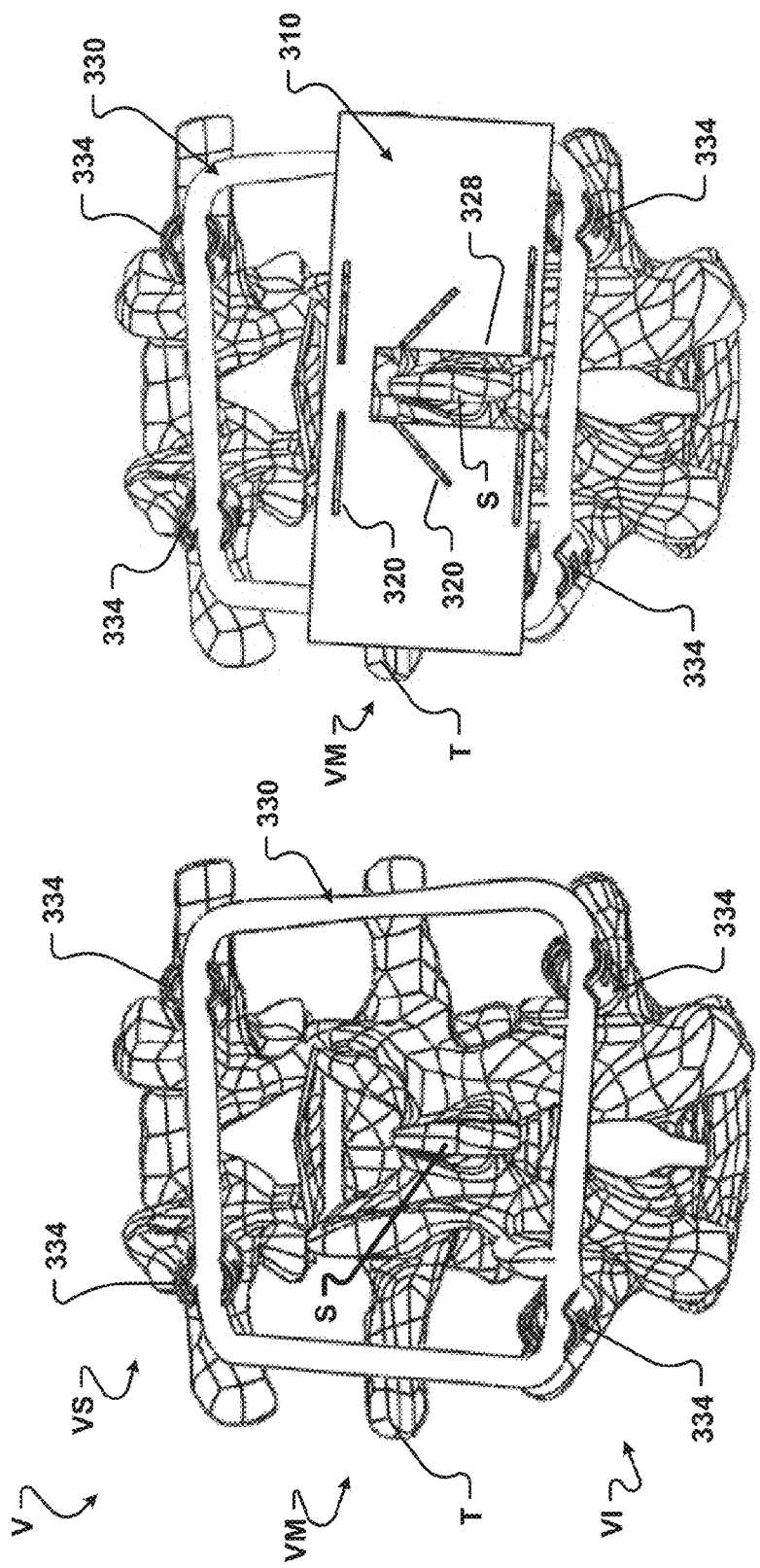

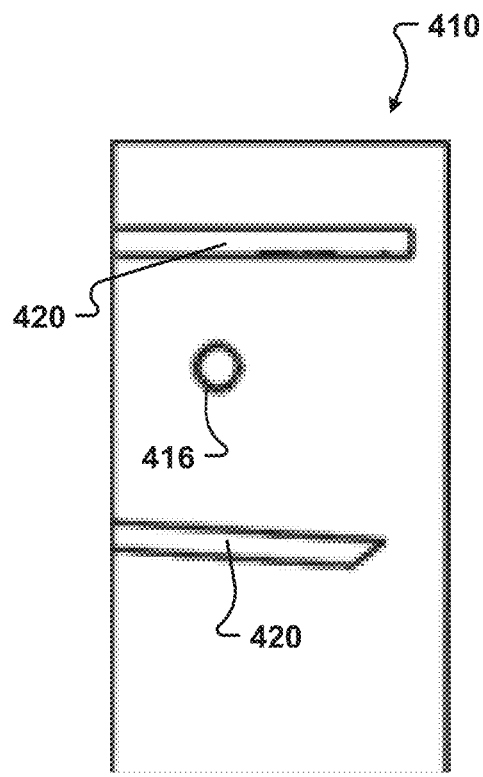
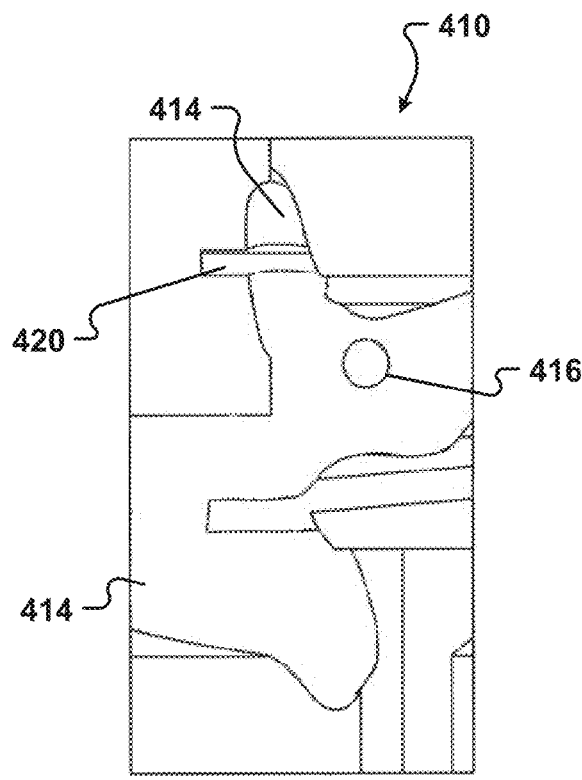
Fig. 9A    Fig. 9B
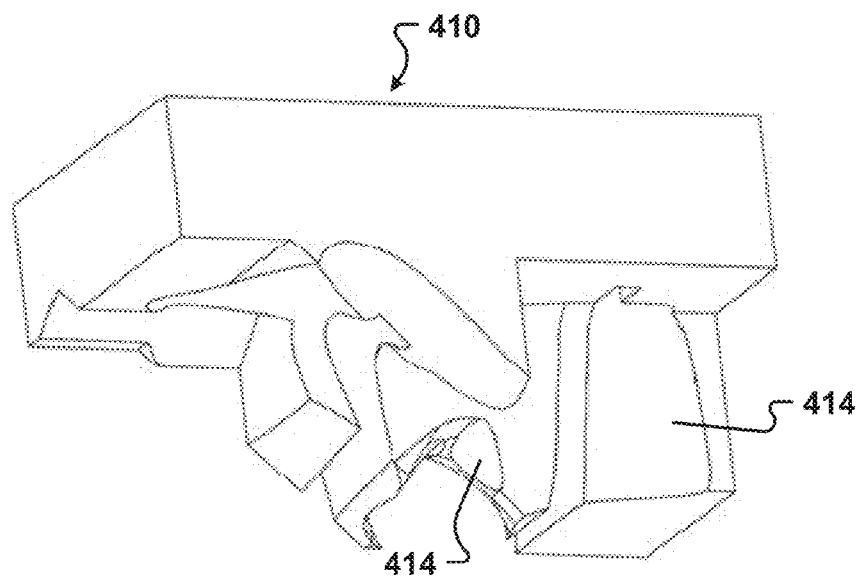
Fig. 9C

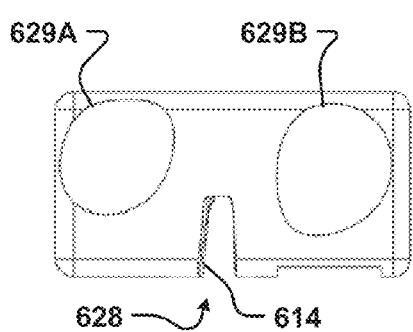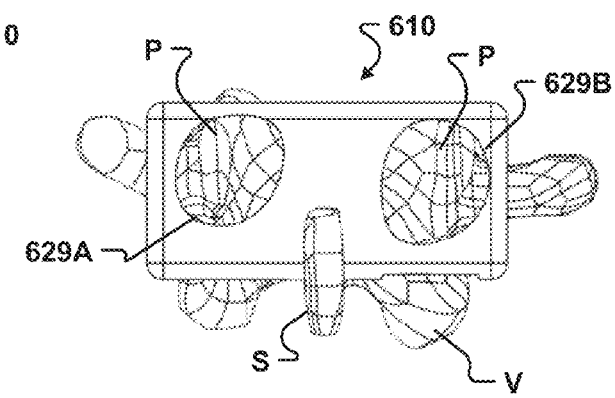
*Fig. 11A*     *Fig. 11B*
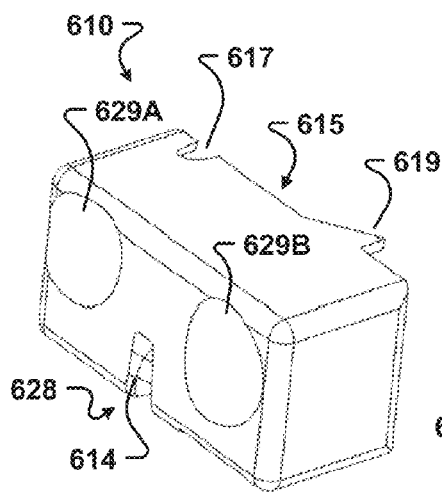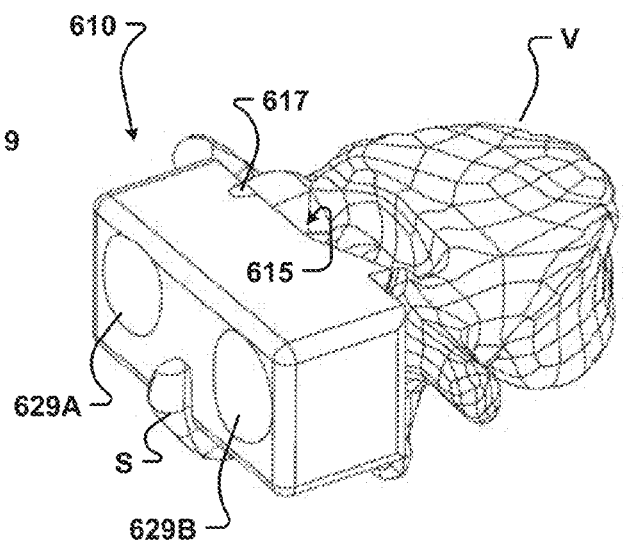
*Fig. 11C*     *Fig. 11D*
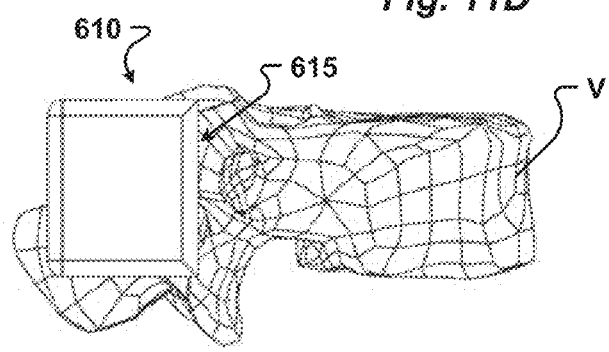
*Fig. 11E*

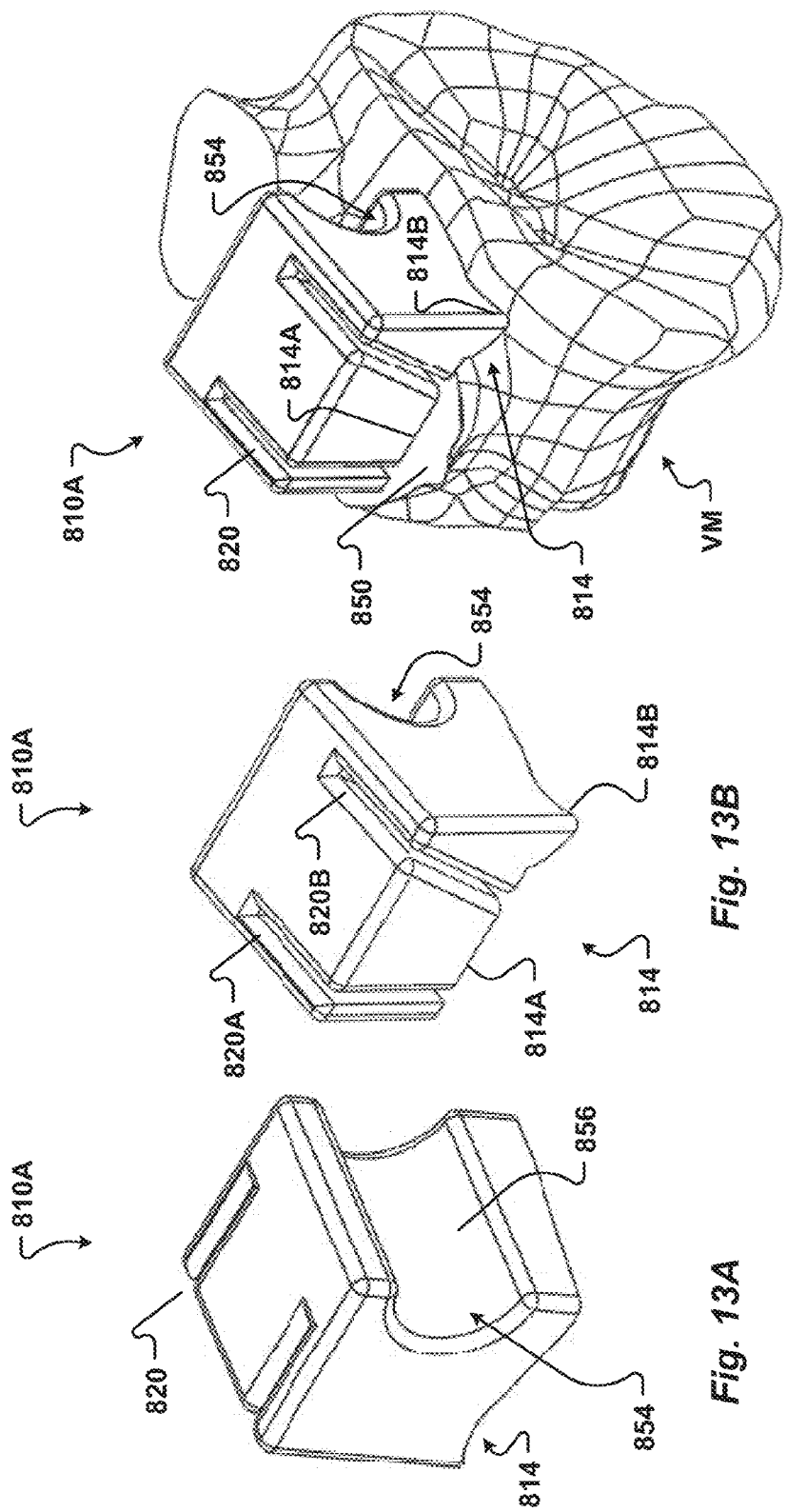

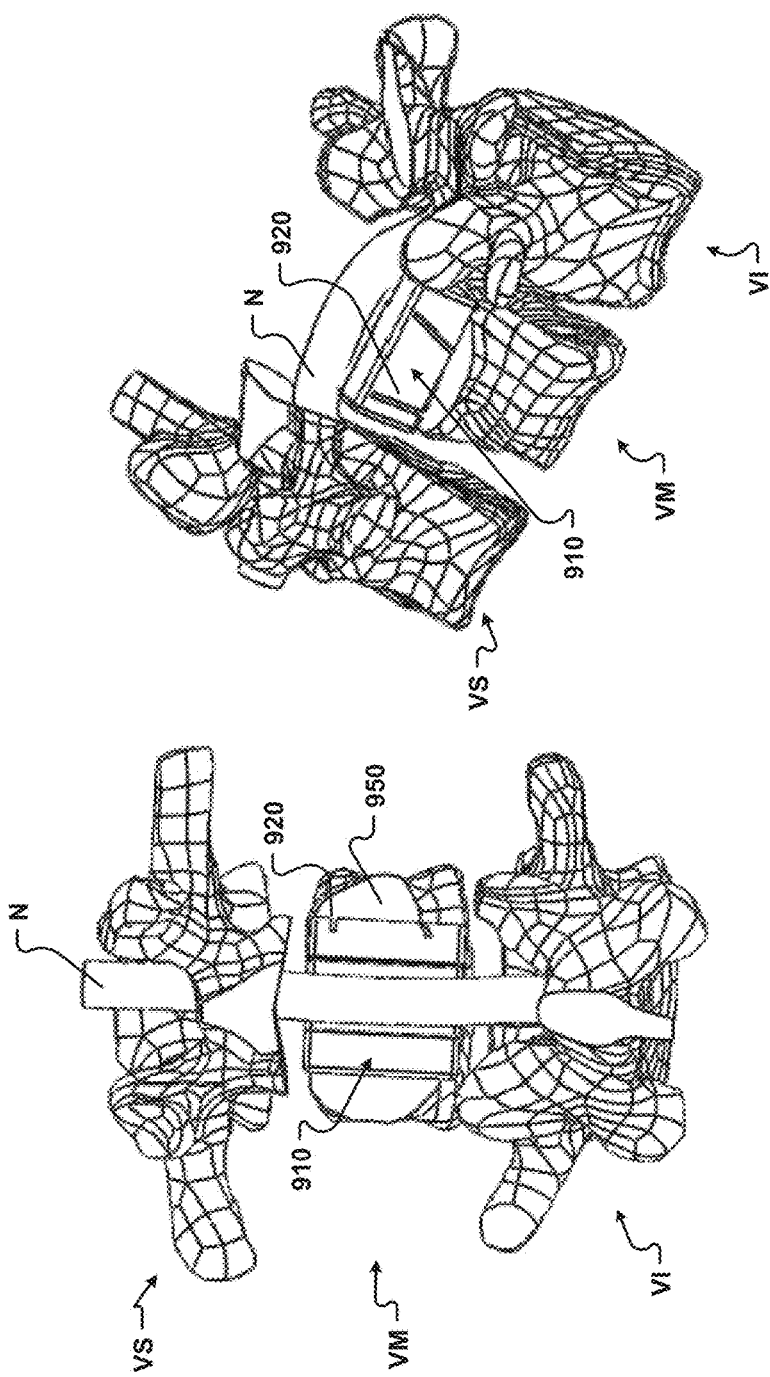

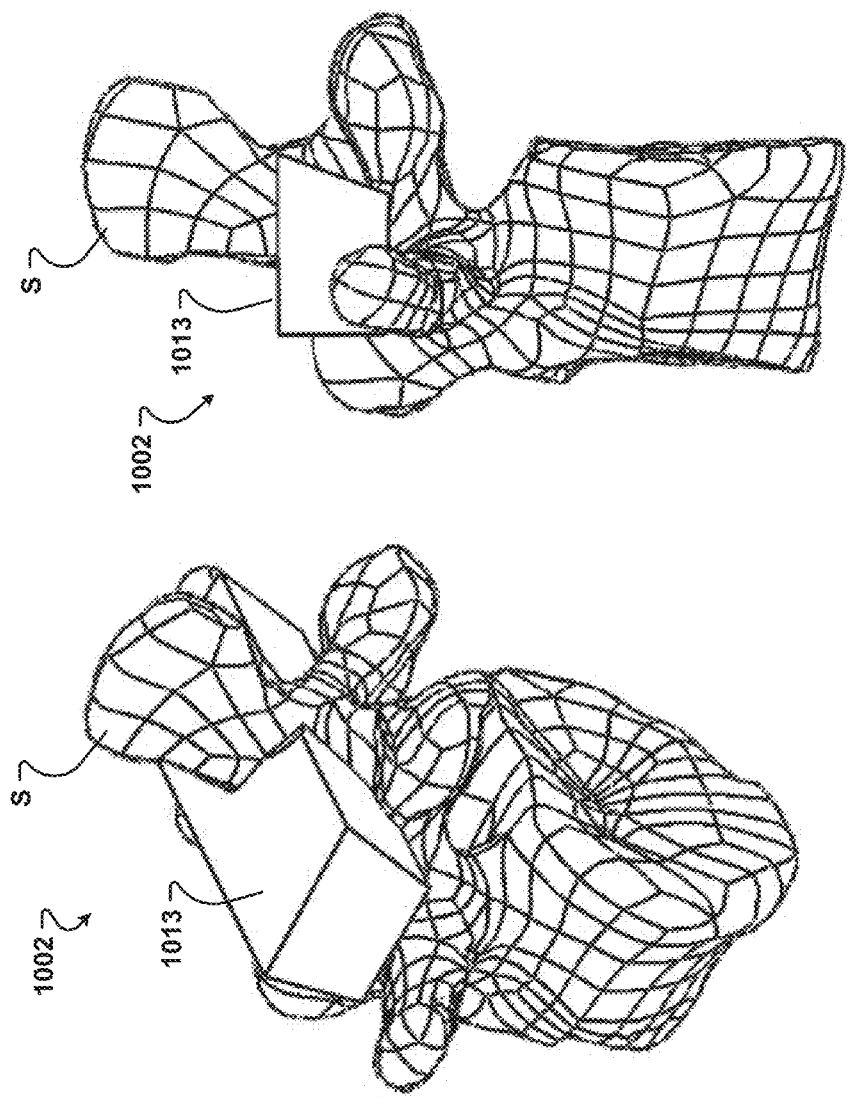

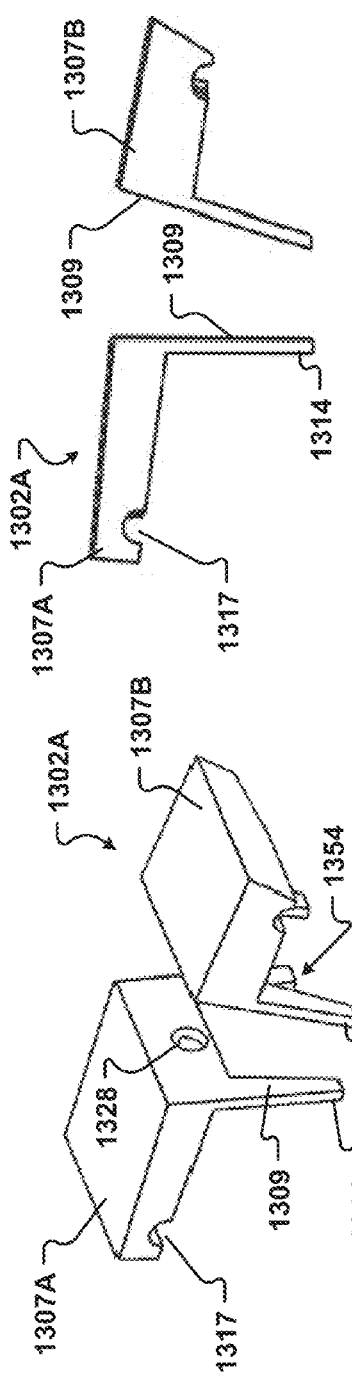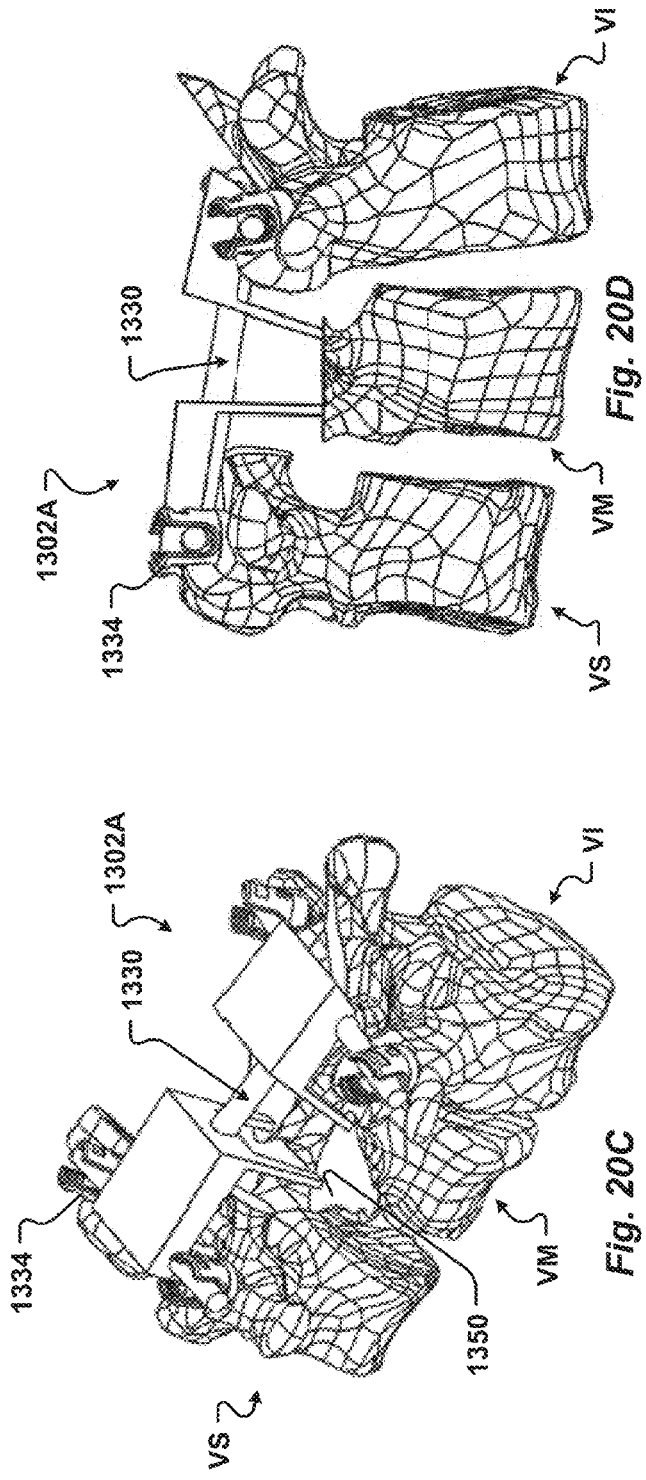

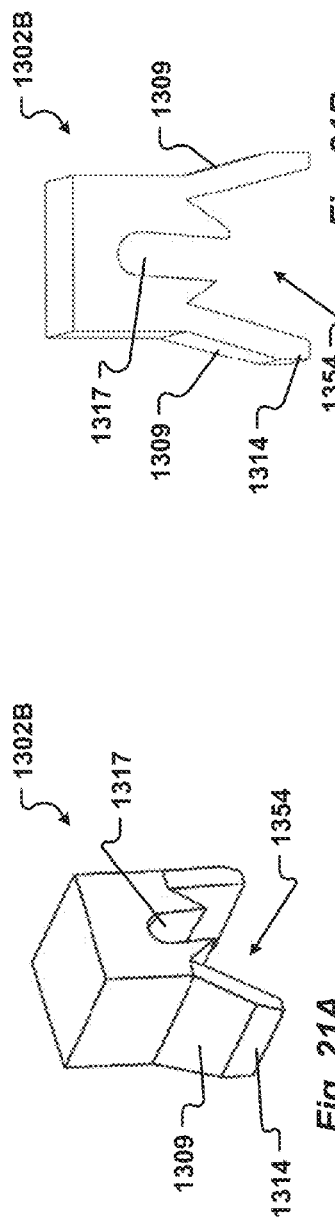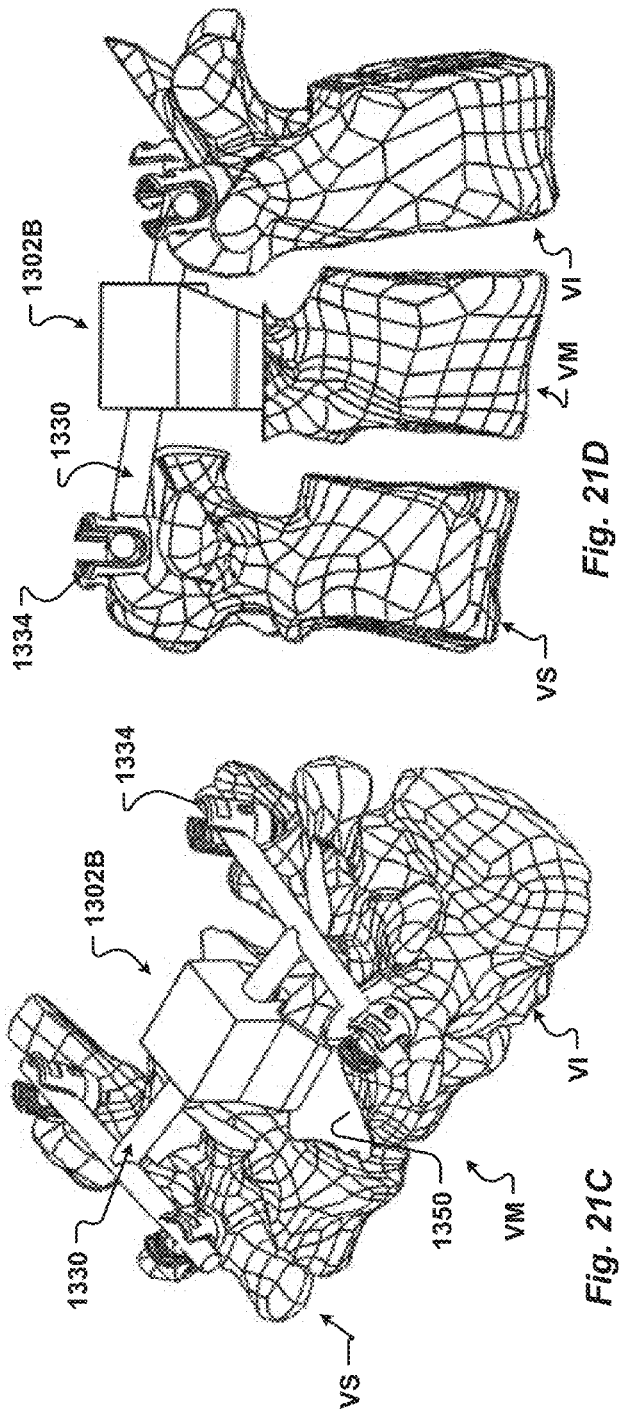

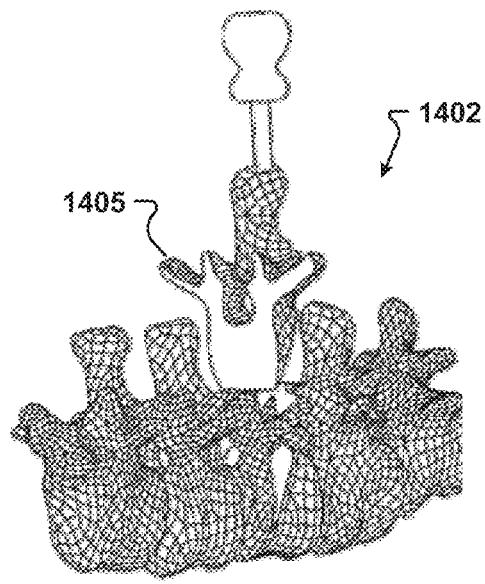
*Fig. 22A*
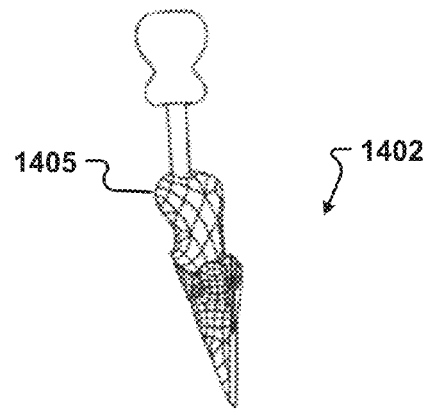
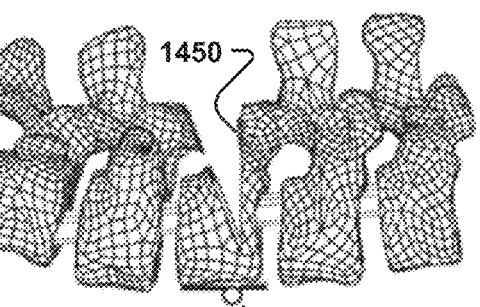
*Fig. 22B*
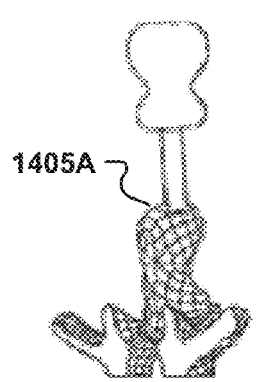
*Fig. 22C*
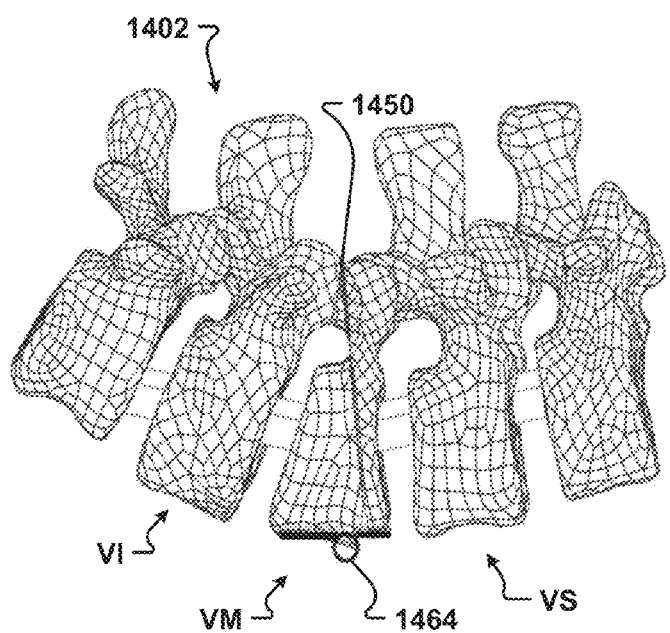
*Fig. 22D*

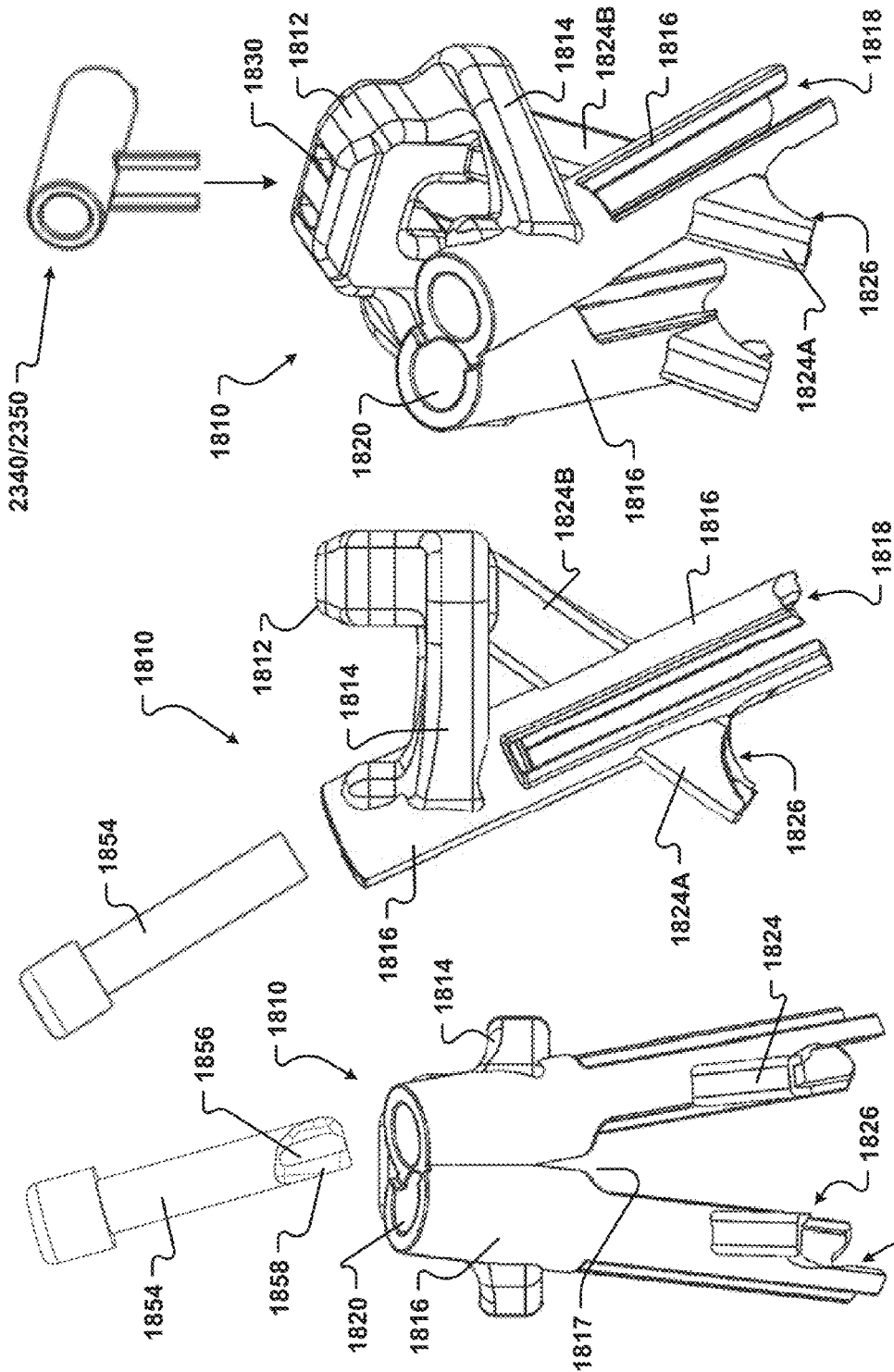

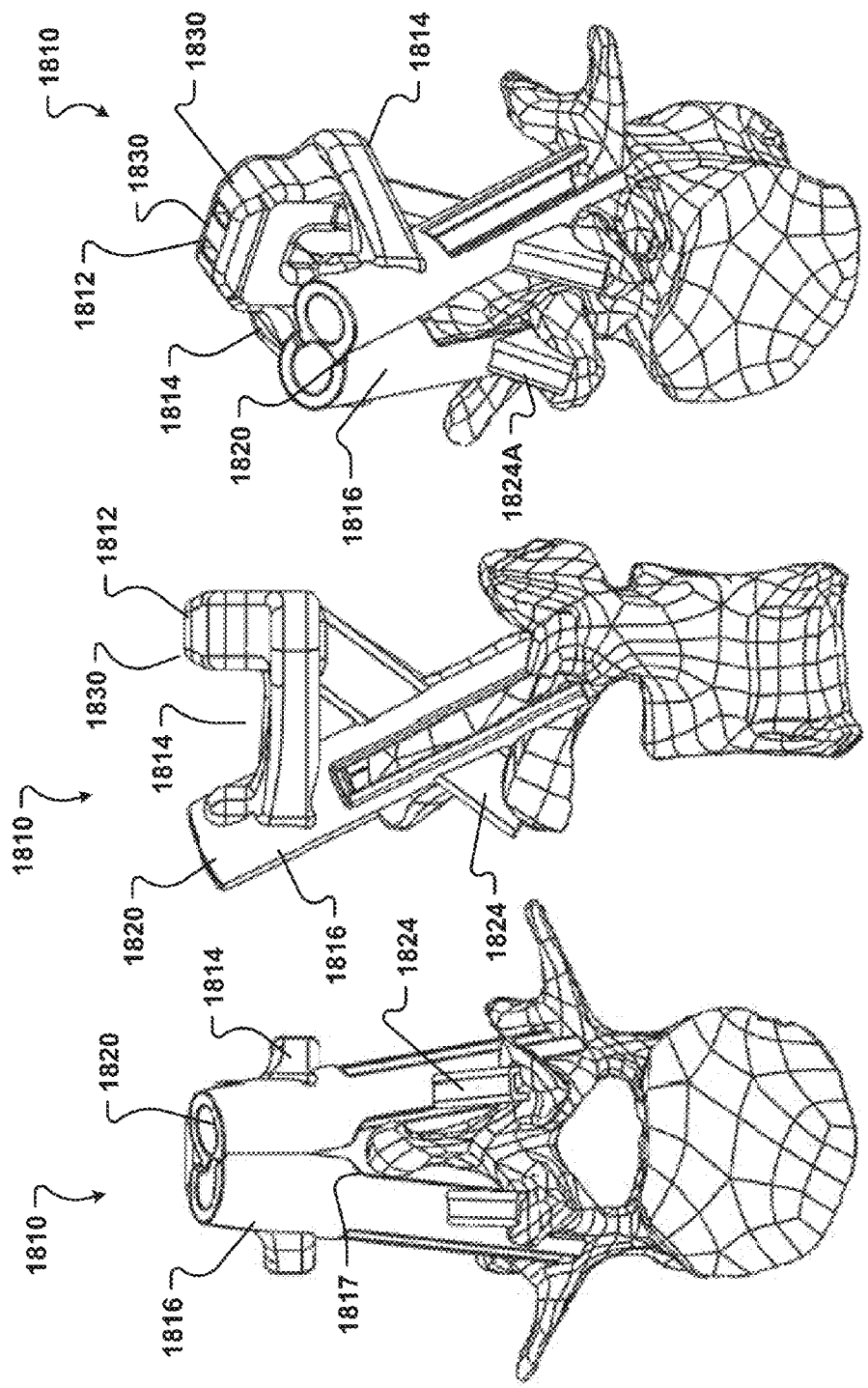

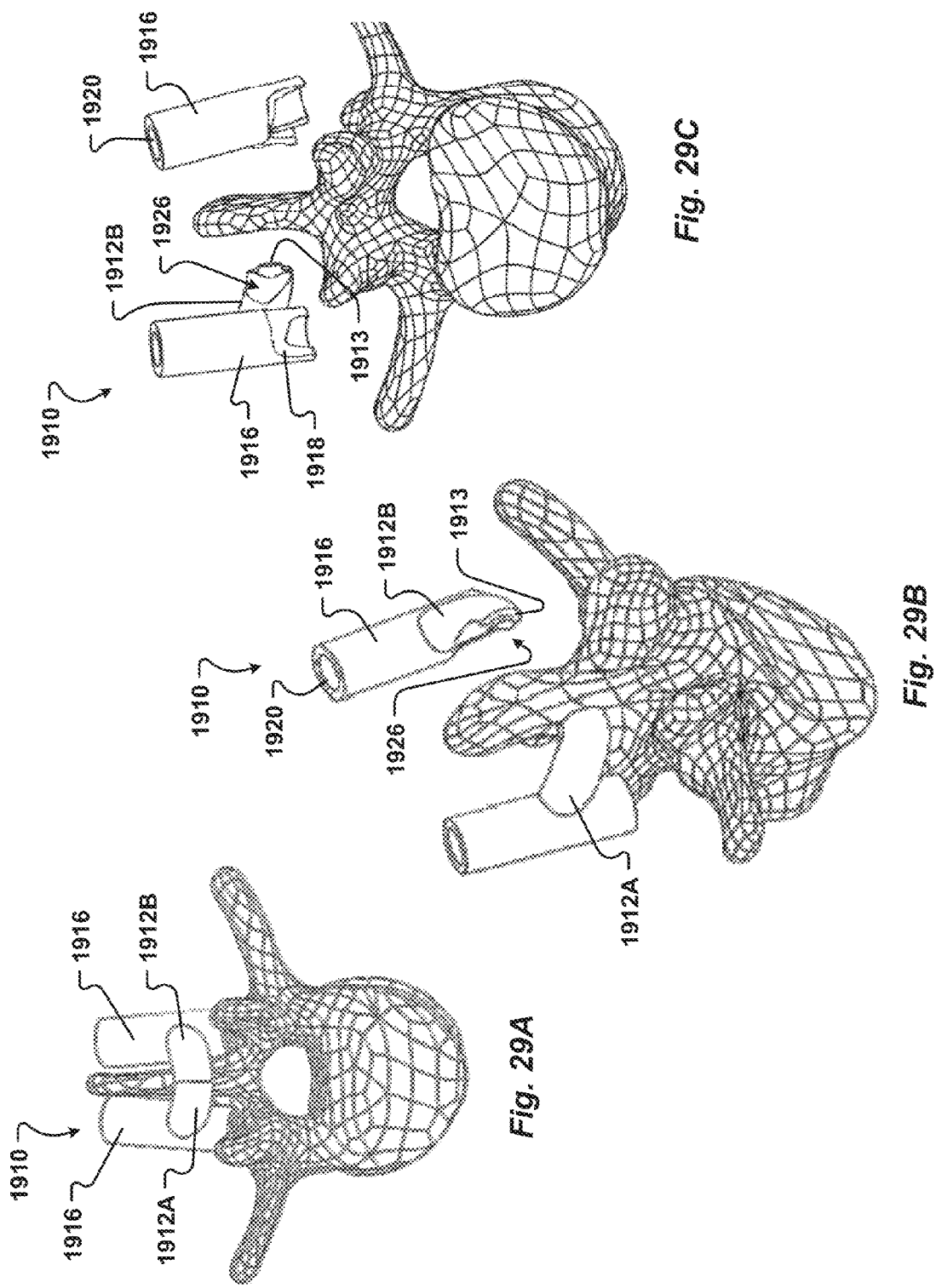

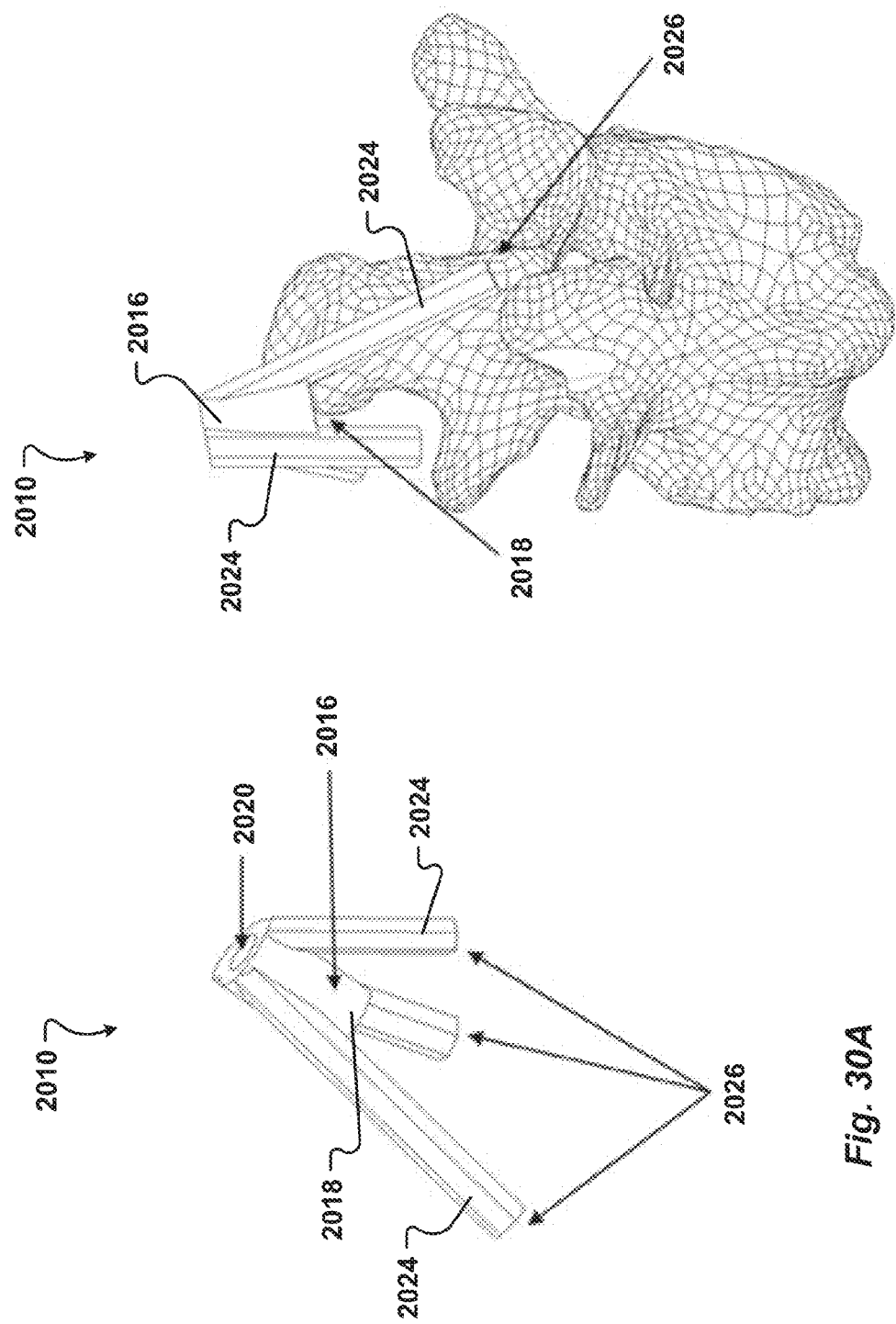

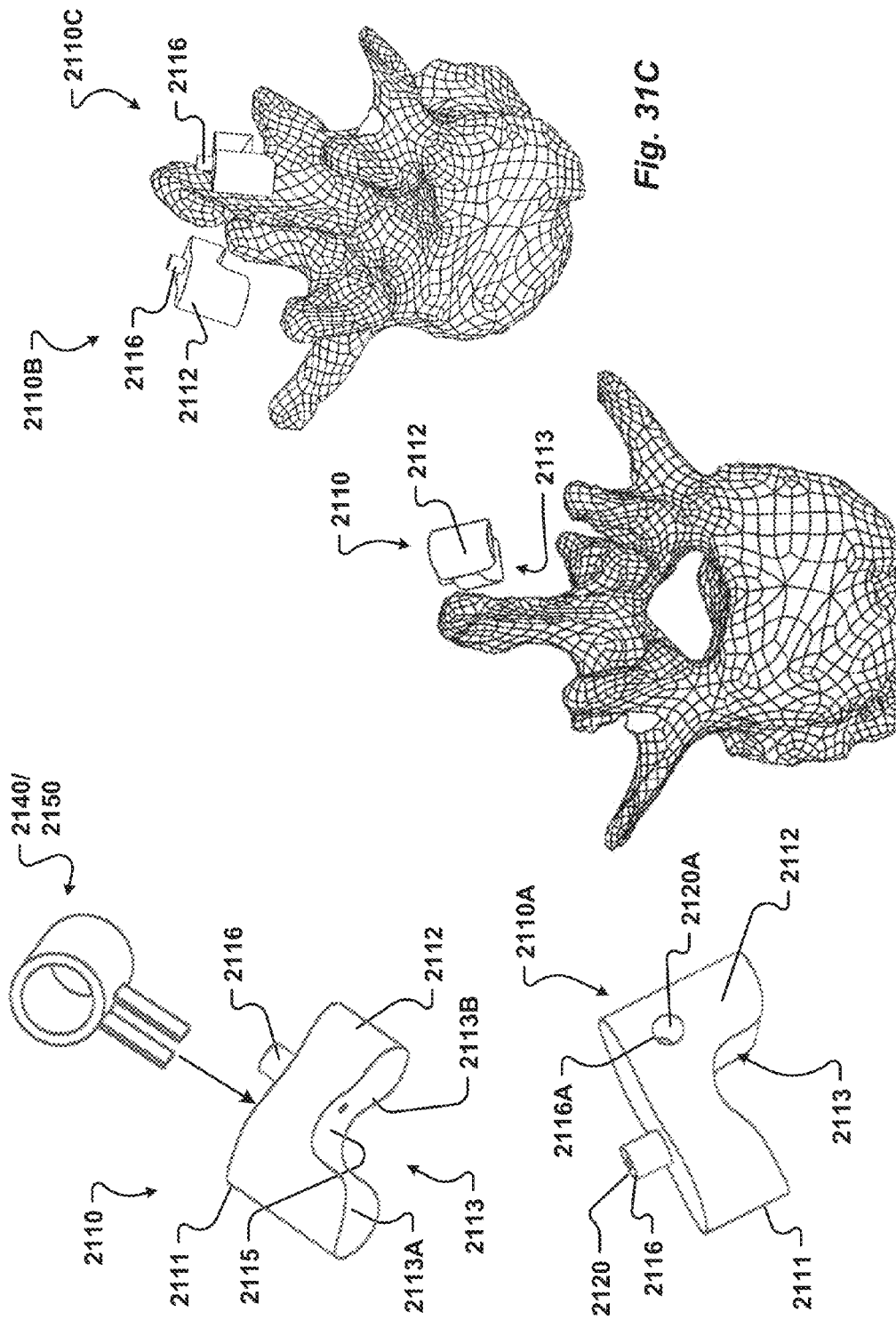

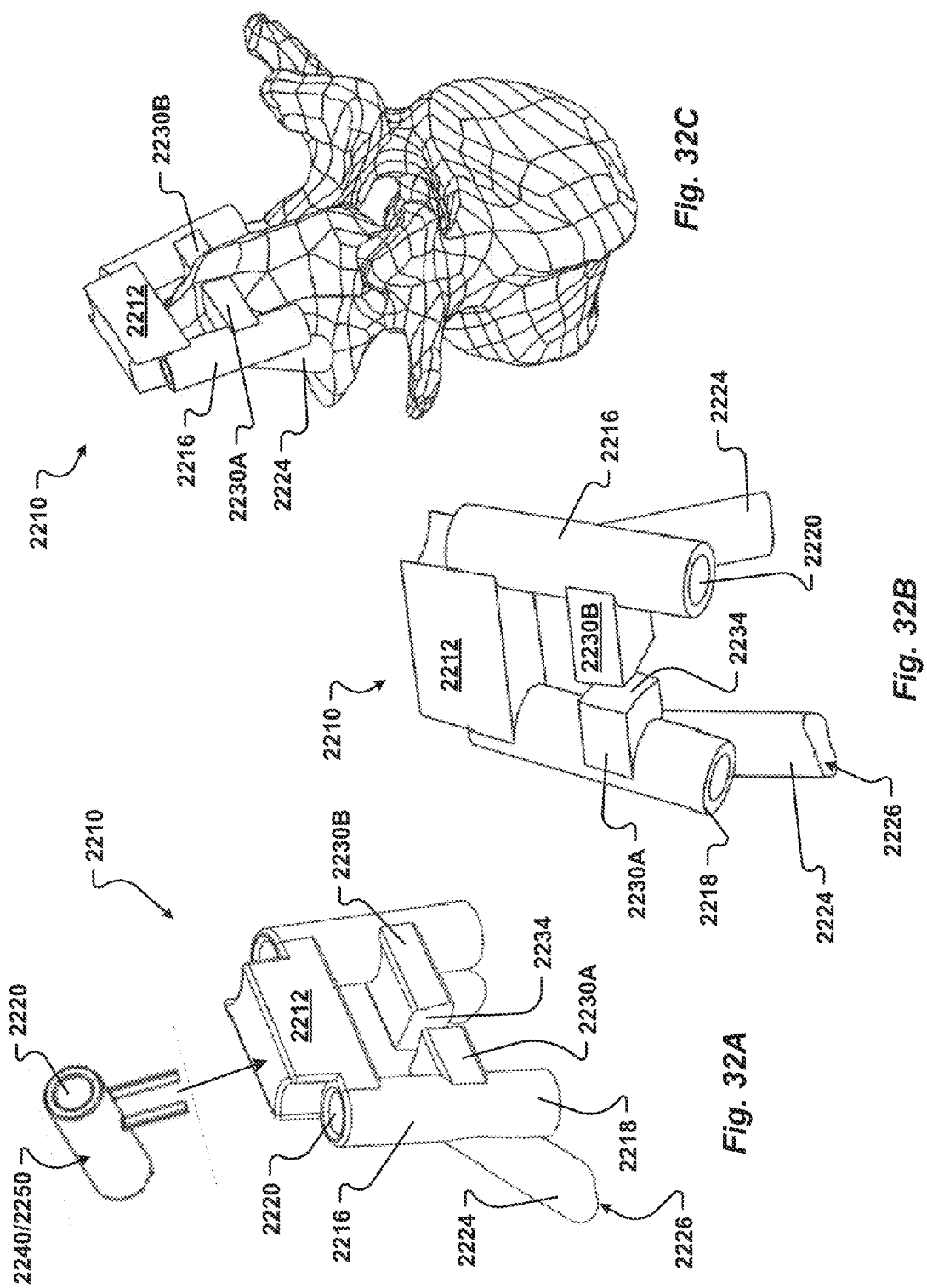

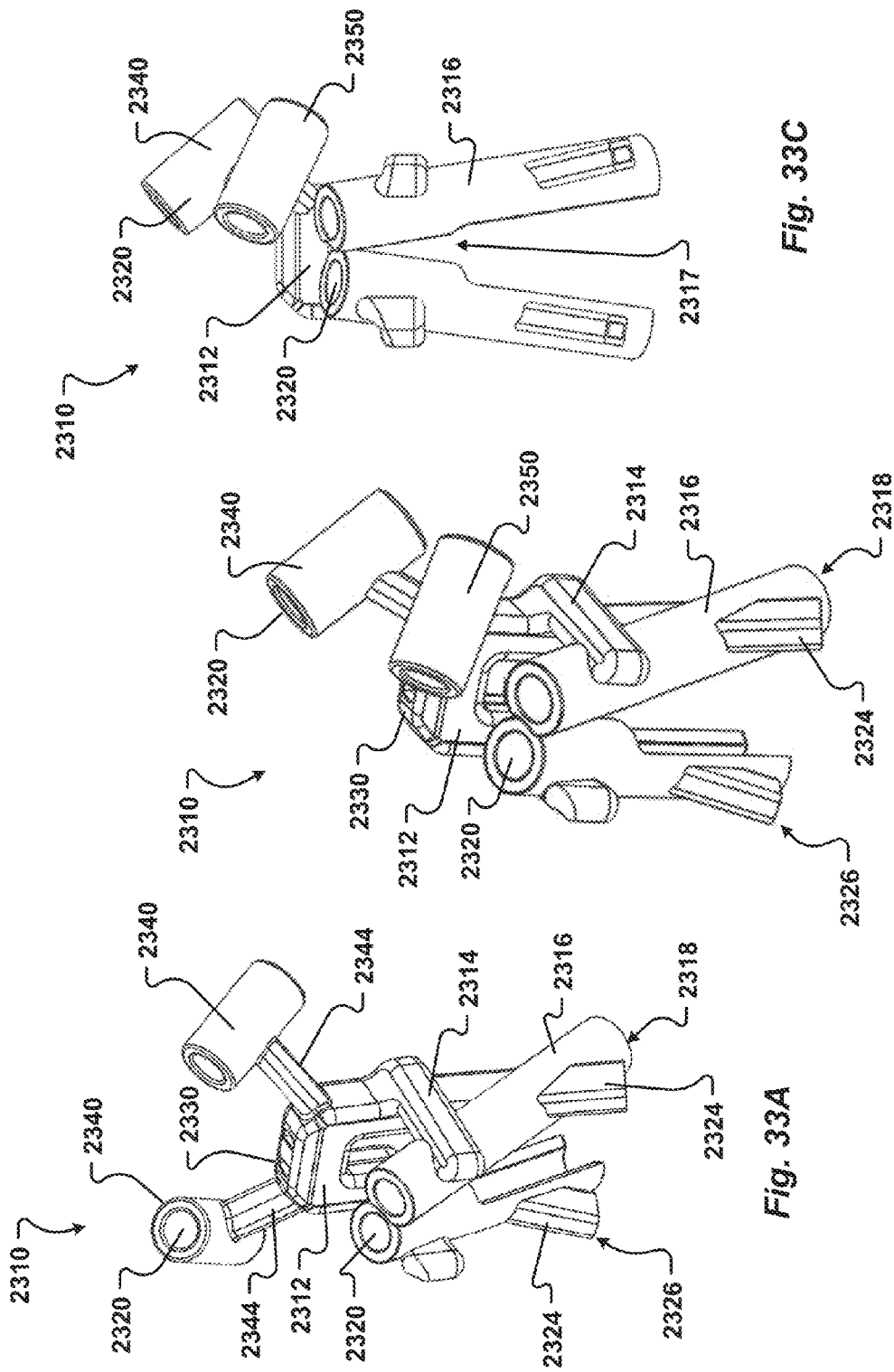

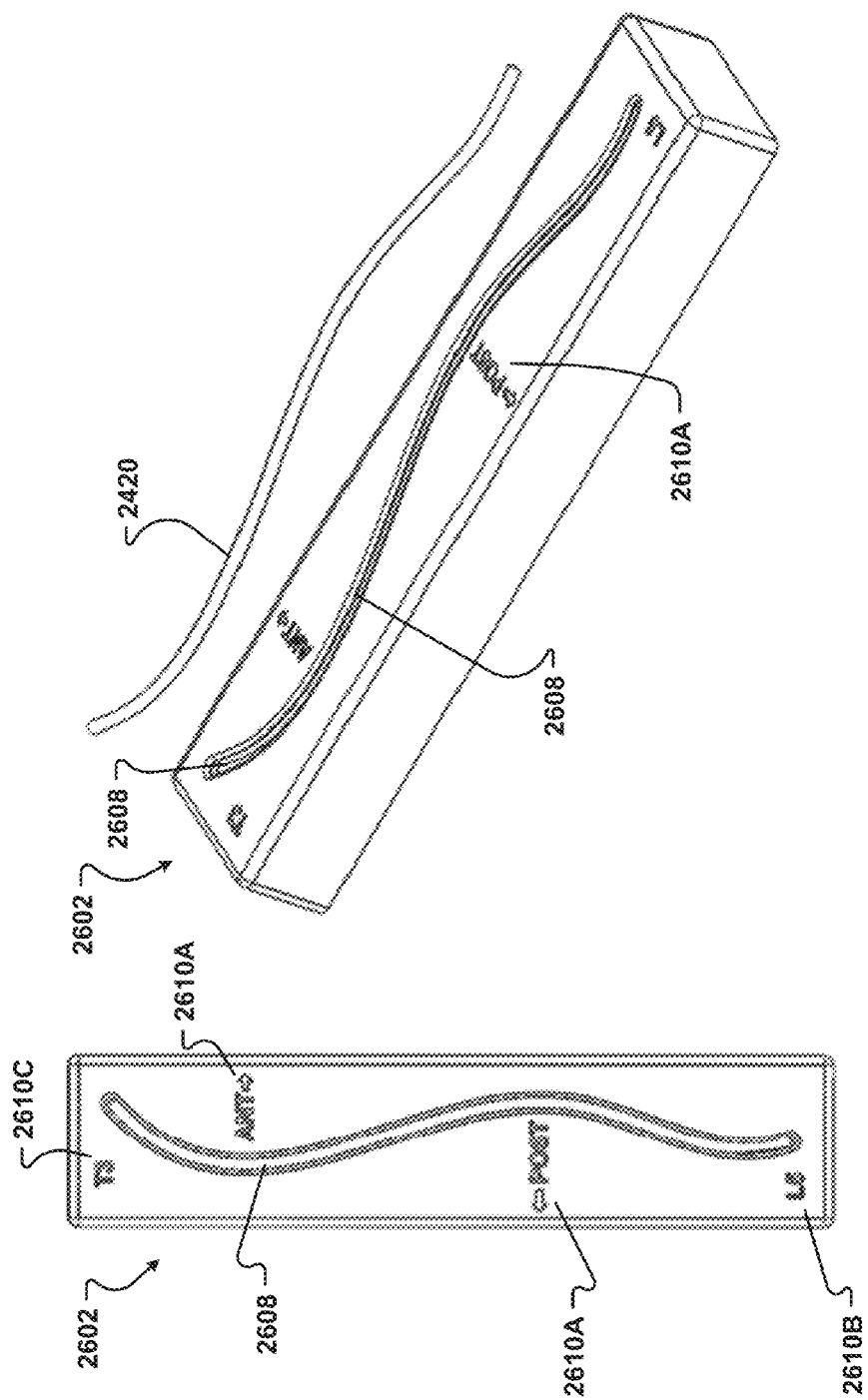

PATIENT-MATCHED APPARATUS AND METHODS FOR PERFORMING SURGICAL PROCEDURES

CROSS-REFERENCE TO RELATED APPLICATIONS

This application is a continuation-in-part of U.S. patent application Ser. No. 14/298,634, filed Jun. 6, 2014 and claims priority under 35 U.S.C. §119(e) to U.S. Provisional Application Ser. No. 62/162,466, filed May 15, 2015. U.S. patent application Ser. No. 14/298,634 claims the priority to U.S. Provisional Patent Application Nos. 61/832,583 filed Jun. 7, 2013, 61/845,463 filed Jul. 12, 2013 and 61/877,837 filed Sep. 13, 2013 and is a continuation-in-part of U.S. patent application Ser. No. 13/841,069, filed Mar. 15, 2013, which claims the priority to U.S. Provisional Patent Application Nos. 61/359,710 filed Jun. 29, 2010, 61/393,695 filed Oct. 15, 2010, and 61/625,559 filed Apr. 17, 2012. U.S. patent application Ser. No. 13/841,069 is a continuation in part of U.S. patent application Ser. No. 13/172,683, filed Jun. 29, 2011, which issued as U.S. Pat. No. 8,758,357 on Jun. 24, 2014. U.S. patent application Ser. No. 13/172,683 claims priority to U.S. Provisional Patent Application No. 61/359,710, filed Jun. 29, 2010. These applications are all incorporated by reference herein in their entireties.

FIELD OF THE INVENTION

The present disclosure relates to the field of medical devices and is generally directed toward apparatus configurable for use with a specific patient in a surgical setting based on the patient's unique anatomical features, and methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan that accounts for the unique and sometimes irregular anatomical features of a particular patient. For example, the implantation of pedicle screws in a vertebral body (as an adjunct or stand-alone stabilization mechanism) is well accepted amongst surgeons who treat various spine pathologies, and although the performance of various pedicle screw constructs have become predictable, there are still multiple challenges with the placement and insertion of the pedicle screws or other bone anchors. The challenges occur when a surgeon is unable to reference boney landmarks due to previous surgery or when the patient's anatomy is irregular in shape.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a custom implant based on the dynamic nature of the anatomical structures the custom implant is designed to associate with. This data, while currently used by surgeons in surgery planning, is largely unused for creating a customized set of instruments or other surgical devices that are designed to complement the patient's unique anatomy.

The prior art fails to teach a system for creating a suite of surgical apparatus based on the data set derived from the MRI or CT scan. For example, the use of the patient-specific data set for a vertebral body may allow a surgeon to accommodate for subtle variations in the position and orientation of a plate or other bone anchor to avoid particular boney anatomy or irregularities in the positioning and alignment of the adjoining vertebral bodies. As another example, the use of these data sets may also assist a surgeon in selecting a desired trajectory for an implantable device so as to avoid, for example, crossing the pedicle wall and violating the spinal canal during an actual procedure. The use of the data sets permit the surgeon to avoid these types of mistakes by creating customized tools and instruments, which may comprise orientation, end-stops or other safety related features to avoid over-torque and over-insertion of any implantable devices. The data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide apparatus suitable for use with a surgical procedure that is adapted and/or configured and/or capable of conforming to a plurality of anatomical features of a particular patient and/or to one or more additional apparatus to assist the surgeon in completing the surgical procedure(s) safely and efficiently, and that otherwise significantly reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel system and method is described for developing customized apparatus for use in one or more surgical procedures. The system and method according to this embodiment uses a patient's unique morphology, which may be derived from capturing MRI data or CT or other data to derive one or more "Patient Matched" apparatus, which comprises complementary surfaces based on a plurality of data points from the MRI or CT data. Each "Patient Matched" apparatus is matched and oriented around the patient's own anatomy, the desired insertional trajectories (which may be verified in a pre-operative setting using 3D CAD software, such as the software disclosed in WO 2008027549, which is incorporated by reference herein in its entirety), and according to one embodiment described herein, other apparatus used during the surgical procedure.

By way of providing additional background, context, and to further satisfy the written description requirements of 35 U.S.C. §112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No.

6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Various surgical procedures may be performed through introduction of rods or plates, screws or other devices into adjacent boney anatomy to join various portions of, for example, a vertebra to a corresponding portion on an adjacent vertebra. Surgical procedures are often performed in the sacroiliac, lumbar, thoracic, interbody, or cervical spine regions of a patient. The procedures performed in these areas are often designed to stop and/or eliminate all motion in the spinal segment by destruction of some or all of the joints in that segment and further utilizing bone graft material and/or rigid implantable fixation devices for securing the adjacent vertebrae. By eliminating movement, back pain and further degenerative disc disease may be reduced or avoided. Fusion requires tools for accessing the vertebrae, such as surgical cannulae for the procedures, and other tools for implanting the desired implant, bioactive material, etc. Such procedures often require introduction of additional tools to prepare a site for implantation. These tools may include drills, drill guides, debridement tools, irrigation devices, vises, clamps, cannula, and other insertion/retraction tools.

Spinal and other surgeries may be performed by a number of different procedures, as opposed to conventional surgical procedures and methods, which typically require cutting of muscles, removal of bone, and retraction of other natural elements. During a MIS procedure, including procedures using the apparatus of the present invention, a less destructive approach to the patient anatomy is carried out by using retractor tubes or portals, which take advantage of anatomy and current technology to limit the damage to intervening structures.

In a typical surgical procedure on the spine, skeletal landmarks are established fluoroscopically and a small incision is made over the landmark(s). According to various methods known in the prior art, a series of dilators are applied until one or more cannula is placed over the anatomic structure. In some procedures, a microscope is then placed over the operative site to provide illumination and magnification with a three dimensional view of the anatomical site to ensure that the surgeon is able to accurately locate the desired patient anatomy and properly position and orient any tool, instrument or other surgical device used during the procedure. The microscope, however, is an expensive and unwieldy device requiring uncomfortable gyrations of the surgeon's back and neck in order to gain the necessary view, and is also a nuisance to drape (a large, sterile plastic bag has to be placed over the eight foot tall structure). The use of adequate illumination is also difficult to direct due to the size of the microscope.

A significant danger of performing operations on the spine, and in particular accessing an intervertebral space during a MIS surgery on the spine, is that of inadvertently contacting or damaging the para-spinal nerves, including the exiting nerve roots, traversing nerves and the nerves of the cauda equina. The exact location of these para-spinal nerves cannot be precisely determined prior to the commencement of surgery, and therefore are dependent on a surgeon's ability to visually locate the same after the initial incision is made. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannula are received through the patient's back, such as when performing minimally invasive spinal surgery, minor blood vessels are ruptured, thereby blocking the surgeon's vision inside the intervertebral region after the cannula has been inserted. Other anatomical features at a particular patient may also obstruct the surgeon's view or make it difficult to provide illumination within the cannula. Therefore, one particular shortcoming that is addressed by the present disclosure is to provide devices which are patient-matched to facilitate proper location and orientation without use of microscopes or other equipment and that otherwise eliminate the problems associated with prior art procedures on the spine, including MIS procedures.

The customized and integrated matching aspects of this presently disclosed system provides an advantage over the prior art, in particular by providing a plurality of interlocking and/or matching points for each apparatus, which in turn reduces the likelihood of misalignment, misplacement and subsequent mistake during the surgical procedure(s).

Accordingly, one aspect of the present disclosure is to provide a method for preparing a customized surgical device or instrument, which in a preferred embodiment comprises, but is not limited to: (1) obtaining data associated with a patient's anatomy; (2) converting the data obtained to a 3-dimensional data set(s); (3) determining at least one trajectory or path for facilitating a surgical procedure to be performed on the patient; (4) determining at least one surface associated with the patient's anatomy; (5) generating a 3-dimensional representation of the customized surgical device or instrument, which incorporates the at least one trajectory of path and a matching surface to the at least one surface associated with the patient's anatomy; and (6) fabricating the customized surgical device or instrument using the 3-dimensional representation.

According to another aspect of the present disclosure, a system and method for facilitating a surgical procedure(s) comprises, but is not limited to: (1) Obtaining data associated with the patient's anatomy by way of a MRI or CT scan; (2) Converting the MRI or CT scan data to a 3-Dimensional data set(s); (3) Determining one or more axes or planes of orientation of a device to be constructed for use in facilitating the surgical procedure(s) to be performed on the patient; (4) Modeling the device for use in facilitating the surgical procedure(s) using the determined axes and accounting for any other constraints derived from the converted data set(s); (5) Generating a prototype of the modeled device by, for example, use of rapid prototyping machinery; and (6) Preparing the prototype for use during the surgical procedure(s).

According to this aspect described above, the method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc.

According to yet another aspect of the present disclosure, the system and method includes use of data obtained from a radiographic imaging machine, a fluoroscopy, an ultrasonic machine or a nuclear medicine scanning device.

In another aspect, the patient-matching features may be confirmed by one or more additional process, such as fluoroscopy or other processes known to those of skill in the art.

In one aspect of the present disclosure, the method comprises the use of bone density data obtained through a CT scan of the patient anatomy for use in planning the trajectory of a surgical guide and corresponding fixation device or instrument, such as a cutting/routing/drilling instrument intended to penetrate the boney anatomy. This data may be used in other manners contemplated and described herein to assist the surgeon in planning, visualizing or otherwise preparing for the surgical procedure for the patient.

In yet another alternative embodiment, the data obtained from one of the scanning devices described above may be supplemented or merged with data from a bone density scanner to fabricate a device that is designed to remain in the patient after the surgical procedure is completed. It is to be expressly understood that data from a bone density scanner is not necessary to practice the inventions described herein, but may supplement the data and assist a surgeon or other medical professional in determining the proper location, trajectory, orientation or alignment of the various apparatus described herein.

According to yet another aspect of the present disclosure, data may be supplemented or merged with data from a bone density scanner to achieve further control over the orientation of any desired axes, particularly where the surgical procedure involves insertion of one or more implantable devices.

According to yet another embodiment, the data obtained from the patient permits the apparatus to be manufactured with defined pathways through the apparatus, which are operatively associated with at least one tool, instrument, or implant, and which permit the at least one tool, instrument or implant to be inserted in the defined pathways in a consistent and reproducible manner. Examples of devices that are implanted or remain in the patient include anchoring devices such as screws, pins, clips, hooks, etc., and implantable devices such as spacers, replacement joints, replacement systems, cages, etc.

According to yet another aspect of the present disclosure, a preconfigured surgical template is disclosed, which comprises one or more guides for receiving at least one tool. According to this embodiment, the one or more guides further comprise patient-contacting surfaces formed to be substantially congruent with the anatomical features of a patient. The preconfigured surgical template is configured such that the patient-contacting surfaces are configured to contact the plurality of anatomical features in a mating engagement, to ensure proper alignment and mounting of the guide or template, and the guides of the preconfigured surgical template are oriented in a direction selected prior to manufacturing of the preconfigured surgical template to achieve desired positioning, aligning or advancing of a tool within the one or more guides.

According to yet another aspect of the present disclosure, a method for creating a template for use in a surgical operation is disclosed. The method includes, but is not limited to: (1) collecting data from the patient corresponding to the patient's unique anatomy; (2) creating a model of the template from the data collected, the model comprising a plurality of matching surfaces to the patient's unique anatomy; (3) providing data associated with model to fabrication machinery; (4) rapidly generating the template to comprise the plurality of matching surfaces and further comprising at least one additional matching surface corresponding to at least one tool or instrument used in the surgical operation; and (5) generating a permanent device based on the template for use in the surgical operation.

In one embodiment of the present disclosure the model is a digital model. In another embodiment of the present disclosure the model is a physical model.

According to yet another aspect of the present disclosure, a system for performing a surgical procedure on a patient is disclosed, comprising:

a surgical guide;

the surgical guide comprising a plurality of surfaces determined from data scanned from the patient, the plurality of surfaces configured to match the patient's boney anatomy;

the surgical guide further comprising at least one trajectory or path determined from the patient's boney anatomy for facilitating the surgical procedure;

the surgical guide further comprising at least one sleeve, the sleeve comprised of a conductive material and having a first end and a second end;

an instrument comprising at least a first portion comprised of a conductive material and adapted to be received within the at least one sleeve by inserting the at least a first portion in the first end of the at least one sleeve and contact the conductive material of the at least one sleeve;

wherein the at least a first portion of the instrument is adapted to pass through the at least one sleeve and exit the second end of the at least one sleeve; and wherein the surgical guide may be subject to an electrical current for providing intra-operative monitoring (IOM) of the instrument during contact with the surgical guide and with the patient anatomy.

Another aspect of the present invention is a system and method of configuring a rod for use in a surgical procedure. The method includes the steps of, but is not limited to: (1) obtaining data associated with a patient's anatomy; (2) converting the data into a digital model; (3) determining trajectories for a plurality of fixation devices to be used in the surgical procedure; (4) modeling the rod based on the trajectories of the fixation devices; and (5) forming the rod by a rapid prototyping fabrication machine. The rod produced according to the method has a patient-specific shape adapted to substantially align with each of the fixation devices. Optionally, the method may further comprise re-shaping the rod to alter an amount of correction the rod is adapted to provide to the patient's anatomy.

In one embodiment, the method further comprises preparing a template. In one embodiment, the template has a void that forms a negative of the patient-specific shape of the rod. In another embodiment, the template comprises a predetermined portion of the patient's anatomy and includes fixtures adapted to releasably interconnect pegs for to the template. Each peg is adapted to model a trajectory of one of the fixation devices. In one embodiment, the pegs are adapted to retain the rod in an orientation to be used in the surgical procedure.

It is another aspect of the present invention to provide a patient-specific guide for use in a surgical procedure. The guide includes, but is not limited to: (1) a medial body having a proximal portion and a distal portion; (2) a first cannula and a second cannula, each of the cannulae with proximal and distal portions, at least one of the first cannula and the second cannula further comprising a bore oriented in a direction determined from the anatomical features of a patient, the bore adapted to guide an instrument or a fixation device in a cortical bone trajectory; and (3) a surface of one or more of the medial body, the first cannula, and the second cannula including patient-specific contours determined from the patient's anatomy and configured to contact and substantially conform to at least a first subcutaneous anatomic feature of a vertebra of the patient. In one embodiment, each of the first and second cannulae include a bore. The bores may have the same, or different, diameters. In another embodiment, only one of the first and second cannulae include a bore.

The guide may further comprise a leg extending from at least one of the first and second cannulae, the leg including a second surface including patient-specific contours determined from the patient's anatomy and configured to contact and substantially conform to a second anatomic feature of the patient. Additionally, the medial body may optionally include at least one leg extending from the medial body, the at least one leg including a second surface including patient-specific contours determined from the patient's anatomy and configured to contact and substantially conform to a second anatomic feature of the patient.

In one embodiment, the surface with the patient-specific contours is adapted to hook at least partially around vertebral anatomy selected from the group consisting of: a lamina, a pars interarticularis, an aspect of a transverse process, a spinous process, an inferior articular process, and a superior articular process. In another embodiment, at least a portion of the guide is shaped to prevent contact with a portion of the patient's anatomy.

In another embodiment, the guide includes at least a third cannula having a bore that is oriented in a direction determined from the anatomical features of the patient, the bore adapted to guide an instrument or a fixation device. In another embodiment, the bore of the third cannulae is directed in a trajectory that is not parallel to the bore of the at least one of the first and second cannulae. In still another embodiment, the third cannulae is configured to target a predetermined portion of a different vertebrae of the patient. Optionally, the third cannulae is releasably interconnected to the guide. In another embodiment, the third cannulae includes a track having patient-specific depth control, angle, and orientation adapted to guide an instrument operable to remove a predetermined portion of the vertebrae. In one embodiment, the track is oriented to guide the instrument to target facet capsules of an adjacent vertebrae. In another embodiment, the track is adapted to target a pedicle of the vertebrae.

In one embodiment, a cutting guide is interconnected to a portion of the guide. The cutting guide includes a track adapted to guide an instrument operable to remove, or alter, a predetermined portion of the vertebrae of the patient. In one embodiment, the track of the cutting guide includes patient-specific depth, angle, and orientation control to guide the instrument.

In still another embodiment, the medial body of the guide comprises a first portion releasably interconnected to a second portion.

In another aspect of the present invention, a patient-specific guide for use in a surgical procedure is provided. The guide is adapted to contact, or fit on, a predetermined portion of a vertebra of a patient and generally comprises: (1) a body with a proximal portion and a distal portion, the body having at least one of a bore and a track oriented in a predetermined trajectory determined from anatomical features of the patient, the bore or track adapted to guide an instrument or a fixation device; and (2) at least two legs extending from the body, a portion of each leg comprising patient-specific contours determined from the patient's anatomy and configured to contact and substantially conform to at least a first subcutaneous anatomic feature of the vertebra of the patient. In one embodiment, the bore is directed in a pedicle screw trajectory. In another embodiment, the bore is directed in a cortical bone trajectory. In still another embodiment, the body further comprises a second bore that is oriented in a direction for placement of a temporary fixation device.

Optionally, the body may comprise at least two portions. In one embodiment, the portions of the body are adapted to be interconnected together.

In one embodiment, at least a portion of one of the legs is adapted to hook at least partially around, and substantially conform to, a second anatomic feature of the patient. In one embodiment at least one of the legs is adapted to contact a portion of the patient's anatomy that has been altered by a surgical procedure. In another embodiment, at least one of the legs is adapted to contact an unaltered portion of the patient's anatomy.

The track includes patient-specific depth control, angle, and orientation adapted to guide an instrument operable to remove a predetermined portion of the vertebrae. In one embodiment, the track is formed through a portion of the body. In another embodiment, the track is formed by a portion of an exterior surface of the body. The portion of the exterior surface may comprise a substantially planar surface against which a portion of the instrument may move in a predetermined plane.

In one embodiment, the guide further comprises a frame. The frame is configured to be fixed to screws placed in at least one vertebrae of the patient. The body of the guide is adapted to releasably interconnect to the frame. In this manner, the guide may be used before, or after, a guide of another embodiment of the present invention used in a surgical procedure.

In still another embodiment, the guide includes a second bore. The second bore may be oriented in a trajectory that is not parallel to the other bore. In one embodiment, the bore is adapted to guide an instrument. In another embodiment, the bore is oriented in a direction for placement of a temporary fixation device.

In one aspect of the present invention a patient-specific template is provided. The template is adapted for use in a surgical procedure and includes, but is not limited to, a body having a proximal portion and a distal portion. The distal portion is shaped to substantially conform to a predetermined portion of a vertebrae of a patient. The body includes at least one of a bore and a track oriented in a direction determined from anatomical features of the patient. In one embodiment, the bore or track is adapted to guide an instrument or a fixation device.

A portion of the body is adapted to hook at least partially around, and substantially conform to, at least a second predetermined portion of the vertebrae of the patient. In one embodiment, the hook portion of the body comprises an extension of the distal portion of the body. In another embodiment, the extension of the body is designed to hook at least partially around vertebral anatomy selected from the group consisting of: a lamina, a pars interarticularis, an aspect of a transverse process, a spinous process, an inferior articular process, and a superior articular process.

In one embodiment, the distal portion of the body of the template is shaped to substantially conform to cut surfaces generated by removal of a portion of the patient's vertebrae. The portion of the patient's vertebrae may be removed during a previous portion of the same surgical procedure. In another embodiment, at least a portion of the distal portion is shaped to substantially conform to an unaltered portion of the patient's anatomy.

In one embodiment, the bore is directed in a cortical bone trajectory. In another embodiment, the bore is directed in a pedicle screw trajectory.

In one embodiment, a cannulae is associated with the body. The cannulae includes a bore that is oriented in a direction for placement of a temporary fixation device. Optionally, the body may further comprise a second bore.

In another embodiment, the body further comprises at least one track. The track includes patient-specific depth control, angle, and orientation adapted to guide an instrument operable to remove a predetermined portion of the vertebrae. In one embodiment, the at least one track comprises two tracks formed in the body.

In one embodiment, the template further includes a frame configured to be fixed to screws placed in at least one vertebrae of the patient. The body of the template is adapted to releasably interconnect to the frame. In this manner, the template may be used in a surgical procedure before, or after, a different guide or template of the present invention.

Further aspects of the present disclosure are directed to the system described above and further comprising a surgical guide which is subject to an electrical current by providing at least one electrode on the conductive material of the surgical guide and providing electrical current to the at least one electrode.

Further aspects of the present disclosure provide a method for manufacturing a surgical guide at an off-site manufacturing location, an on-site manufacturing location, a clinic, a surgery center, a surgeon's offices, a public hospital or at a private hospital.

Still further aspects of the present disclosure include a surgical guide manufactured using one of the methods described herein, wherein the guide is manufactured by a process selected from the group consisting of a rapid prototyping machine, a stereolithography (SLA) machine, a selective laser sintering (SLS) machine, a selective heat sintering (SHM) machine, a fused deposition modeling (FDM) machine, a direct metal laser sintering (DMLS) machine, a powder bed printing (PP) machine, a digital light processing (DLP) machine, an inkjet photo resin machine, and an electron beam melting (EBM) machine.

Incorporated by reference in their entireties are the following U.S. patents and patent applications and international publications directed generally to methods and apparatus related to surgical procedures, thus providing written description support for various aspects of the present disclosure. The U.S. patents and pending applications incorporated by reference are as follows: U.S. Pat. Nos. 8,758,357, 8,419,740, 8,357,111, 8,298,237, 8,277,461, 8,257,083, 8,214,014, 8,206,396, 8,167,884, 8,159,753, 7,957,824, 7,844,356, 7,658,610, 7,623,902, 7,491,180, 7,235,076, 6,755,839, 6,711,432, 5,201,734, and 3,151,392, U.S. Design Pat. Nos. D705,929, D669,176, D672,038, D618,796, D606,195, D533,664, D532,515, D428,989, D420,132, D412,032, D403,066, and D359,557, and U.S. Pat. Pub. Nos. 2013/0123850, 2013/0053854, 2013/0218163, 2012/0215315, 2012/0179259, 2012/0130434, 2012/0041445, 2011/0319745, 2011/0288433, 2011/0224674, 2011/0218545, 2011/0213376, 2011/0190899, 2011/0184526, 2011/0184419, 2011/0166578, 2011/0160867, 2011/0160736, 2011/0093086, 2011/0093023, 2011/0071533, 2011/0054478, 2011/0046735, 2011/0015639, 2011/0015636, 2010/0324692, 2010/0305700, 2010/0217336, 2010/0217270, 2010/0191244, 2010/0152782, 2010/0100193, 2010/0087829, 2010/0082035, 2010/0049195, 2010/0016984, 2009/0270868, 2009/0254093, 2009/0198277, 2009/0187194, 2009/0138020, 2009/0110498, 2009/0099567, 2009/0093816, 2009/0088763, 2009/0088761, 2009/0088674, 2009/0087276, 2008/0319491, 2008/0312659, 2008/0275452, 2008/0257363, 2008/0183214, 2008/0161815, 2008/0114370, 2007/0288030, 2006/039266, 2006/0241385, 2006/0149375, 2006/0095044, 2006/0084986, 2005/0148843, 2004/0243481, and 2004/0097925. The international publications incorporated by reference are as follows: European Publication No. EP 2168507, and World Intellectual Property Organization Pub. Nos. WO 2013/104682, WO 2013/041618, WO 2012/152900, WO 2011/109260, WO 2011/106711, WO 2011/080260, WO 2011/041398, WO 2010/148103, WO 2010/033431, WO 2009/129063, WO 2008/027549, and WO 2007/145937, and Chinese Publication Nos. CN 201275138, CN 201404283, CN 101390773, and CN 101953713.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery. The embodiments also reduce the cumulative radiation exposure to both the surgeon and medical professionals in the operating environment and the patient.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation. Embodiments of the present disclosure may be designed such that the apparatus may be formed and verified, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. It is expressly understood for purposes of this disclosure that other types of machinery other than rapid prototyping machinery may be employed in the systems and methods described herein, for example, by computerized numerical control (CNC) machinery.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

In the drawings:

FIG. 1 is a perspective view of a three-dimensional model of a unique grouping of anatomical features from which a set of data points may be derived according to one embodiment of the present disclosure;

FIG. 2 is a flow chart diagram showing the various steps of performing a method of manufacturing and using an apparatus for facilitating a surgical procedure according to one embodiment of the present disclosure;

FIG. 3 is a perspective view of an apparatus according to yet another alternative embodiment of the present disclosure;

FIG. 4A is a perspective view of a cutting guide according to yet another alternative embodiment of the present disclosure;

FIG. 4B is a perspective view according to the embodiment shown in FIG. 4A;

FIG. 5A is a perspective view of a cutting tool according to yet another alternative embodiment of the present disclosure;

FIG. 5B is a detailed perspective view according to the embodiment shown in FIG. 5A;

FIG. 5C is another perspective view according to the embodiment shown in FIG. 5A depicted with the cutting guide of FIG. 4A;

FIG. 6A is yet another perspective view according to the embodiment shown in FIG. 5A depicted with the cutting guide of FIG. 4A;

FIG. 6B is another perspective view according to the embodiment shown in FIG. 5A depicted with the cutting guide of FIG. 4A;

FIG. 7A is a front elevation view of a guide of another embodiment of the present invention positioned against a vertebral body;

Figure 7B:
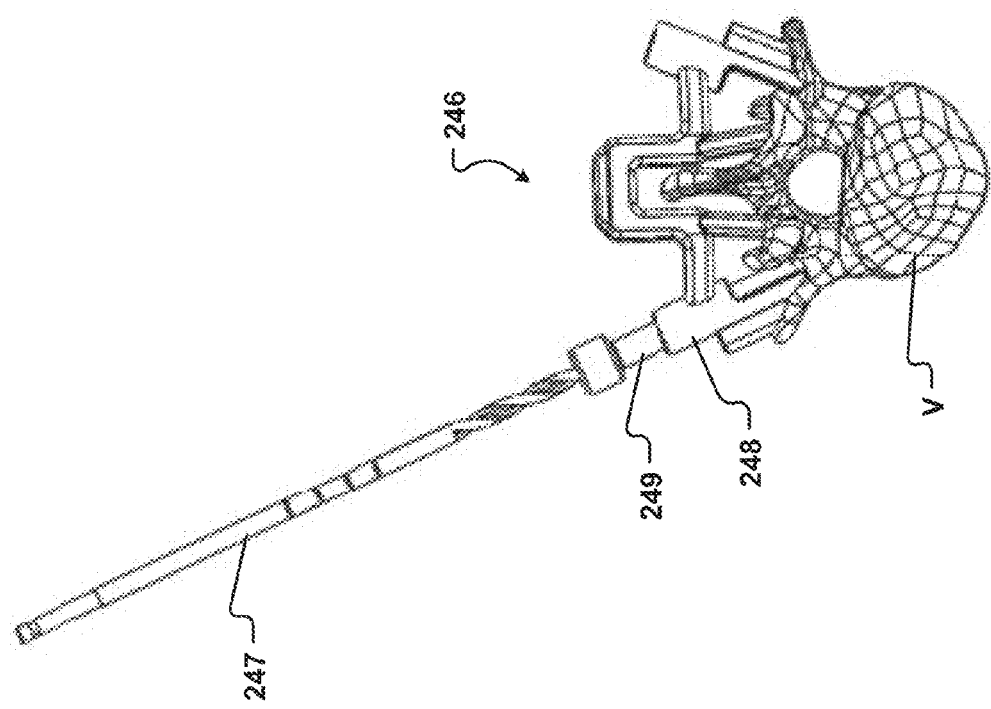
Figure 7A:
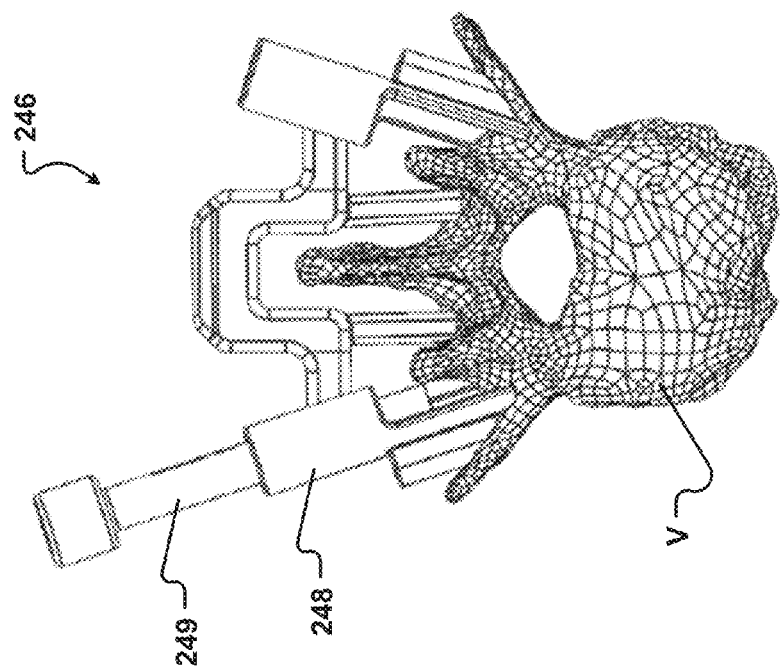
Figure 7D:
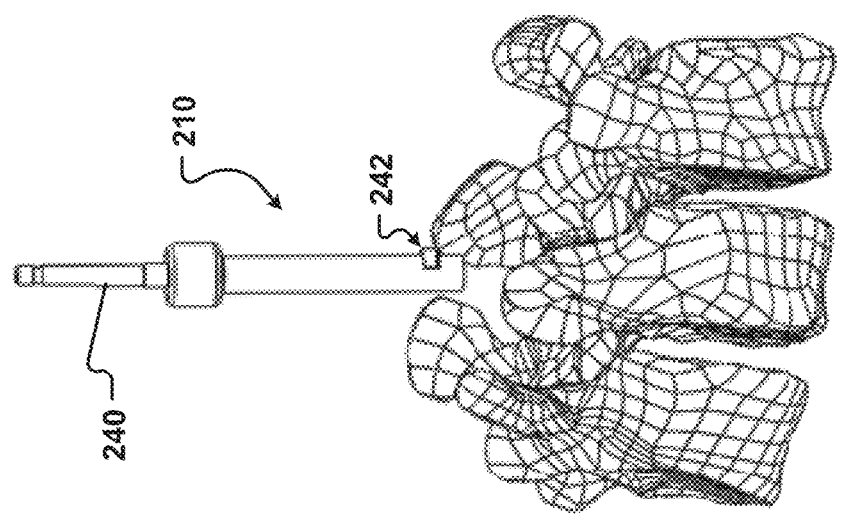
Figure 7C:
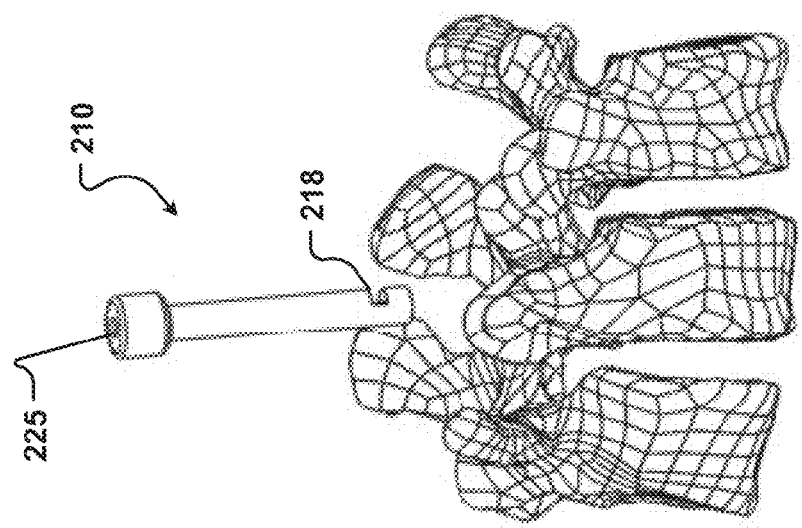
Figure 8D:
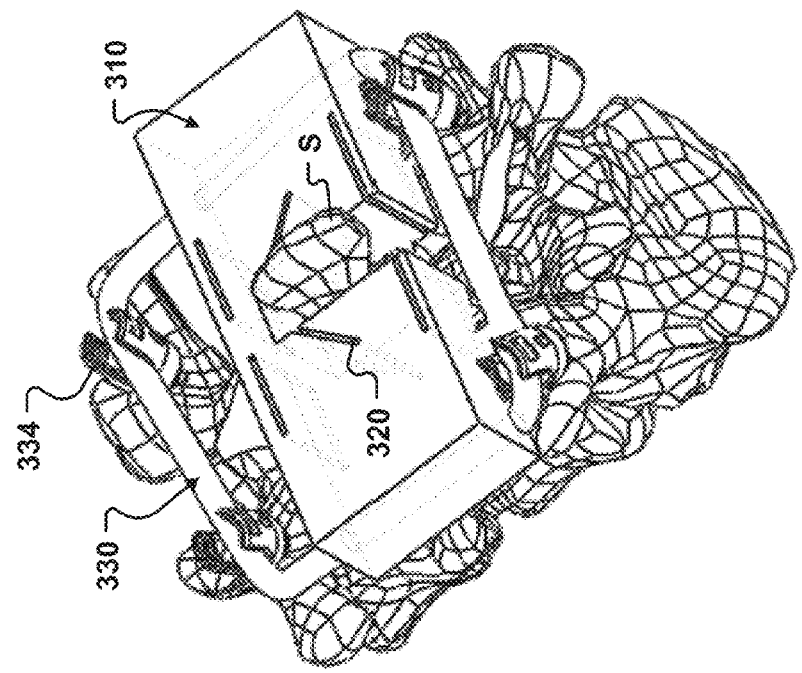
Figure 8C:
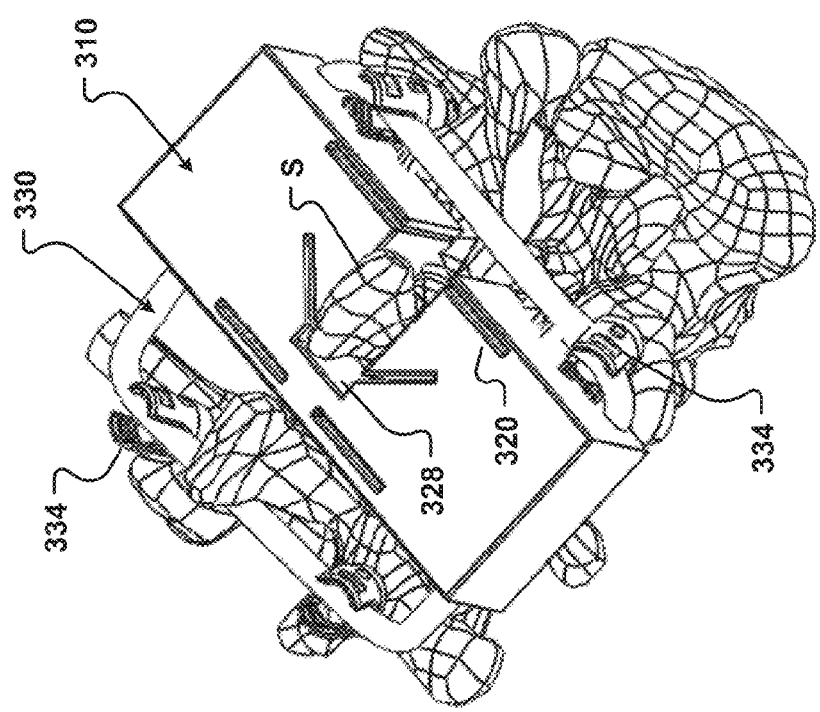
Figure 9D:
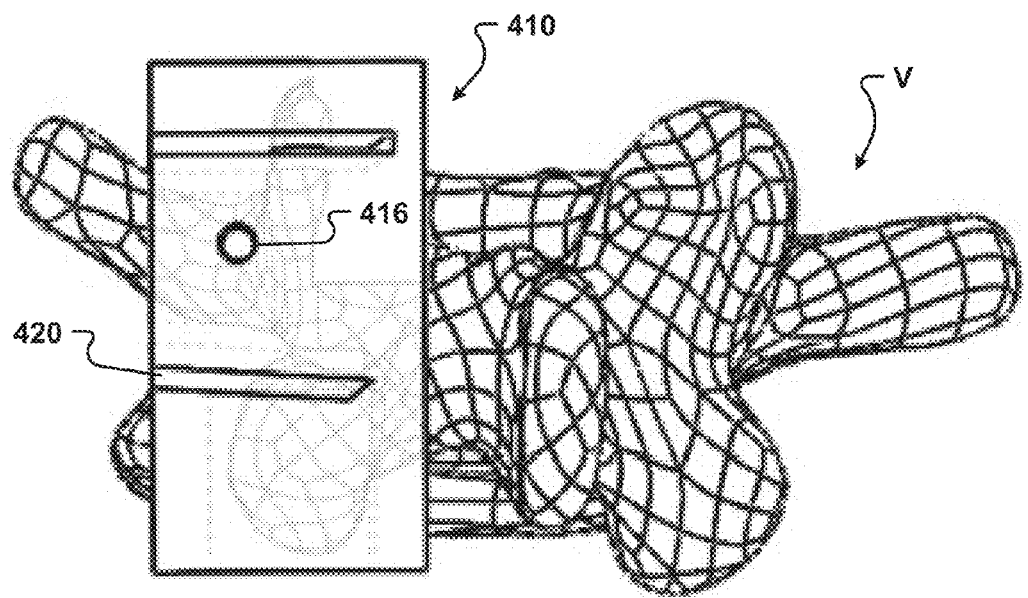
Figure 9E:
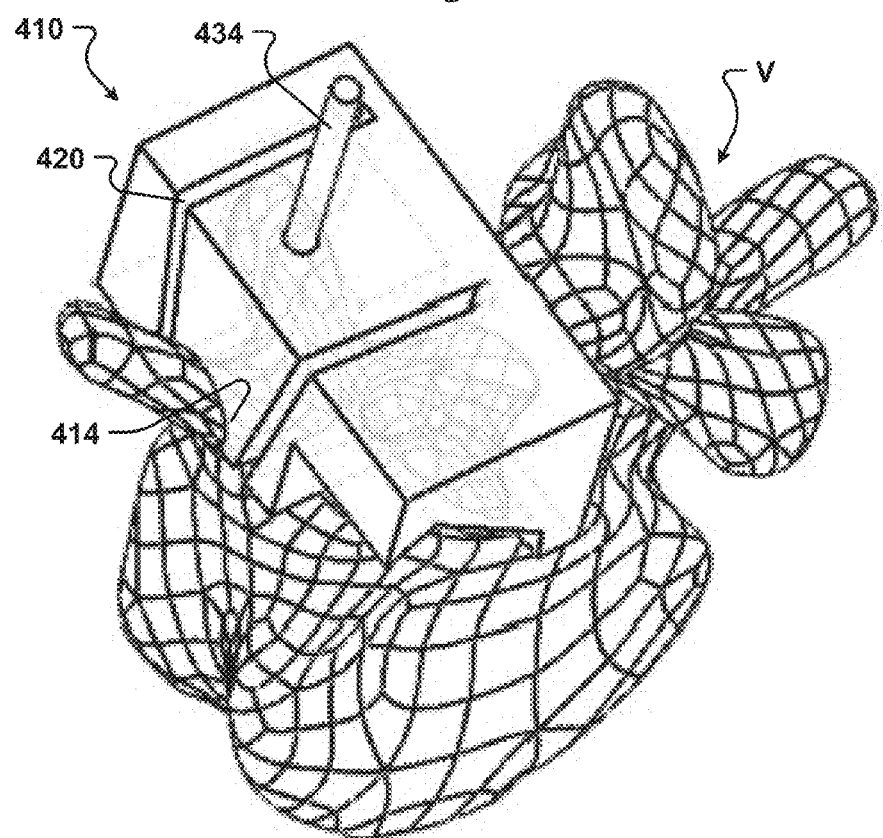
Figure 9G:
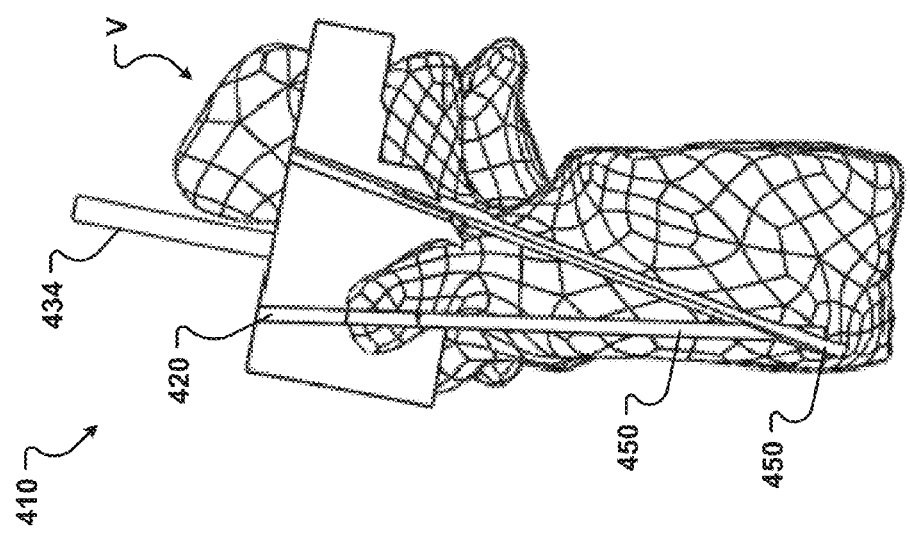
Figure 9F:
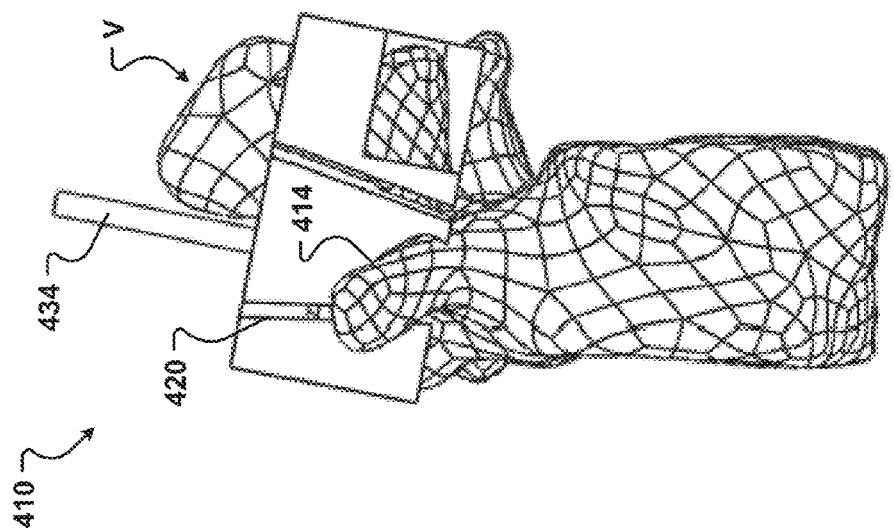
Figures 10A, 10B:
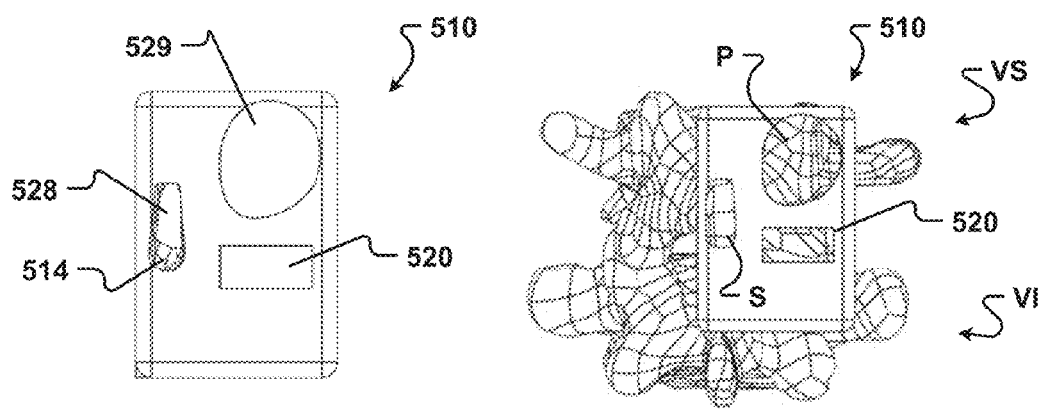
Figures 10C, 10D:
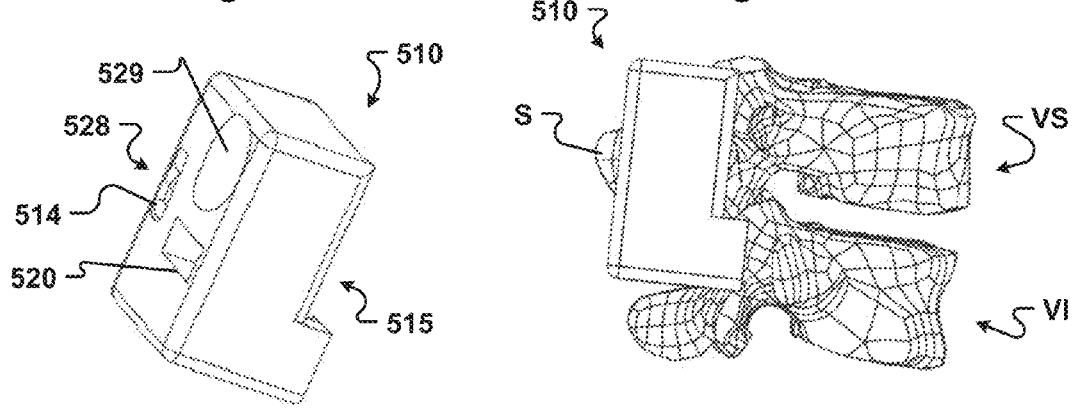
Figure 10E:
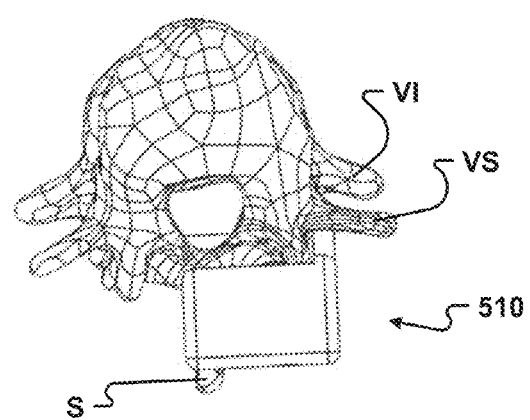
Figures 12A, 12B:
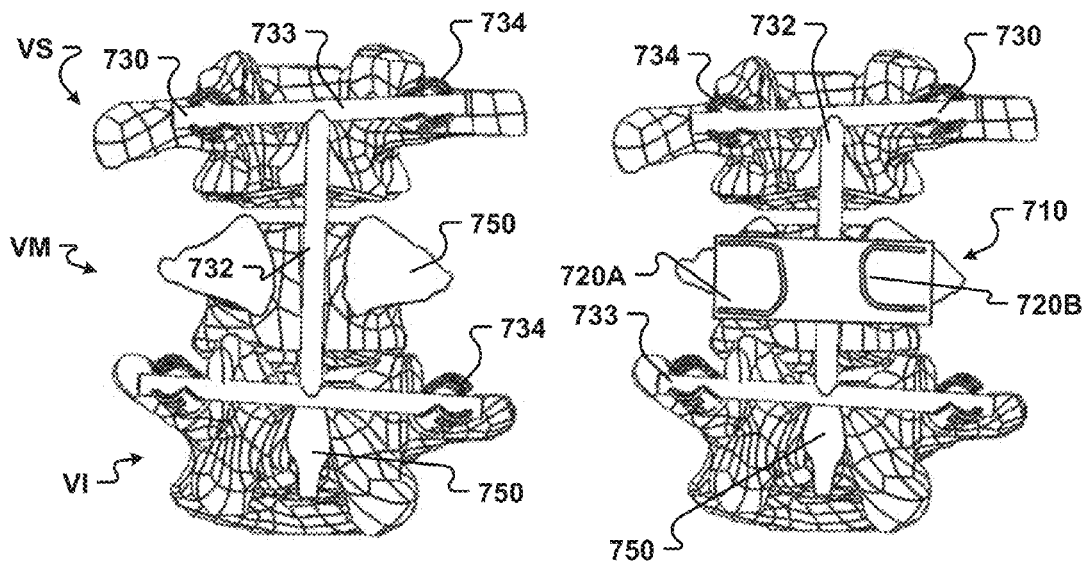
Figure 12C:
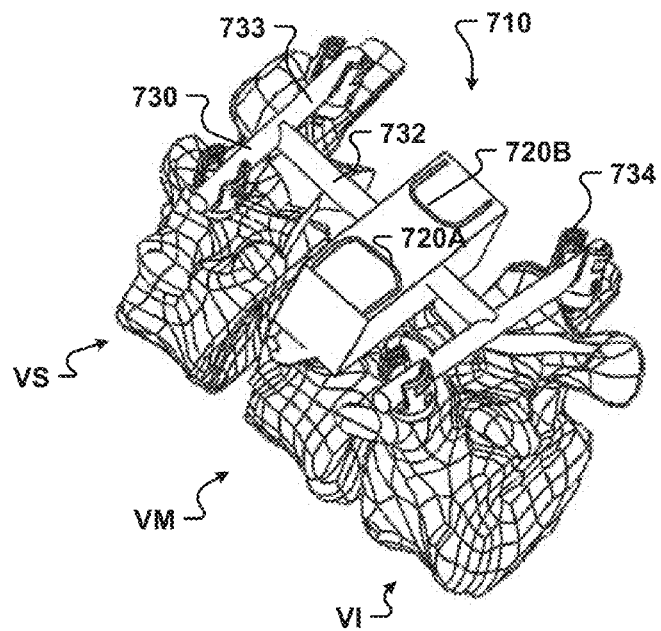
Figure 13E:
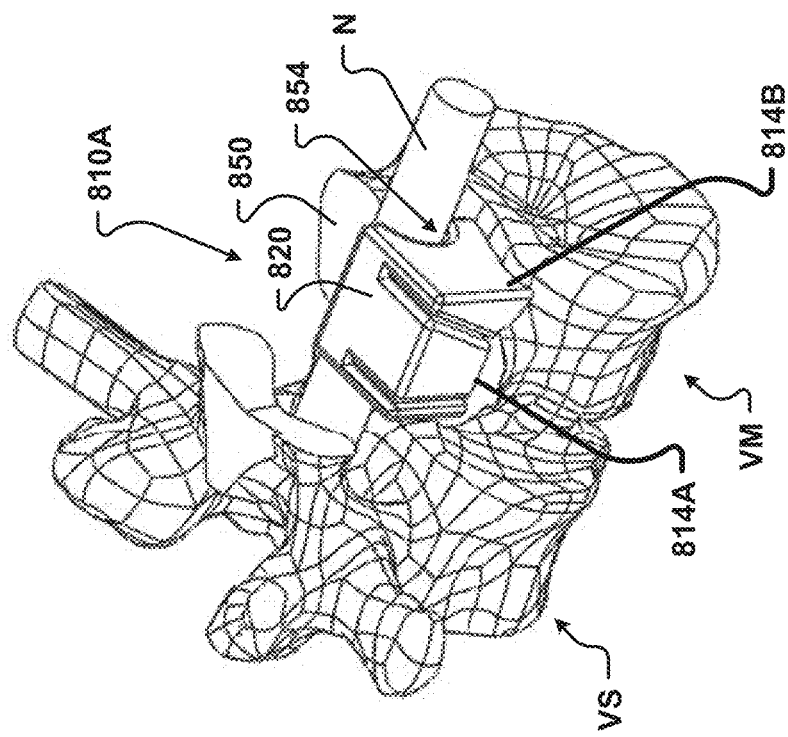
Figure 13D:
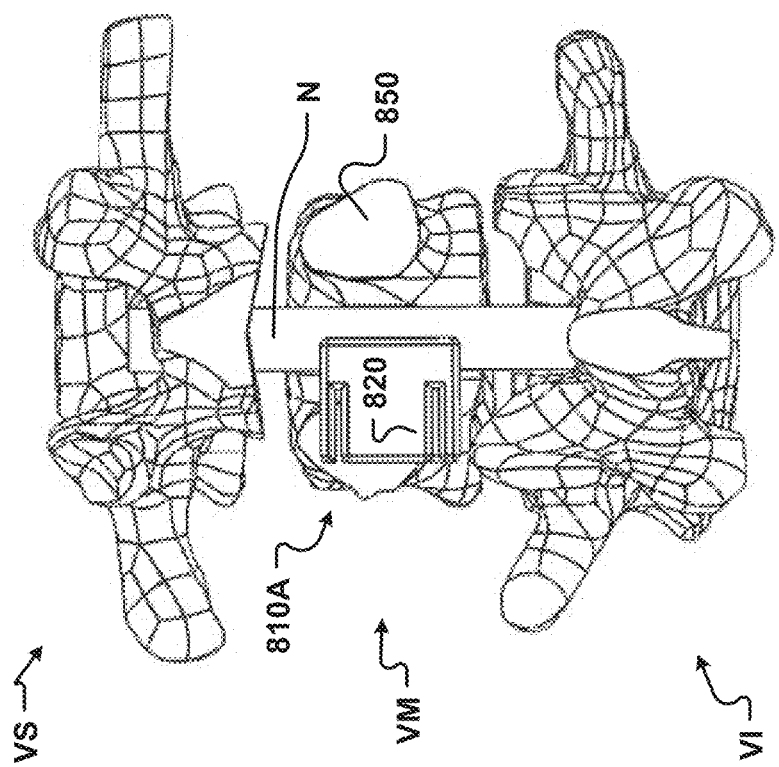
Figures 14A, 14B:
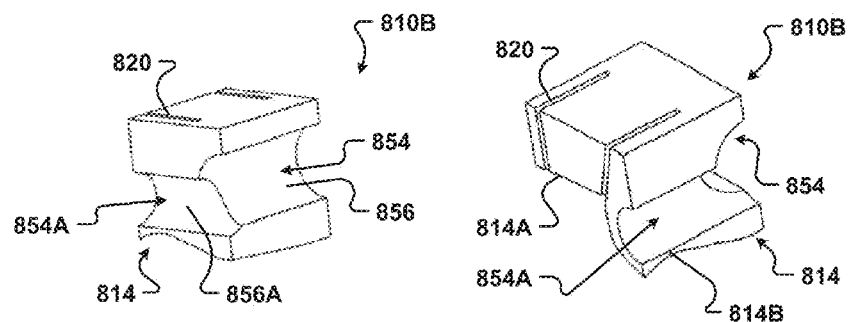
Figures 14C, 14D:
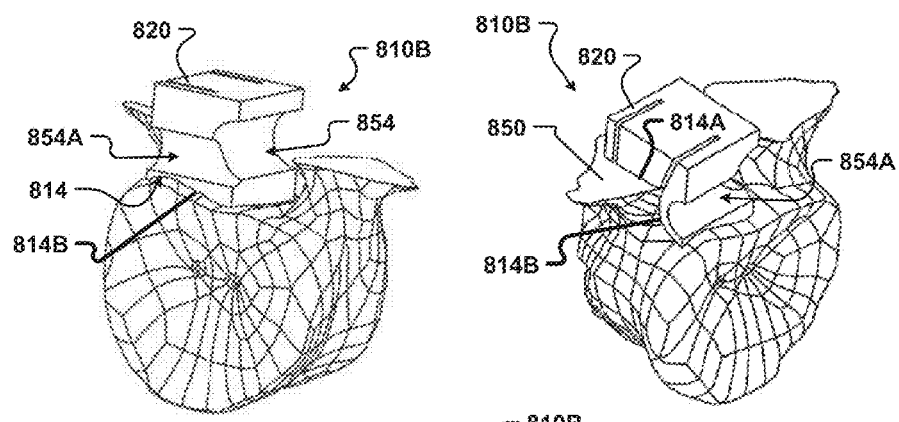
Figure 14E:
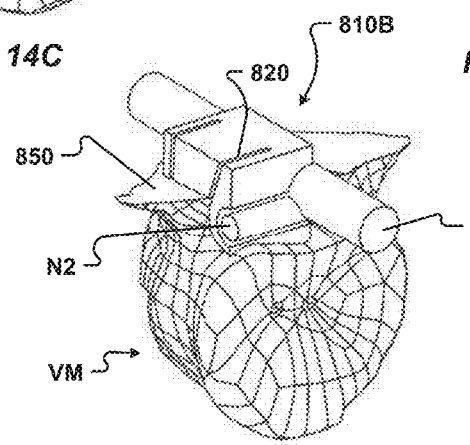
Figure 15C:
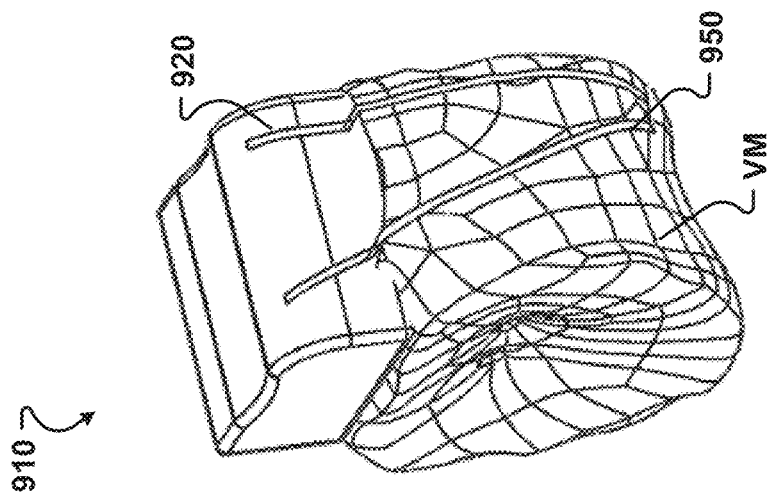
Figure 15B:
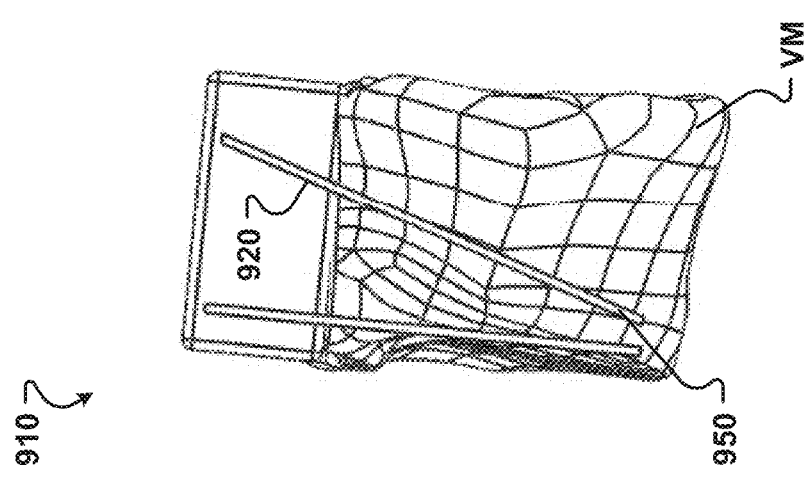
Figure 15A:
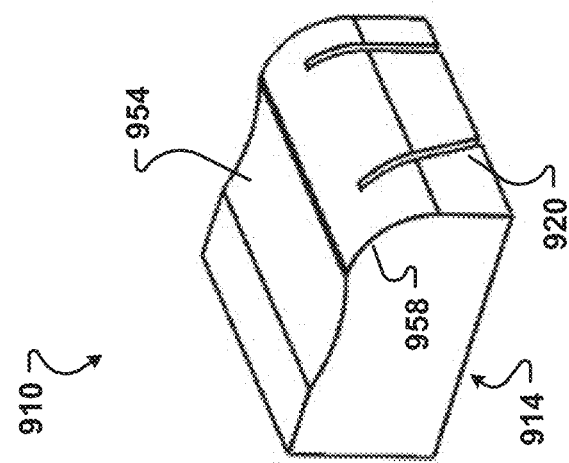
Figure 16A:
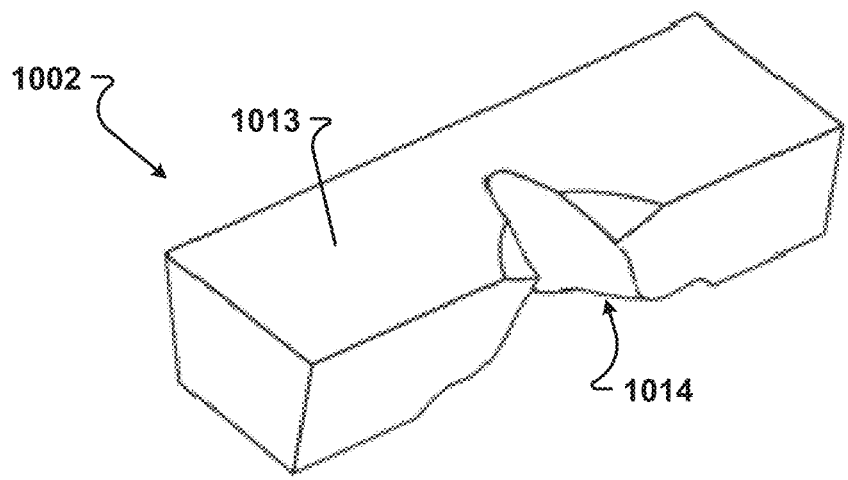
Figure 16B:
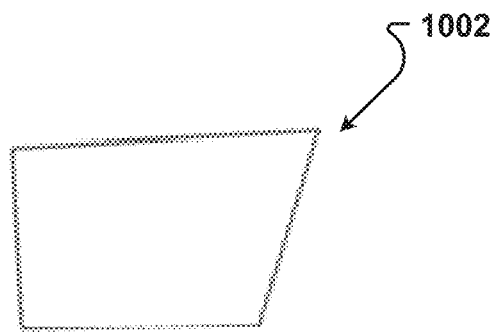
Figure 16C:
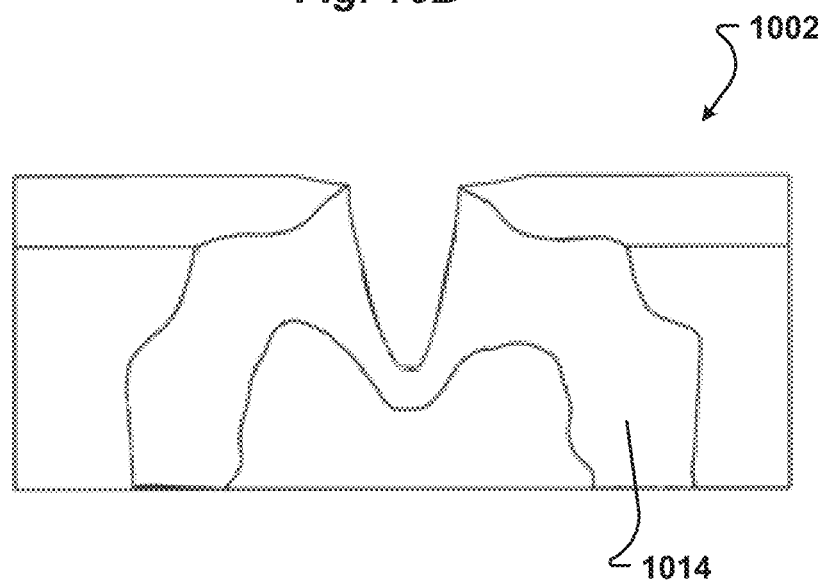
Figure 17A:
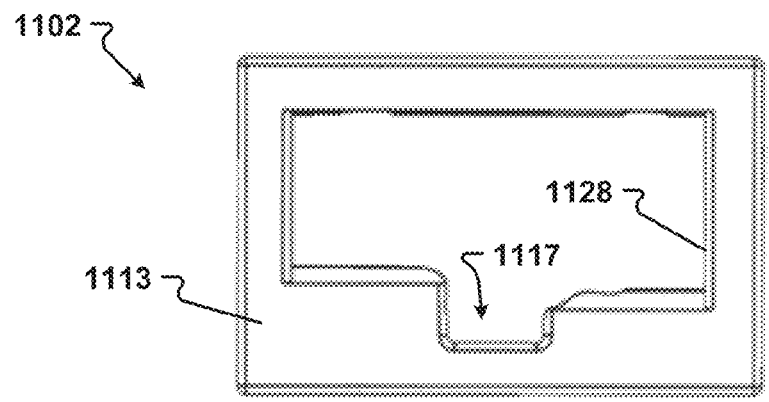
Figure 17B:
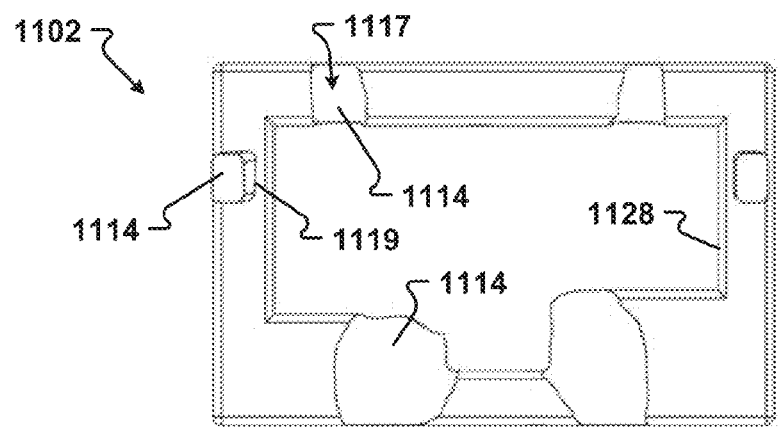
Figure 17C:
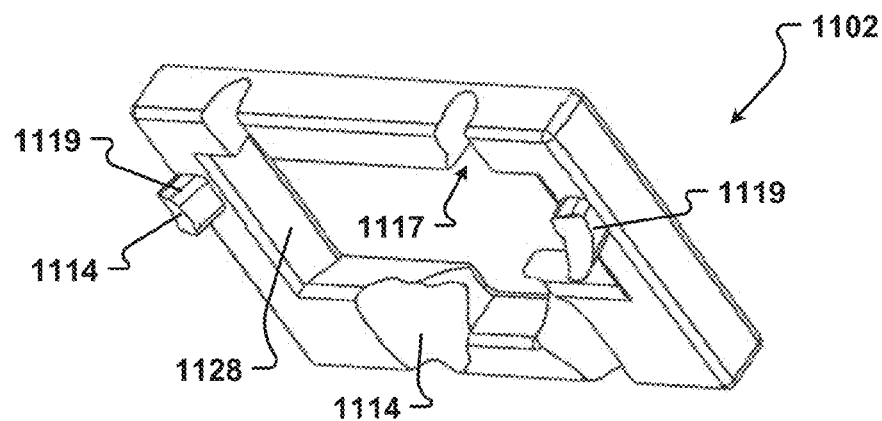
Figure 17D:
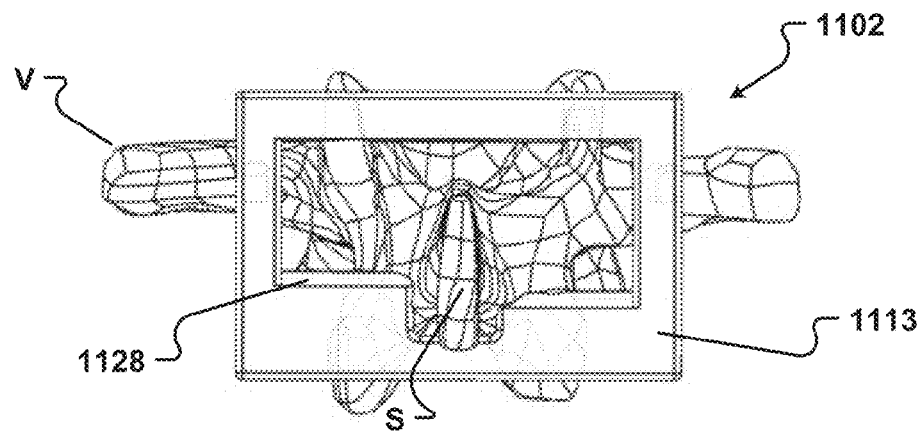
Figure 17E:
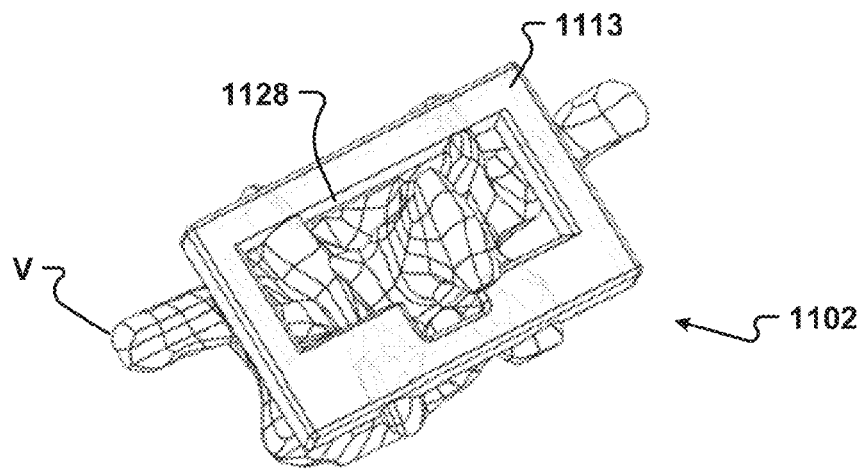
Figure 17F:
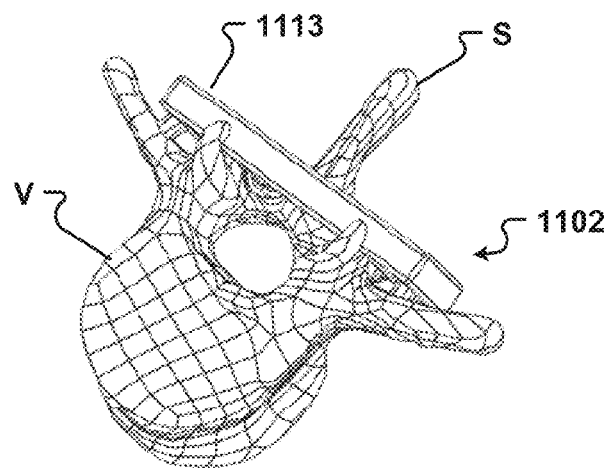
Figure 18A:
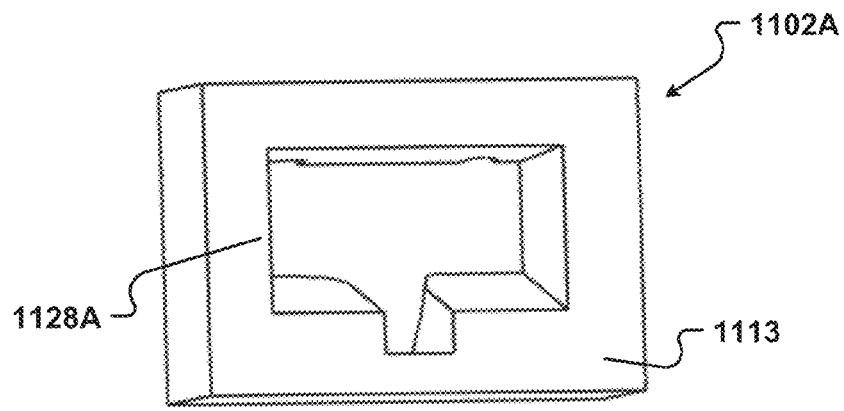
Figure 18B:
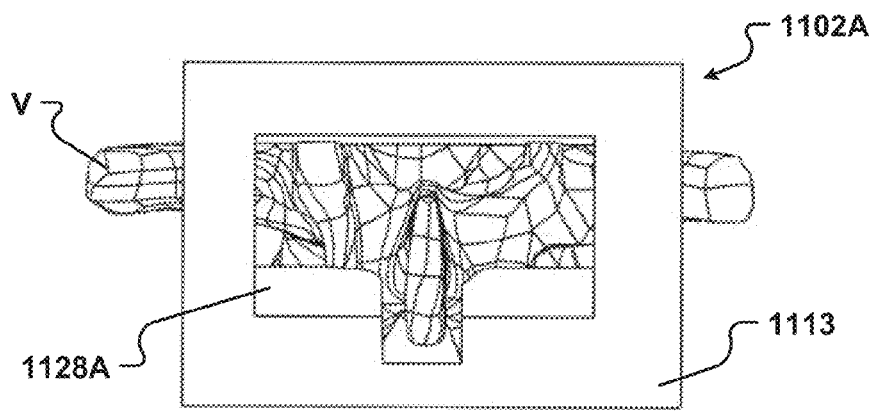
Figure 18C:
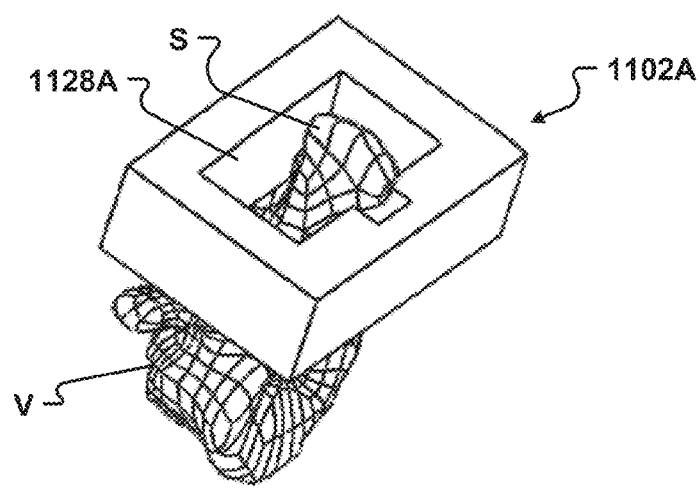
Figure 19A:
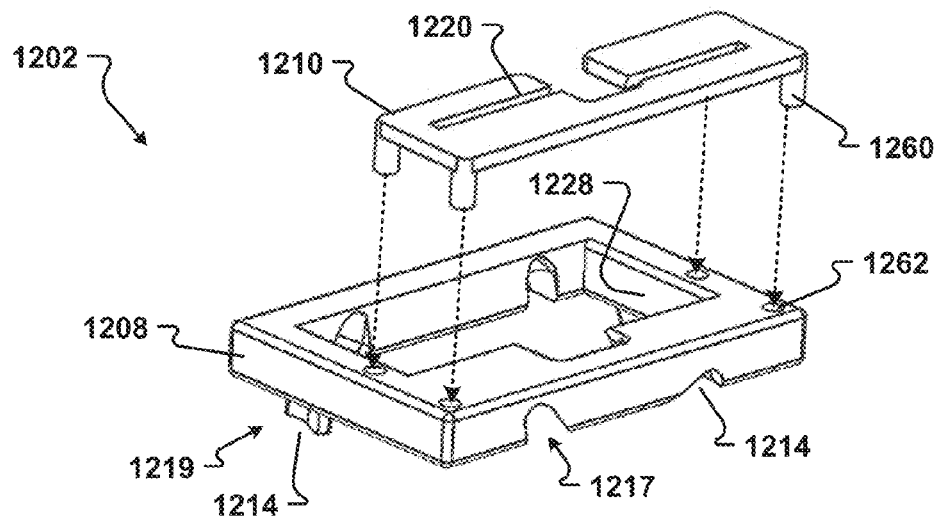
Figure 19B:
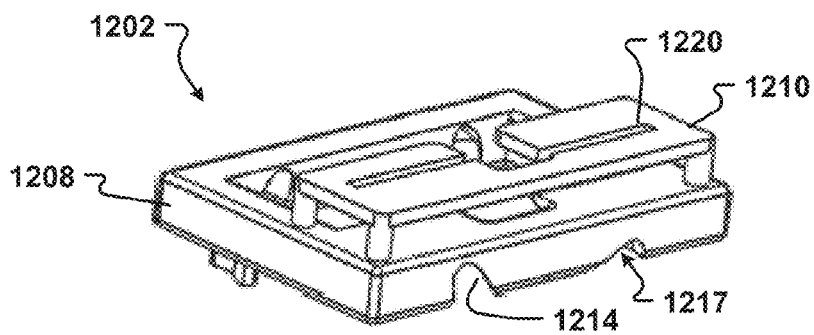
Figure 19C:
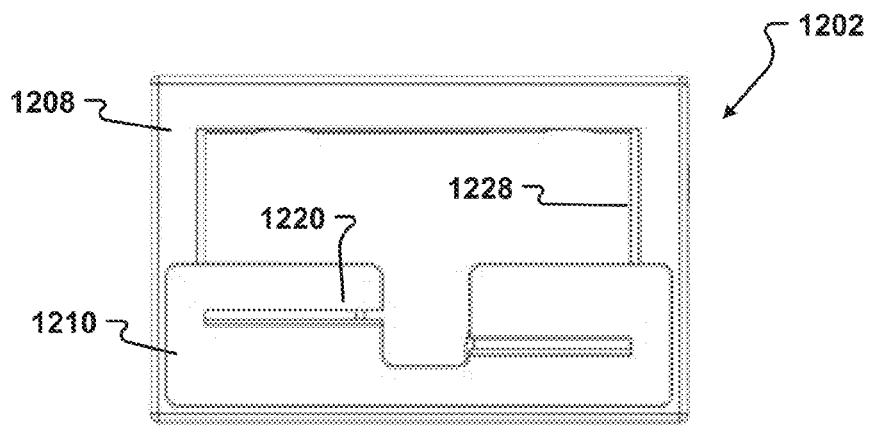
Figure 19D:
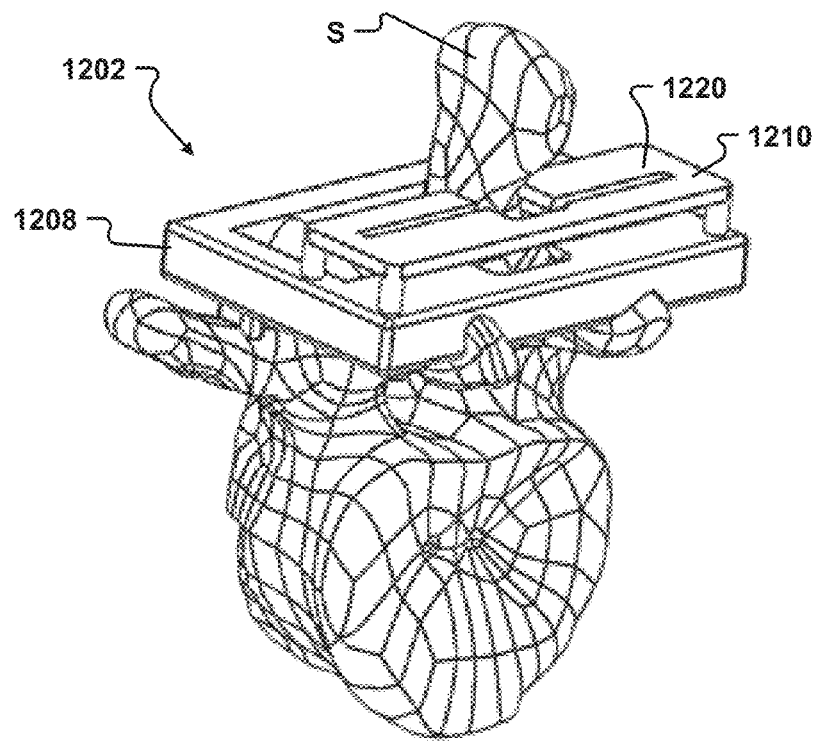
Figure 19E:
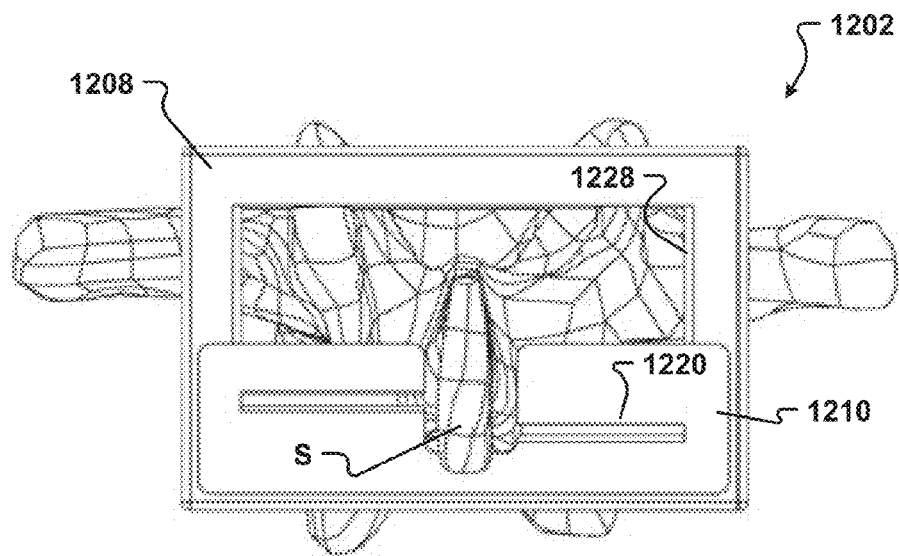
Figures 22E, 22F:
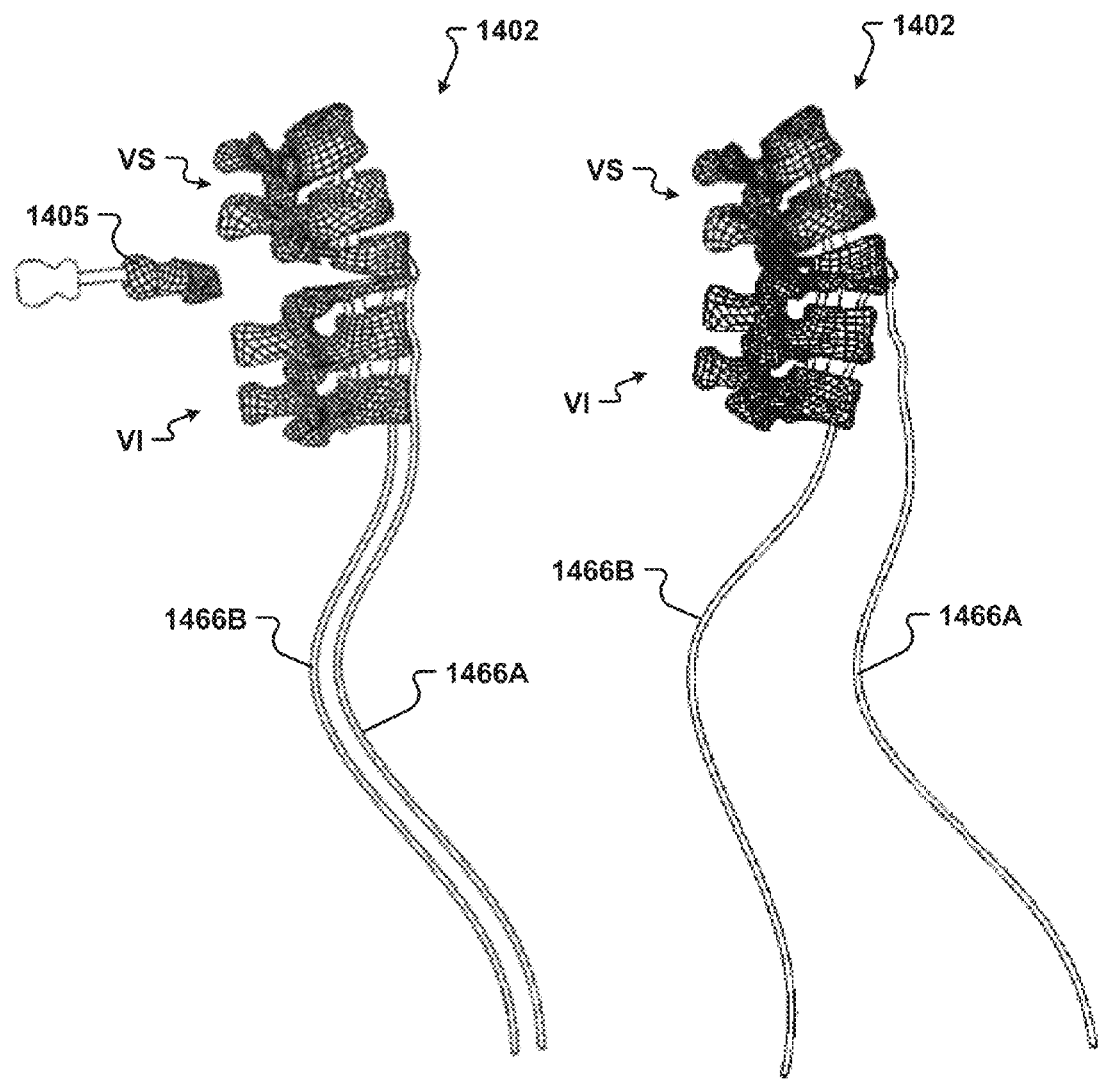
Figure 23A:
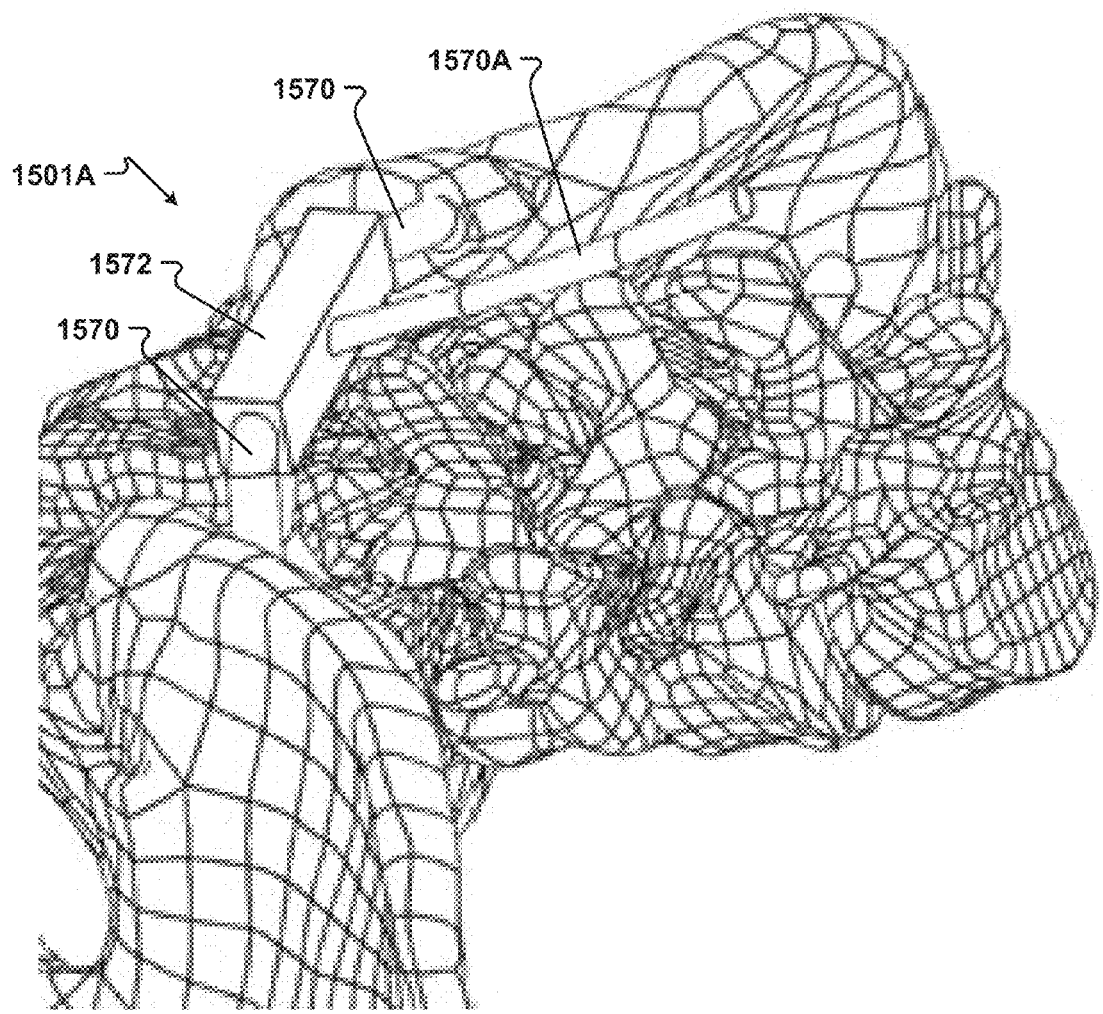
Figures 23B, 23C, 23D:
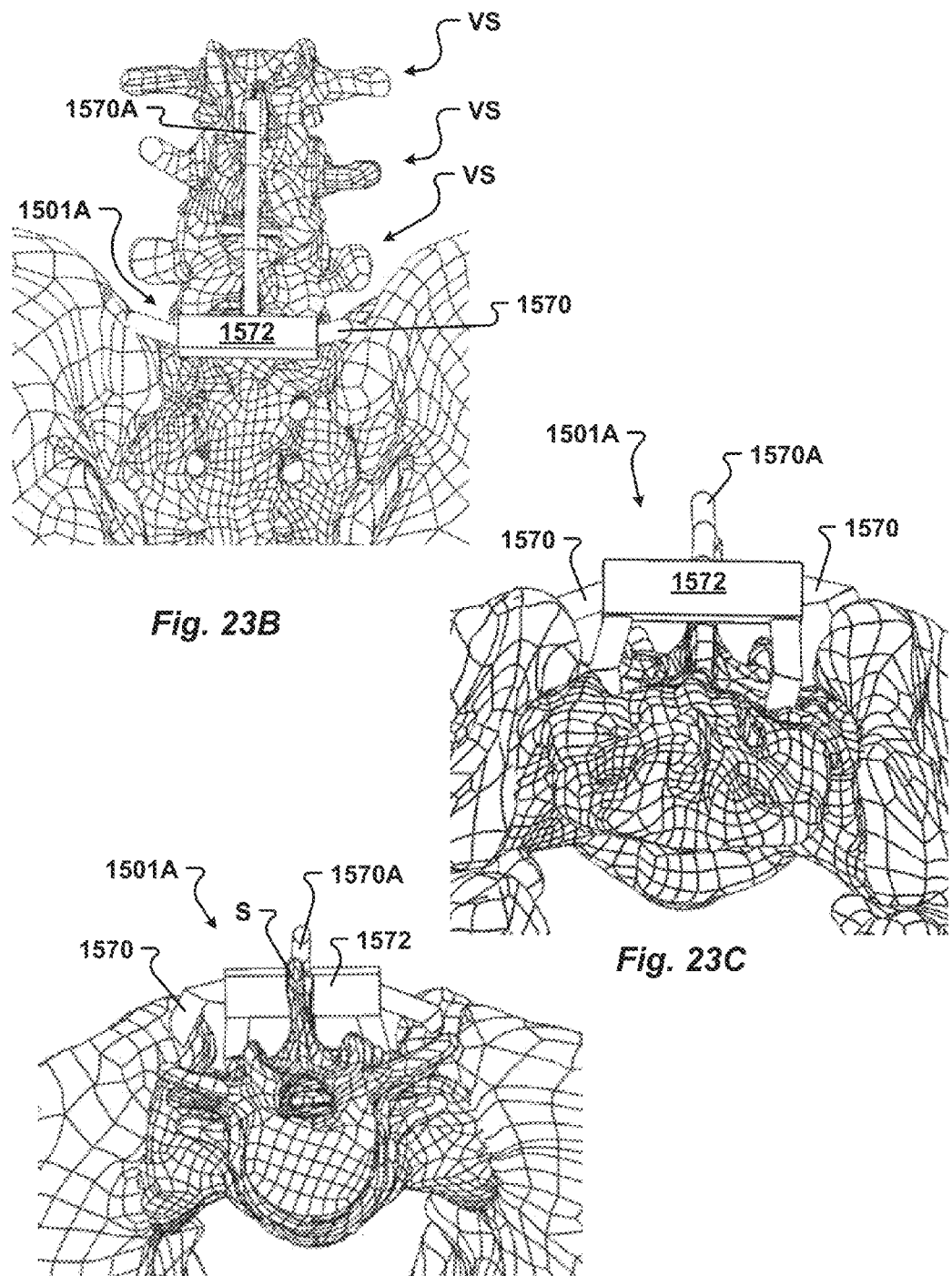
Figure 24A:
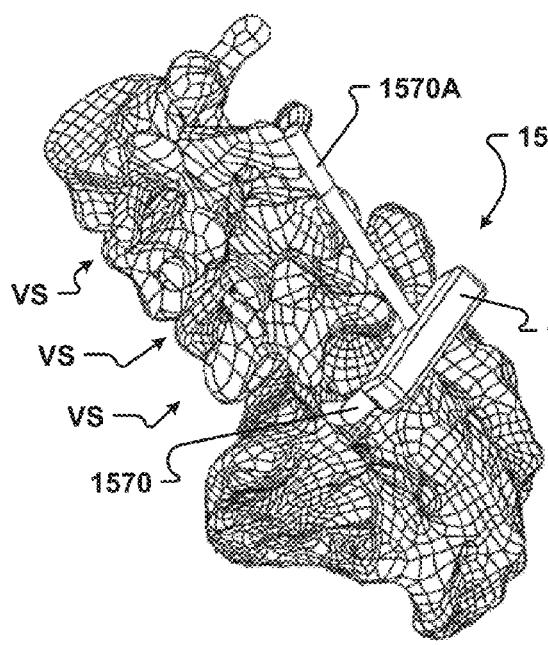
Figure 24B:
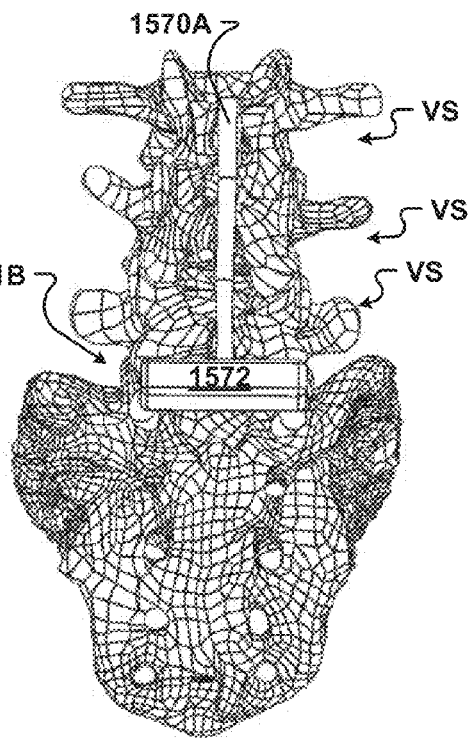
Figure 24C:
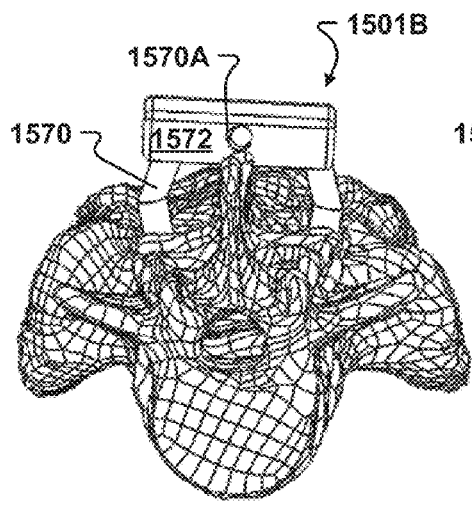
Figure 24D:
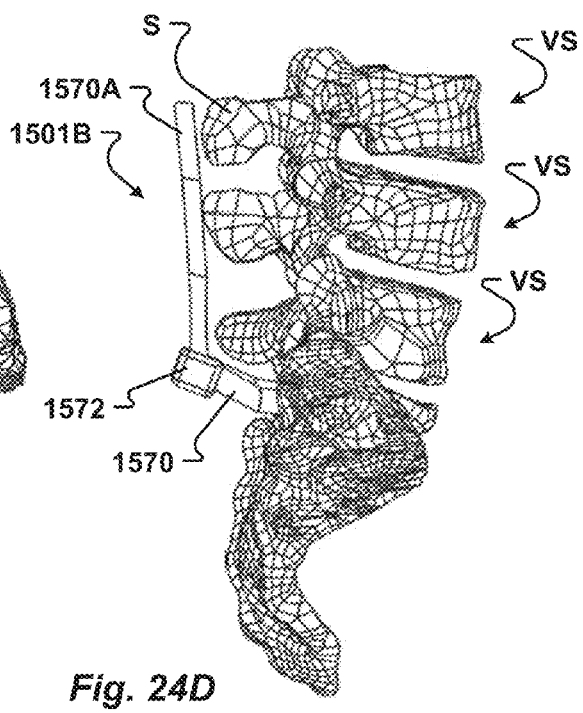
Figure 25A:
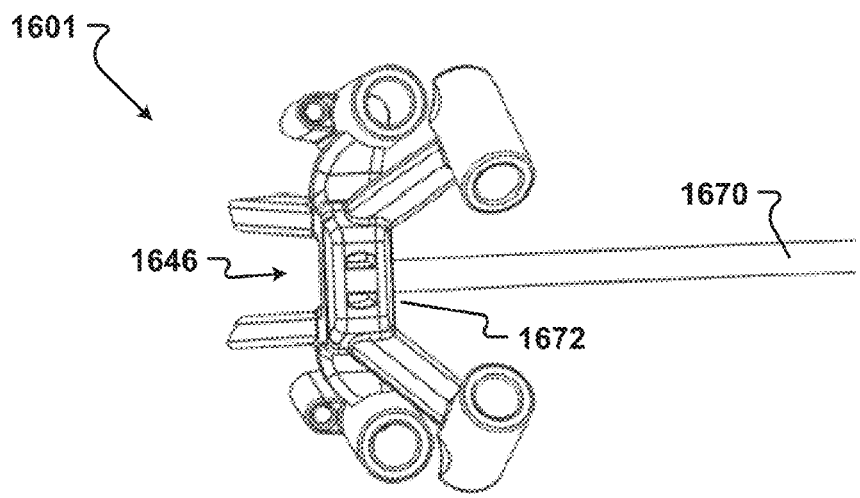
Figure 25B:
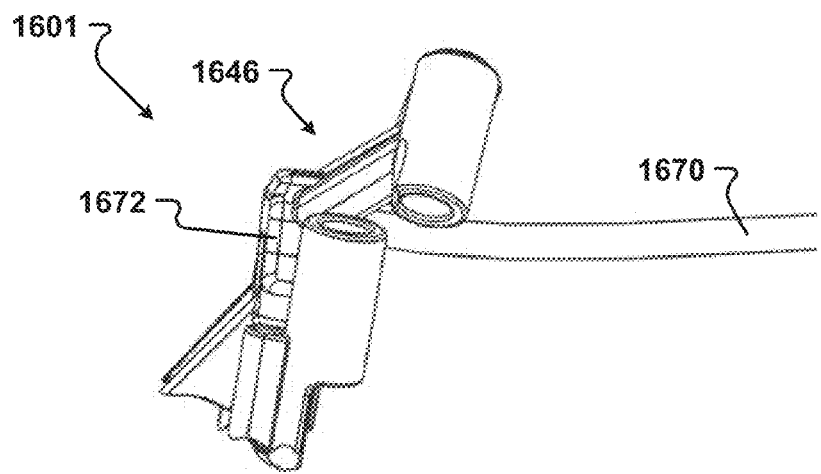
Figure 25C:
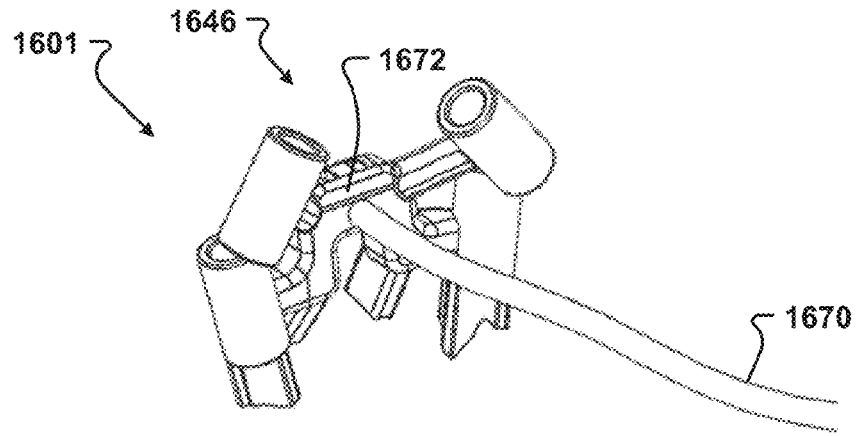
Figures 25D, 25E:
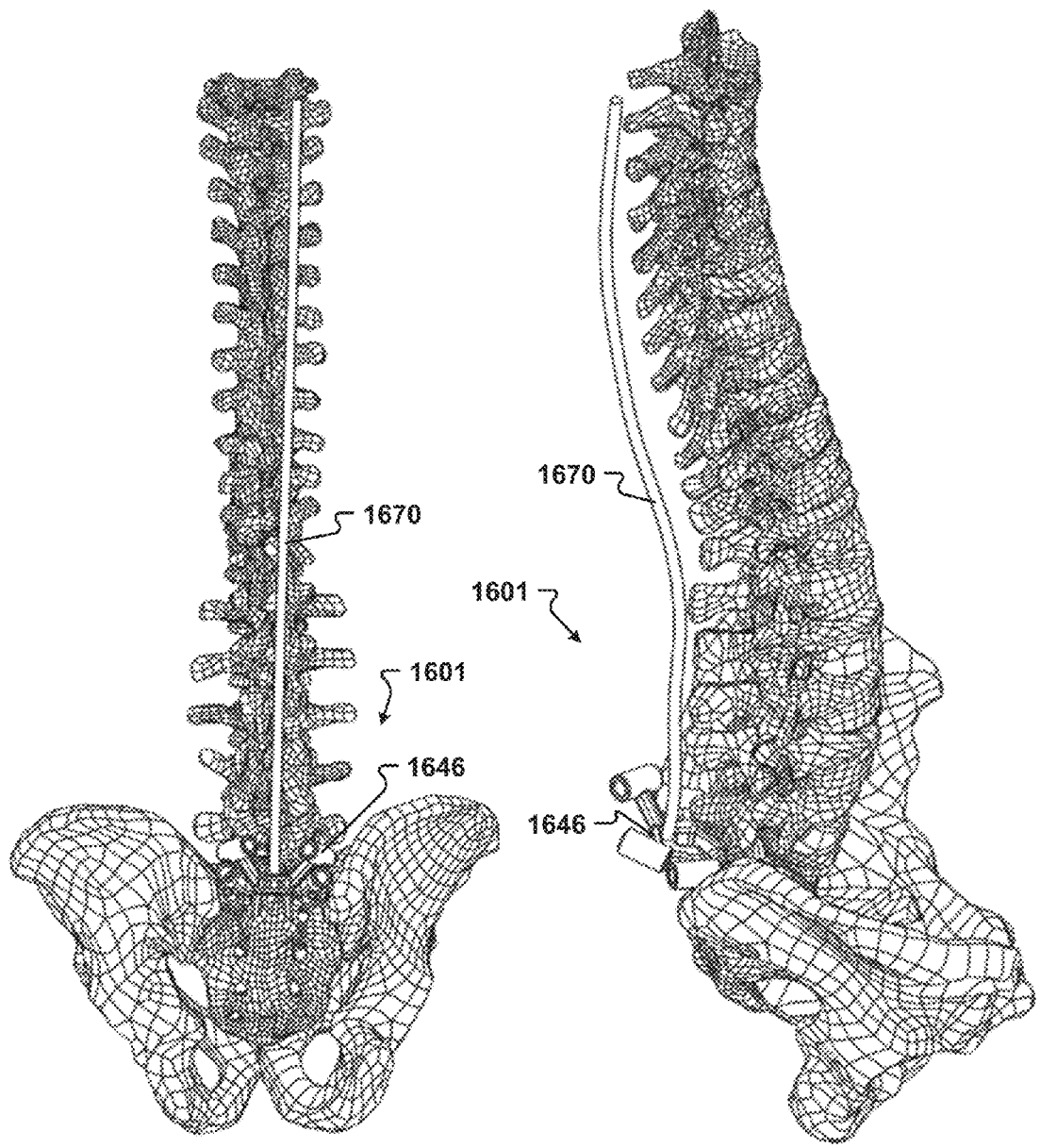
Figures 26A, 26B:
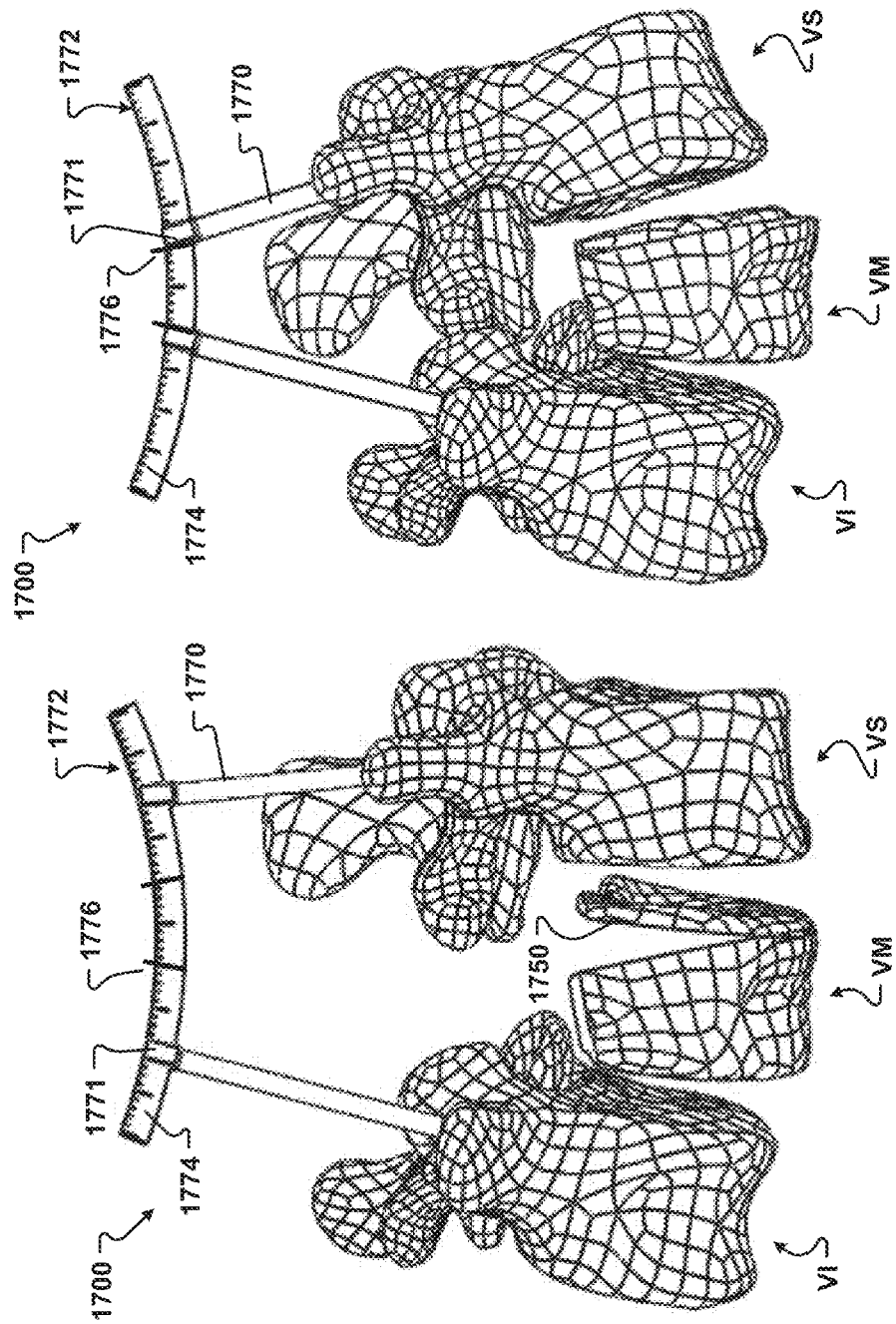
Figure 27D:
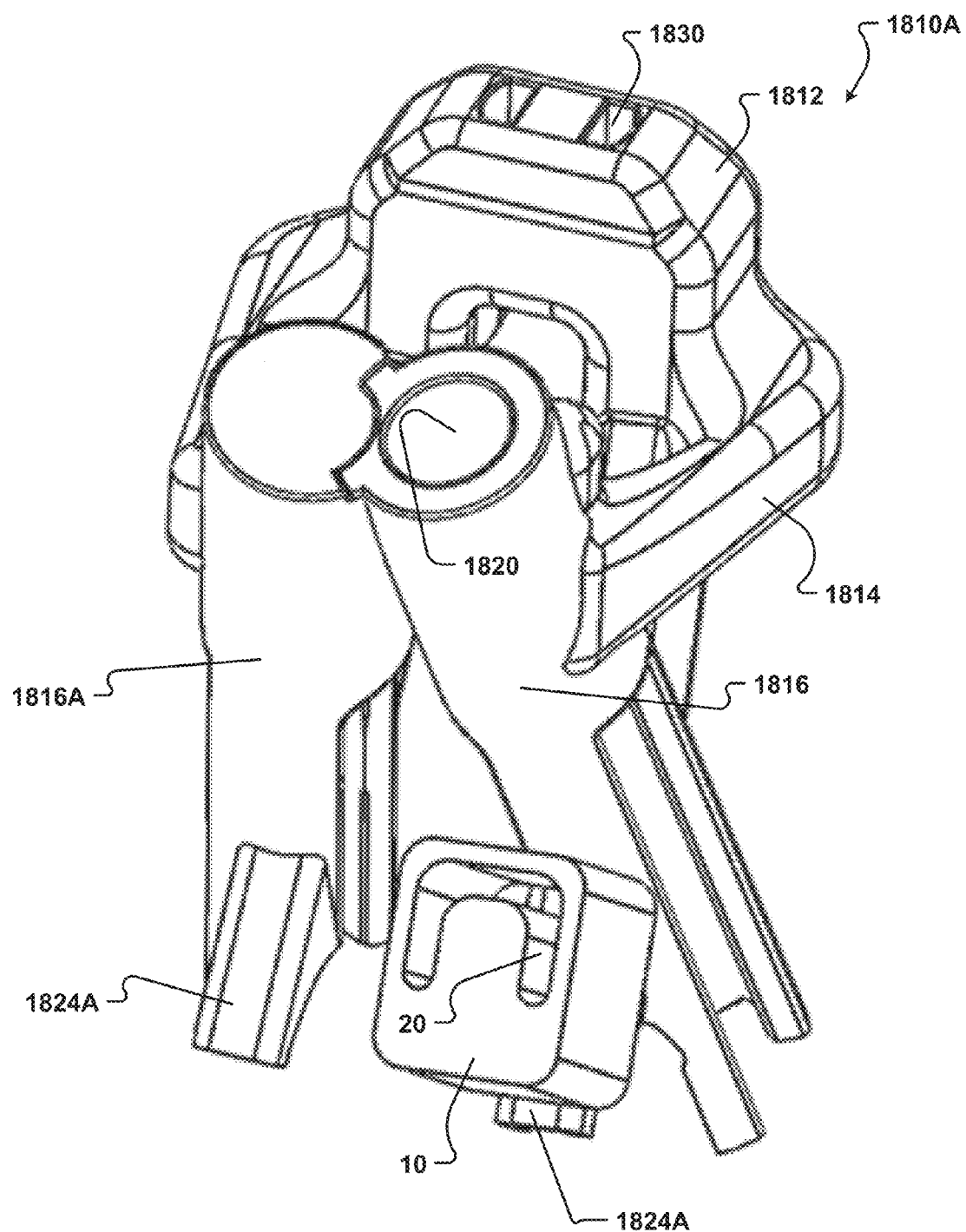
Figure 27E:
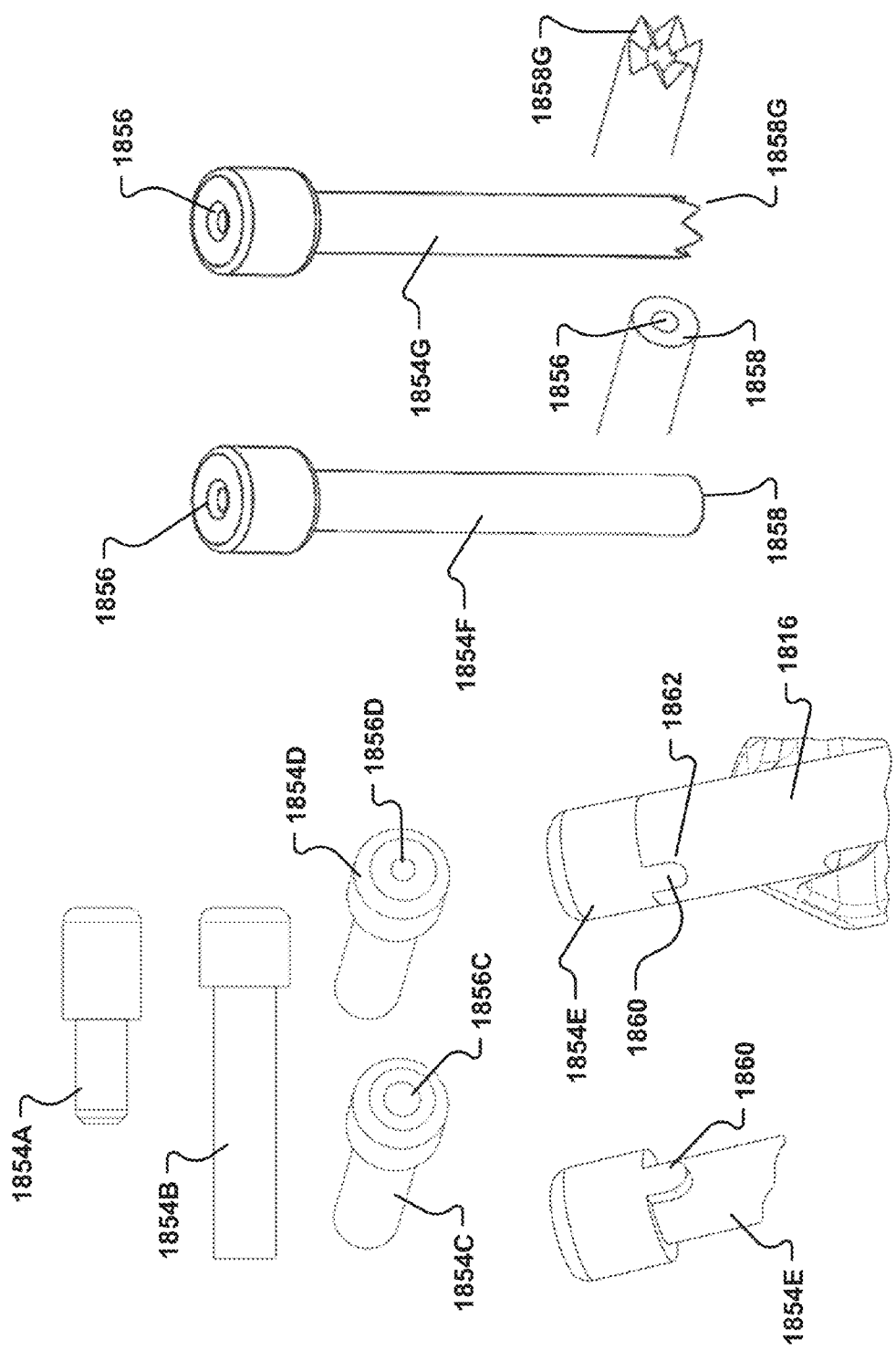
Figures 33D, 33E, 33F:
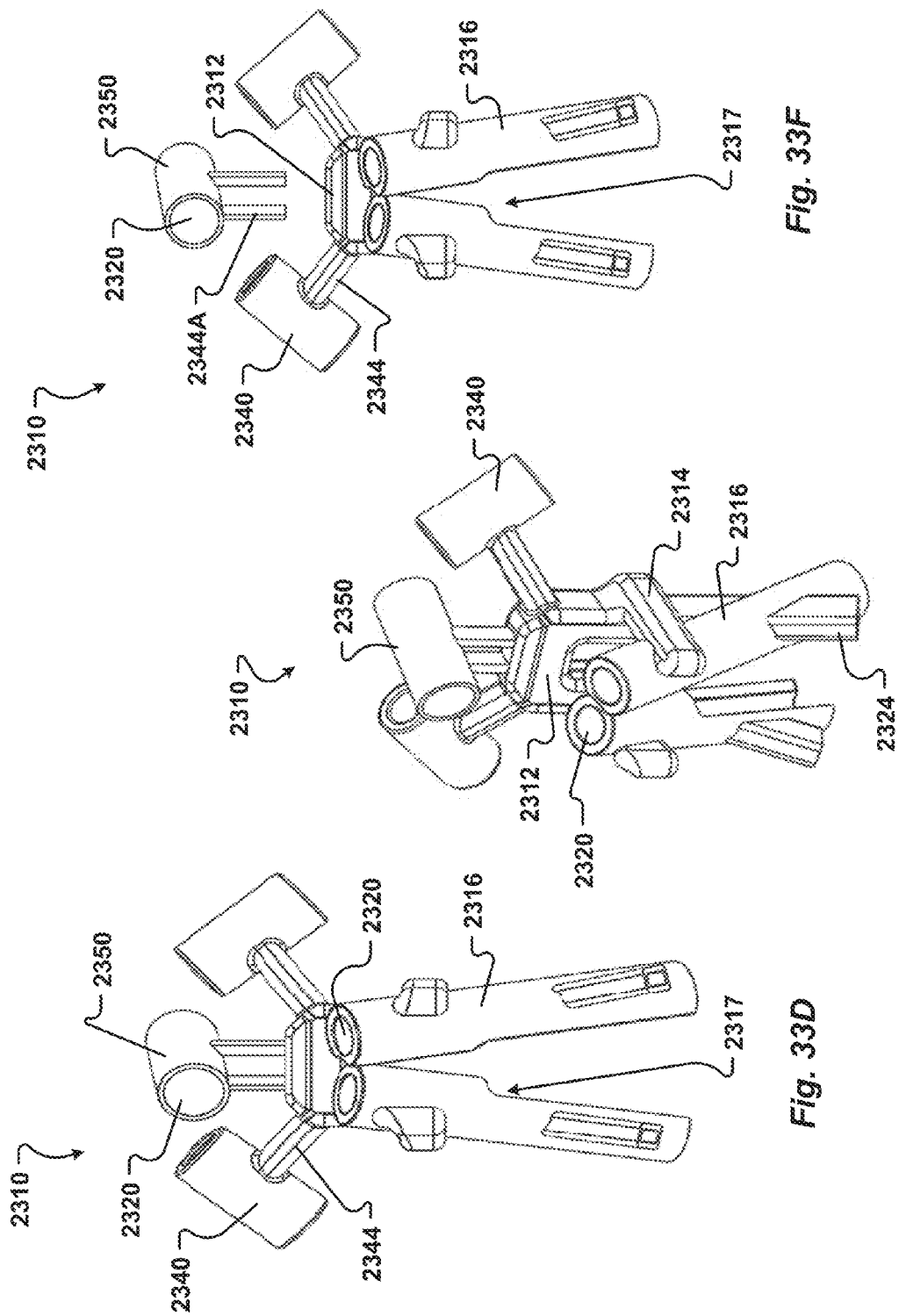
Figure 35A:
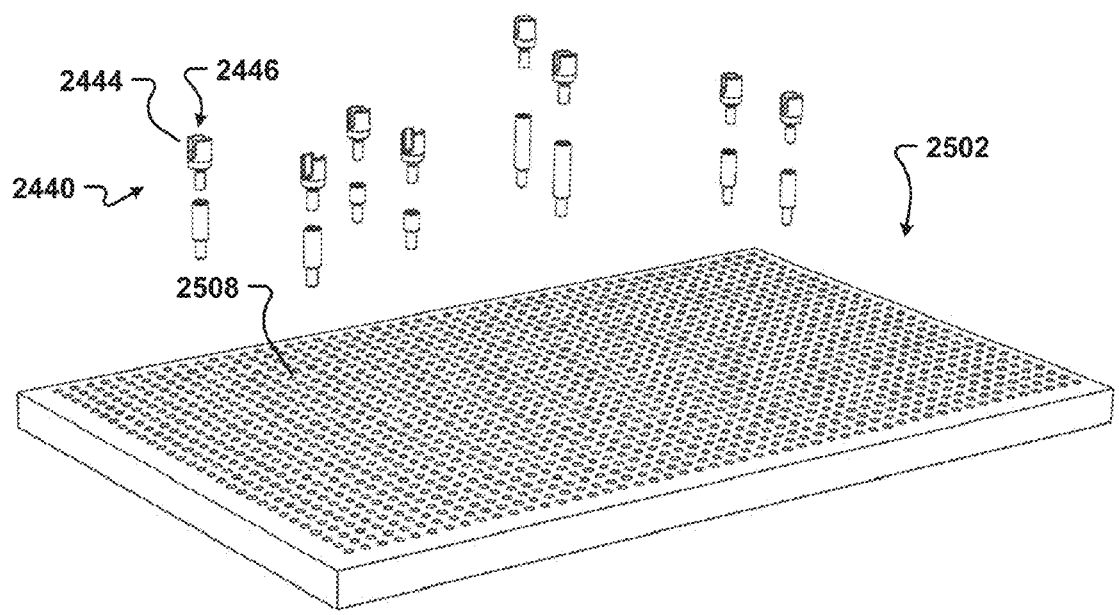
Figure 35B:
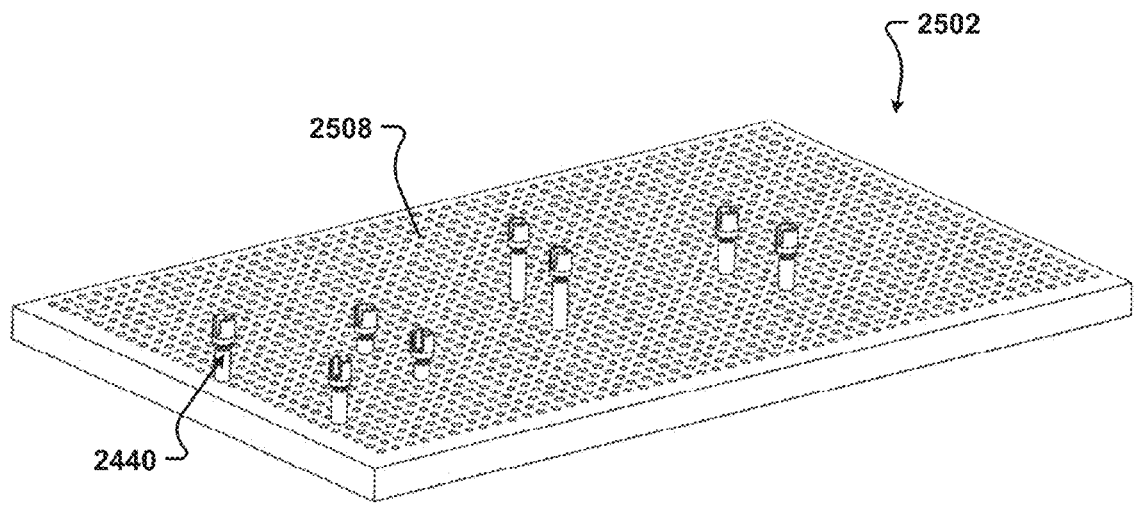
Figure 35C:
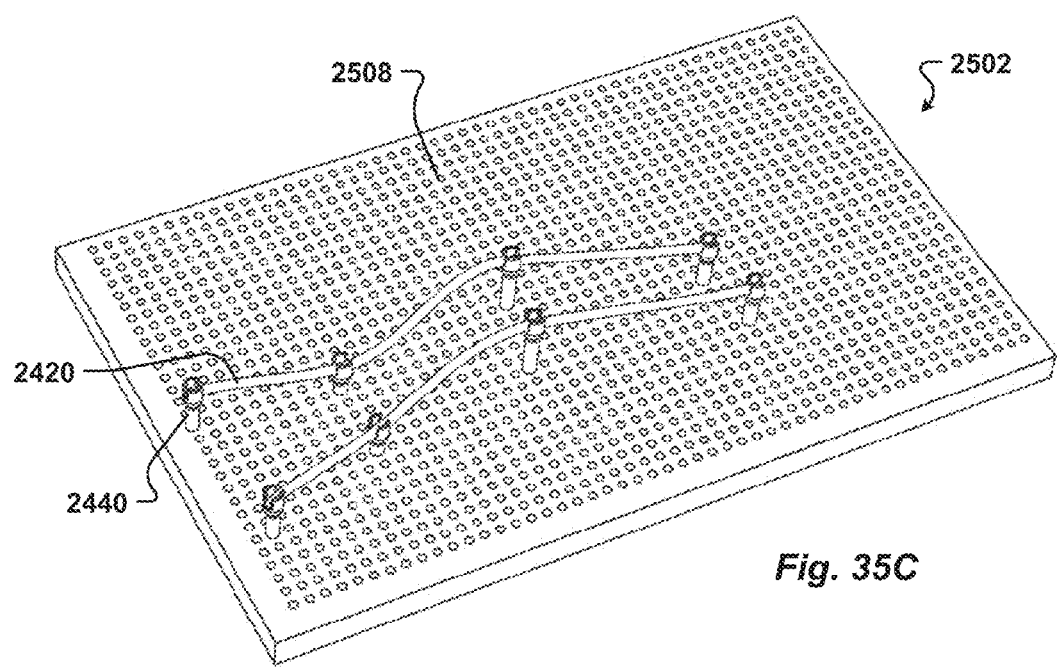
Figure 35D:
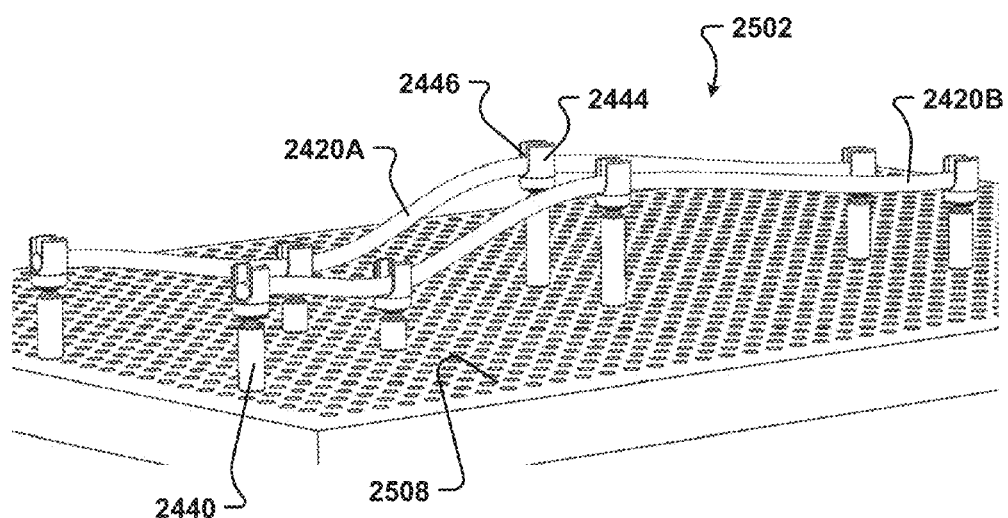
Figure 35E:
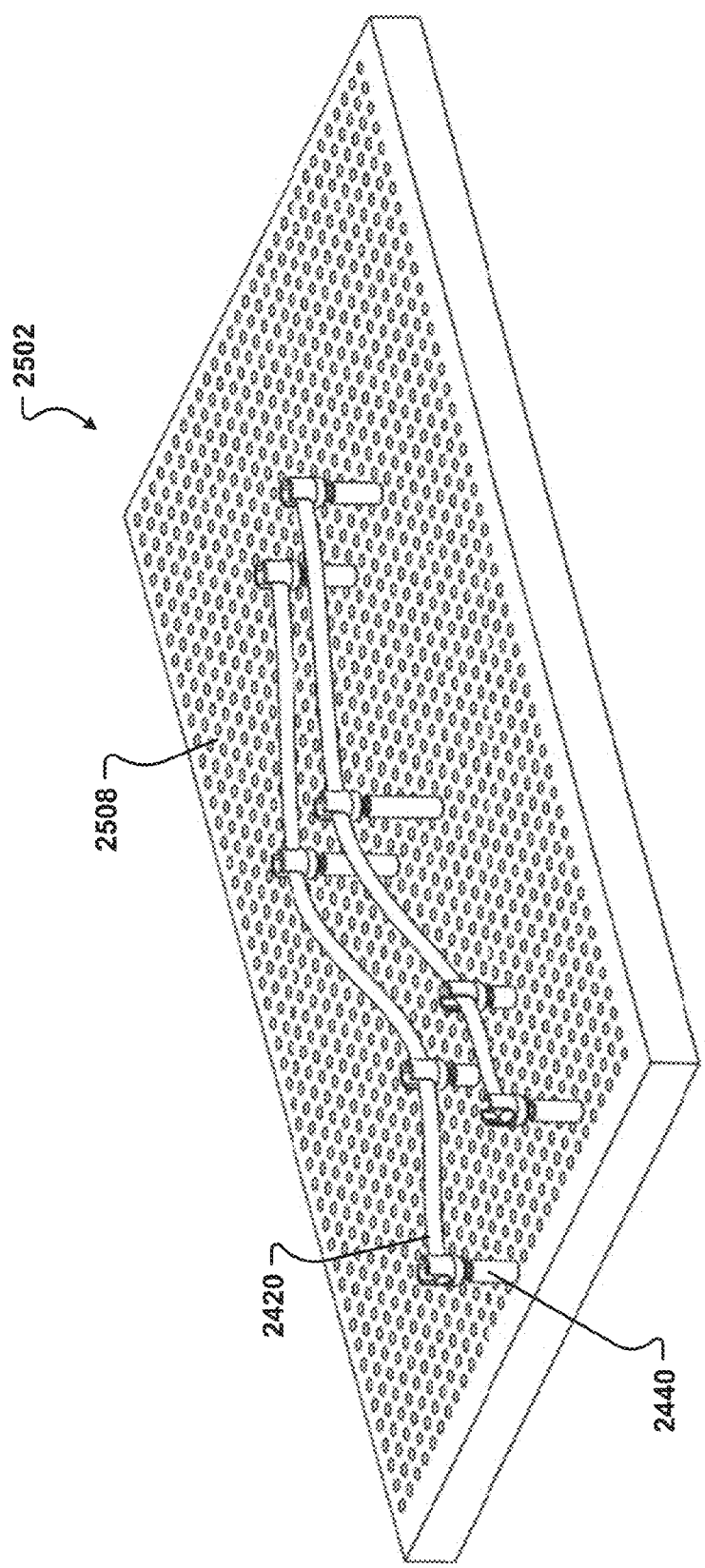
Figure 36:
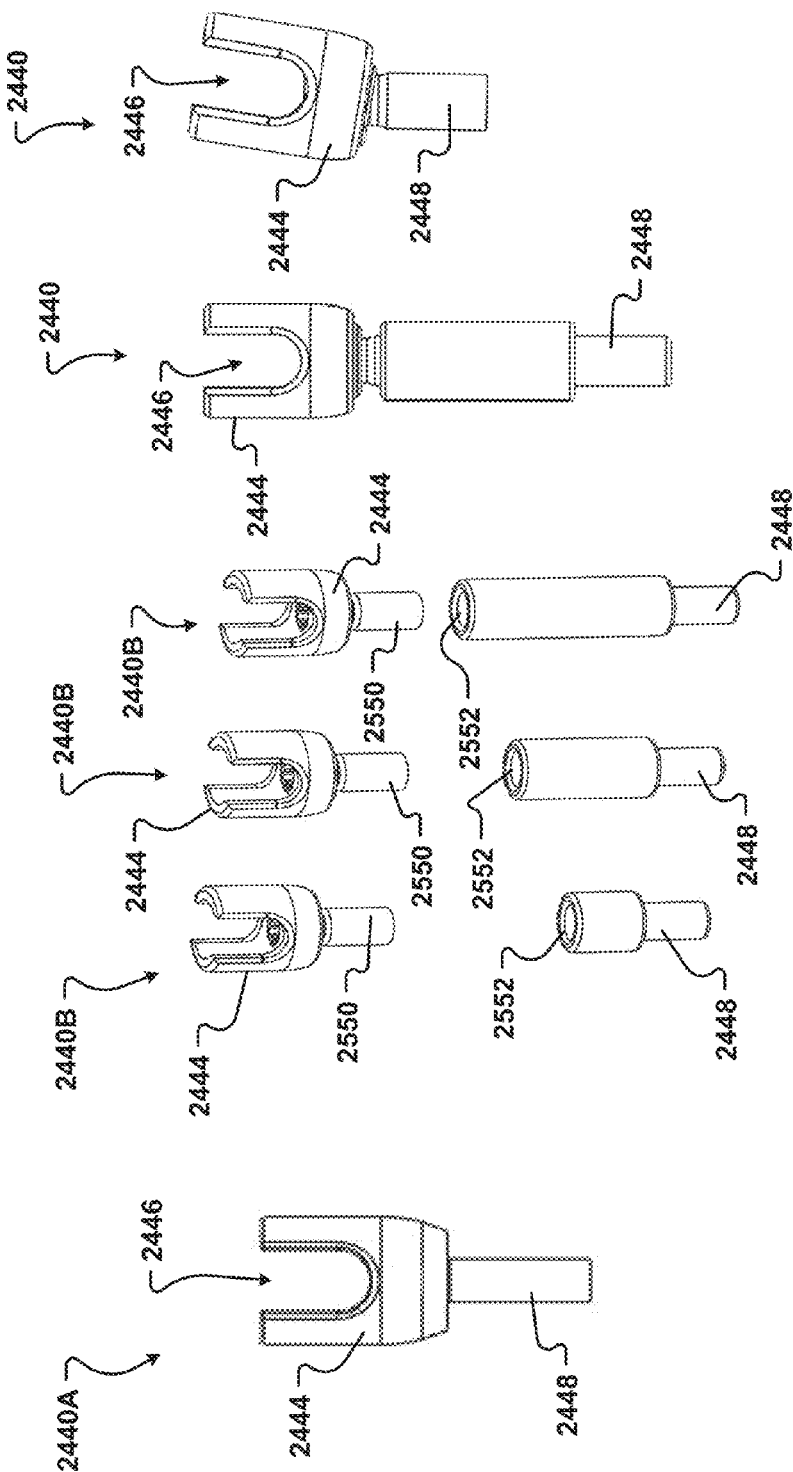
Figures 38A, 38B:
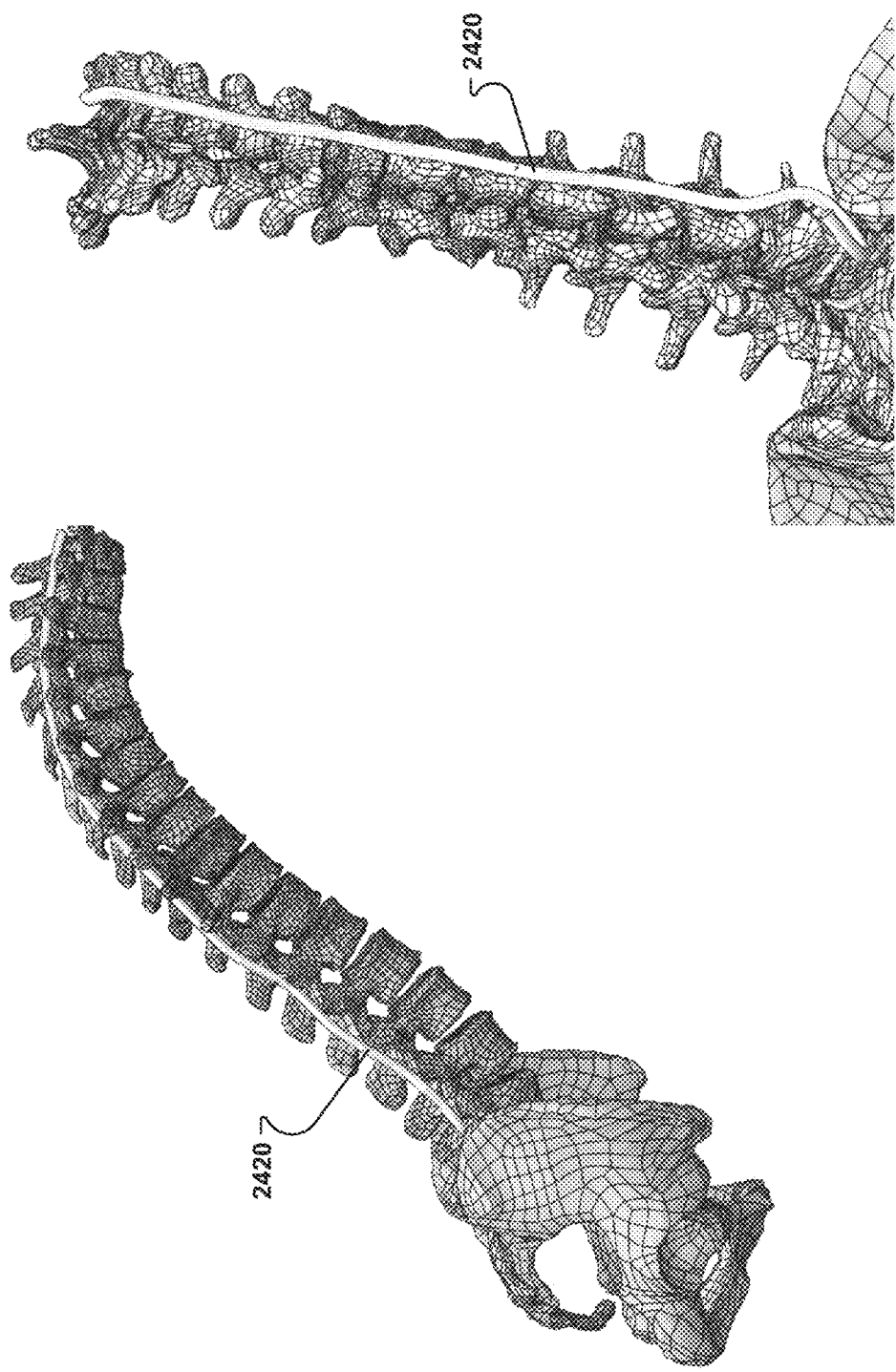
Figure 39:
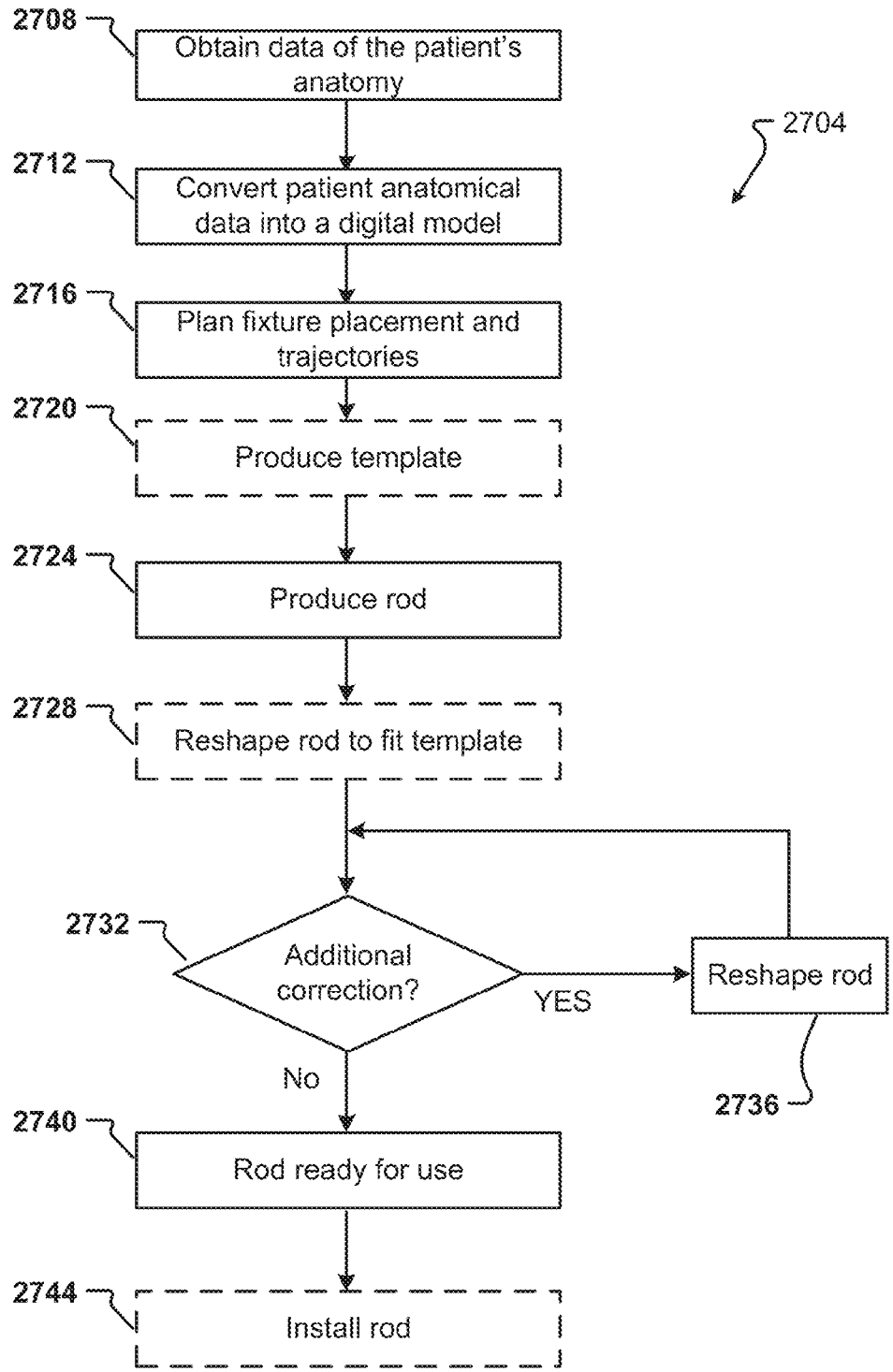
Figure 40B:
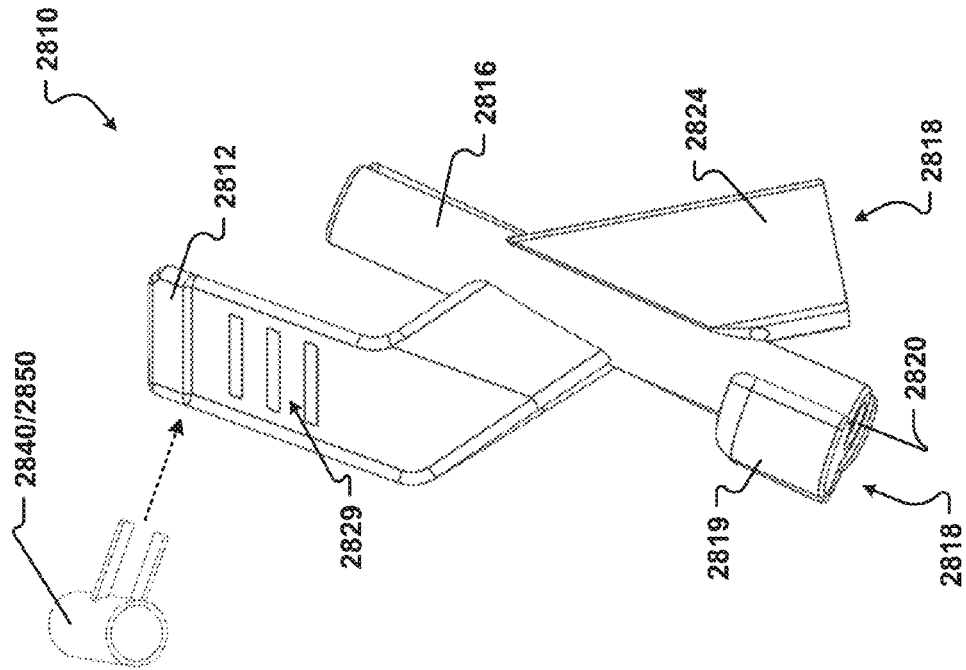
Figure 40A:
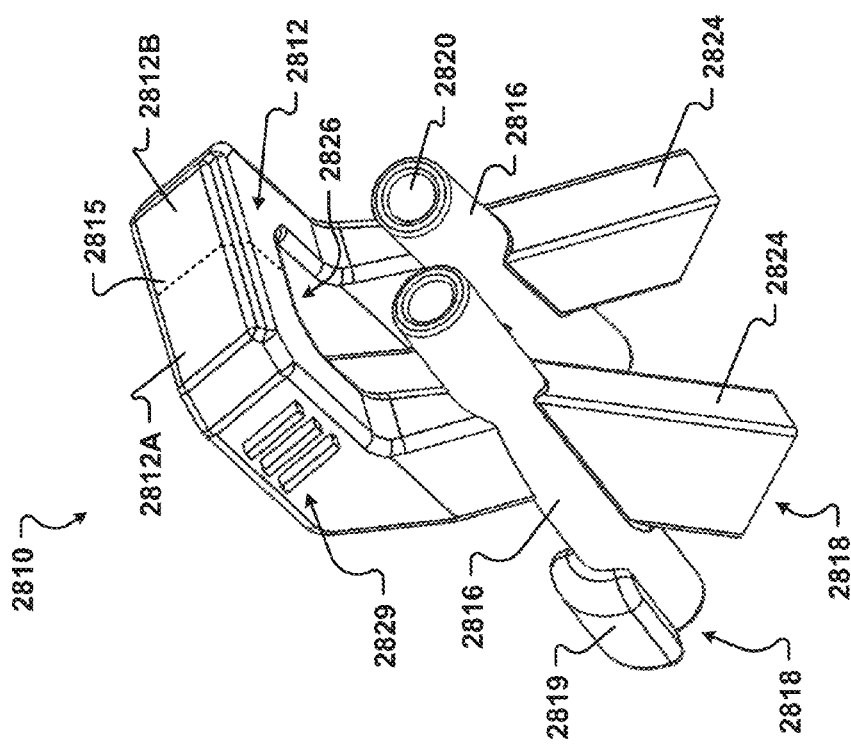

FIG. 7B is another front elevation view illustrating a boring instrument of an embodiment of the present invention inserted in a cannula of the guide of FIG. 7A;

FIG. 7C is a side view of a guide sleeve of an embodiment of the present invention positioned proximate to the vertebral body illustrated in FIG. 7A;

FIG. 7D is side view of a cutting tool of an embodiment of the present invention inserted into a cannula of the guide sleeve of FIG. 7C;

FIG. 7E is a perspective view of the cutting tool and the guide sleeve of FIG. 7D;

FIGS. 7F-7G are additional perspective views of the cutting tool and the guide sleeve of FIG. 7D;

FIG. 8A is a front elevation view of a frame of an embodiment of the present invention interconnected to a portion of a patient's spine;

FIG. 8B is a front elevation view of a guide of another embodiment of the present invention interconnected to the frame of FIG. 8A;

FIG. 8C is a perspective view of the guide and the frame of FIG. 8B;

FIG. 8D is another perspective view of the guide and the frame of FIG. 8B including hidden lines showing the structure of slots formed in the guide;

FIG. 9A is a front elevation view of a guide of another embodiment of the present invention;

FIG. 9B is a rear elevation view of the guide of FIG. 9A;

FIG. 9C is a bottom perspective view of the guide of FIG. 9A;

FIG. 9D is another front elevation view of the guide of FIG. 9A positioned against a vertebral body and including hidden lines showing the structure of slots formed in the guide;

FIG. 9E is a perspective view of the guide of FIG. 9A positioned against the vertebral body and including hidden lines;

FIG. 9F is a side elevation view of the guide of FIG. 9A positioned against the vertebral body;

FIG. 9G is another side elevation view of the guide of FIG. 9A positioned against the vertebral body and illustrating cuts formed in the vertebral body;

FIG. 10A is a front elevation view of still another guide of an embodiment of the present invention;

FIG. 10B is another front elevation view of the guide of FIG. 10A positioned against a vertebral body;

FIG. 10C is a side perspective view of the guide of FIG. 10A;

FIG. 10D is a side view of the guide of FIG. 10A positioned against the vertebral body;

FIG. 10E is a top view of the guide of FIG. 10A positioned against the vertebral body;

FIG. 11A is a front elevation view of yet another guide of an embodiment of the present invention;

FIG. 11B is another front elevation view of the guide of FIG. 11A positioned against a vertebral body;

FIG. 11C is a side perspective view of the guide of FIG. 11A;

FIG. 11D is another side perspective view of the guide of FIG. 11A positioned against the vertebral body;

FIG. 11E is a side view of the guide of FIG. 11A positioned against the vertebral body;

FIG. 12A is a front elevation view of a frame of an embodiment of the present invention interconnected to a portion of a patient's spine;

FIG. 12B is a elevation view of another guide of an embodiment of the present invention interconnected to the frame of FIG. 12A;

FIG. 12C is a perspective view of the guide and frame of FIG. 12B;

FIGS. 13A-13B are perspective views of still another guide of an embodiment of the present invention;

FIG. 13C is a perspective view of the guide of FIG. 13A positioned against a vertebral body that has been altered in a surgical procedure;

FIG. 13D is a front elevation view of the guide of FIG. 13A positioned against a portion of the patient's spine that has been altered in a surgical procedure and further illustrating the guide in relation to a neural element of the patient;

FIG. 13E is a perspective view of the guide of FIG. 13A positioned against a portion of the patient's spine that has been altered in a surgical procedure and showing the guide positioned proximate to the neural element of the patient;

FIGS. 14A-14B are perspective views of a guide of yet another embodiment of the present invention;

FIGS. 14C-14D are additional perspective view of the guide of FIGS. 14A-14B positioned against a vertebral body that has been cut to remove portions of the vertebrae;

FIG. 14E is another perspective view of the guide of FIG. 14A positioned against the vertebral body and neural elements of the patient;

FIG. 15A is a perspective view of yet another guide of the present invention;

FIG. 15B is a side view of the guide of FIG. 15A positioned in contact with a vertebral body that includes cuts formed using the guide;

FIG. 15C is a perspective view of the guide of FIG. 15A positioned in contract with the vertebral body of FIG. 15B;

FIG. 15D is a front elevation view of the guide of FIG. 15A illustrated in a position of use against a portion of a patient's spine and illustrating a neural element of the patient positioned proximate to a recess of the guide;

FIG. 15E is a side perspective view of the guide of FIG. 15D in a similar position of use;

FIG. 16A is a perspective view of a model of an embodiment of the present invention;

FIG. 16B is a side elevation view of the model of FIG. 16A;

FIG. 16C is rear elevation view of the model of FIG. 16A;

FIG. 16D is a perspective view of the model of FIG. 16A positioned in contact with a vertebral body;

FIG. 16E is a side elevation view of the model of FIG. 16A positioned in contact with the vertebral body of FIG. 16D;

FIG. 17A is a front elevation view of another model of an embodiment of the present invention;

FIG. 17B is a rear elevation view of the model of FIG. 17A;

FIG. 17C is a rear perspective view of the model of FIG. 17A;

FIG. 17D is another front elevation view of the model of FIG. 17A in a position of use against a vertebral body;

FIG. 17E is a front perspective view of the model of FIG. 17D;

FIG. 17F is a top perspective view of the model of FIG. 17D;

FIG. 18A is a front perspective view of another embodiment of a model of the present invention;

FIG. 18B is a front elevation view of the model of the embodiment of FIG. 18A positioned proximate to a vertebral body;

FIG. 18C is a perspective view of the model and vertebral body of FIG. 18B;

FIG. 19A is a perspective view of yet another guide of an embodiment of the present invention adapted to interconnect to a model of an embodiment of the present invention and showing the guide and the model in a disassembled state;

FIG. 19B is a perspective view of the model and the guide of FIG. 19A in an assembled state;

FIG. 19C is a front elevation view of the model and the guide of FIG. 19B;

FIG. 19D is a perspective view of the model and the guide of FIG. 19B positioned proximate to a vertebral body;

FIG. 19E is a front elevation view of the model and the guide of FIG. 19D positioned proximate to the vertebral body;

FIG. 20A is a perspective view of still another embodiment of a model of the present invention;

FIG. 20B is a side elevation view of the model of FIG. 20A;

FIG. 20C is a perspective view of the model of FIG. 20A interconnected to a frame of the present invention similar to the frame of FIG. 12A, illustrating the model in a position of use proximate to a portion of the patient's spine;

FIG. 20D is a side elevation view of the model of FIG. 20C;

FIG. 21A is a perspective view of another embodiment of a model of the present invention;

FIG. 21B is a side perspective view of the model of FIG. 21A;

FIGS. 21C-21D are views of the model of FIG. 21A in a position of use interconnected to a frame of the present invention, the frame fixed to a portion of a patient's spine;

FIG. 22A is a perspective view of a three-dimensional model of a unique grouping of a portion of patient's spine of an embodiment of the present invention and illustrating a portion of the spine being removed;

FIG. 22B is a side elevation view of the three-dimensional model of FIG. 22A;

FIG. 22C is a perspective view of the removed spine portion after some of the removed spine portion has been cut away;

FIG. 22D is a side elevation view of the three-dimensional model of FIG. 22D after the model has been moved to close a gap formed after a portion of the spine was removed;

FIG. 22E is a side elevation view of the three-dimensional model of FIG. 22B and further illustrating an alignment indicator of the present invention interconnected to the three-dimensional model and with the model showing the alignment of the patient's spine before the planned surgical procedure;

FIG. 22F is another side elevation view of the three-dimensional model of FIG. 22D and further illustrating the alignment indicator of FIG. 22E interconnected to the three-dimensional model and with the model showing the alignment of the patient's spine after the planned surgical procedure;

FIG. 23A is a perspective view of a coronal alignment verification tool of an embodiment of the present invention positioned proximate to a portion of a patient's anatomy;

FIG. 23B is a front elevation view of the tool of FIG. 23A;

FIG. 23C is a bottom elevation view of the tool of FIG. 23A;

FIG. 23D is a top elevation view of the tool of FIG. 23A;

FIG. 24A is a perspective view of another embodiment of a coronal alignment verification tool of the present invention positioned proximate to a portion of a patient's spine;

FIG. 24B is a front elevation view of the tool of FIG. 24A;

FIG. 24C is a top elevation view of the tool of FIG. 24A;

FIG. 24D is a right side elevation view of the tool of FIG. 24A;

FIG. 25A is a front elevation view of another tool of an embodiment of the present invention for verification of coronal alignment;

FIG. 25B is a right side elevation view of the tool of FIG. 25A;

FIG. 25C is a perspective view of the tool of FIG. 25A;

FIG. 25D is a front view of the tool of FIG. 25A proximate to a portion of the patient's spine and aligned in relation to the sagittal plane;

FIG. 25E is a side view of the tool of FIG. 25D proximate to the patient's spine and aligned in relation to the coronal plane;

FIG. 26A-26B illustrate two side view of an alignment assembly in a position of use interconnected to a portion of a patient's spine before and after the alignment of the spine is altered during a planned surgical procedure;

FIGS. 27A-D are various views of yet another patient-specific guide of an embodiment of the present invention for contacting surfaces and trajectories in a patient's spine;

FIG. 27E illustrates various inserts adapted for use with the patient-specific guides of the present invention;

FIGS. 28A-C are various views of the guide of FIGS. 27A-C shown in relation to a vertebral body of a patient;

FIGS. 29A-C are various views of another patient-specific guide of another embodiment of the present invention for contacting surfaces and trajectories in a patient's spine;

FIGS. 30A-B are various view of still another embodiment of a patient-specific guide of an embodiment of the present invention;

FIGS. 31A-C are various views of another patient-specific guide of an embodiment of the present invention;

FIGS. 32A-C are various views of a patient-specific guide for contacting surfaces and trajectories in a patient's spine according to yet another embodiment of the present invention;

FIGS. 33A-F are various views of a guide of an embodiment of the present invention further comprising secondary and tertiary sleeves of still another embodiment of the present invention;

FIGS. 34A-34F are various views of a patient-specific bone model of an embodiment of the present invention adapted for use to form a surgical rod for use in a surgical procedure;

FIG. 35A-35E provide views of a configurable template of an embodiment of the present invention that can be used to shape a surgical rod;

FIG. 36 illustrates embodiments of pegs of embodiments of the present invention adapted for use with the model and template of FIGS. 34-35;

FIGS. 37A-37B are views of a template of yet another embodiment of the present invention;

FIGS. 38A-38B are views of a rod of one embodiment of the present invention in position proximate to a patient's spine;

FIG. 39 is a flow diagram of a method of the present invention for configuring a rod for use in a surgical procedure; and FIG. 40A-40B are various view of still another embodiment of a patient-specific guide of an embodiment of the present invention.

DETAILED DESCRIPTION

As shown in the appended Figures and described in further detail herein, the present disclosure relates to a novel system and method for developing a variety of customized, patient-matched apparatus for use in a diverse number of surgical procedures. The system and method uses a patient's unique morphology, which may be derived from capturing MRI data, CT data, or any other medical imaging device to derive one or more patient-matched apparatus, which comprise complementary surfaces to those encountered during the surgical procedure(s) as derived from a set of data points. According to various embodiments described herein, the patient-matched apparatus may further comprise desired axes and/or insertional trajectories. According to one alternate embodiment described herein, the patient-matched apparatus may be further matched with at least other apparatus used during the surgical procedure. Other features of the disclosure will become apparent after a review of the following disclosures and varying embodiments of the invention.

Figure 1:
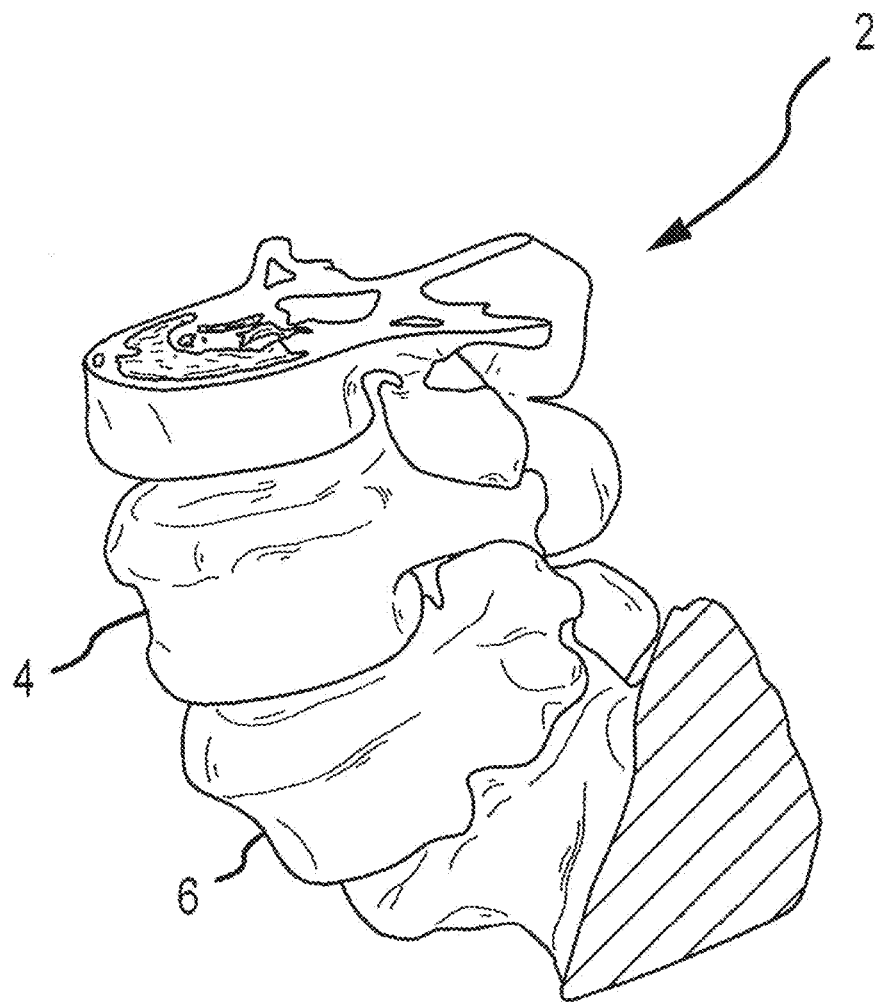

Multiple embodiments of the disclosure are depicted in FIGS. 1-40. Referring now to FIG. 1, a perspective view of a three-dimensional model of a unique grouping of anatomical features according to one embodiment of the present disclosure is shown. Here, the model 2 is comprised of multiple vertebral bodies 4, 6 but according to other embodiments may be comprised of any anatomical grouping for a particular patient. Data associated with the model 2 may be captured from a MRI or CT scan or from radiographic images of the patient's corresponding boney anatomy (or alternatively from other data sources). The data, once captured, may be converted using known software tools to a computer aided design (CAD) program, where the data set is representative of the model 2 and may be used to provide additional data points for forming the contours, sizes, shapes and orientations of one or more apparatus to be used in the surgical procedure.

According to an alternative embodiment, the data may be obtained from an ultrasonic or nuclear medicine scanning device. In yet another alternative embodiment, the data may be supplemented or merged with data from a bone density scanner to fabricate a device that is designed to remain in the patient after the surgical procedure is completed, or alternatively to achieve further control over the orientation of any desired axes, particularly where the surgical procedure involves insertion of one or more implantable devices.

Figure 2:
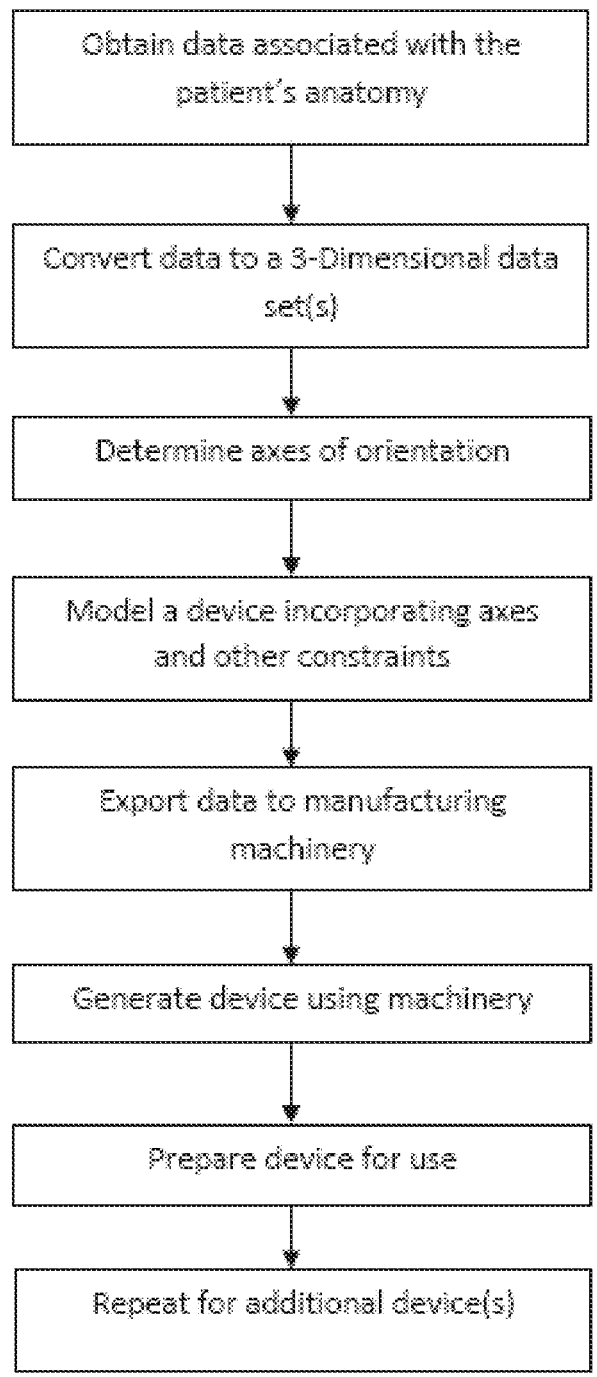

FIG. 2 is a flow chart showing the various steps of performing a method of manufacturing an apparatus, such as a guide, a spinal fusion rod, or a template of a predetermined portion of a patient's anatomy according to various embodiments described herein, for use in facilitating a surgical procedure. While a general order for the steps of the method is shown in FIG. 2, the method can include more or fewer steps or can arrange the order of the steps differently than those shown in FIG. 2. The method, according to a preferred embodiment, comprises, but is not limited to, the following steps:

A) Obtaining data associated with the patient's anatomy by way of, but not limited to, a MRI or CT scan;

B) Converting the MRI or CT scan data to a 3-Dimensional data set(s);

C) Determining one or more axes of orientation of a device to be constructed for use in facilitating the surgical procedure(s) to be performed on the patient;

D) Modeling the device for use in facilitating the surgical procedure(s) using the determined axes and accounting for any other constraints derived from the converted data set(s);

E) Generating a prototype of the modeled device by, for example, use of rapid prototyping machinery; and F) Preparing the prototype for use during the surgical procedure(s).

As shown in FIG. 2, the method may comprise additional steps or may be repeated for additional devices used in the surgical procedure. The step of obtaining data is typically performed in a traditional manner, by subjecting the patient to a scan using, for example, MRI or CT or other suitable scanning equipment known in the art. The data is then captured by the equipment and may be converted to a 3-Dimensional data set(s) by software or other algorithmic means known in the art, such as by exporting the data into a known modeling software program that allows data to be represented, for example, in CAD format. Once this data is converted, a device may be modeled to complement the data set(s) and oriented by one or more axes determined by the surgeon either before or through observation of the data set(s) from the initial scan of the patient's anatomy.

The method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc. The prototype may be generated using known rapid prototyping machinery, or alternatively by milling machinery such as a CNC milling machine. Alternatively, the initial device fabricated by this method may be in a temporary state for further consideration and or manipulation by the surgeon, and then finally constructed using one of the methodologies described herein. The steps may be repeated for complementary devices, some or all of which may include further matching surfaces for the patient's anatomy or to the previously fabricated devices (i.e., the devices fabricated may have matching surfaces for adjoining together one or more devices, as described in greater detail below).

Alternatively, the system and method described herein may facilitate the alignment of various anatomical features for a particular patient, such as, for example, multiple vertebral bodies in a patient to correct spinal deformities. For example, the data set(s) may provide an initial location for the anatomical features, but may be further manipulated by the surgeon in a pre-operative setting to create a desired data set(s), such as a final location for the anatomical features once the surgical procedure(s) are completed. In this manner, the devices formed by the system and method described above may be used in either an initial location or a final location for the anatomical features, and be matched to those specific locations and orientations for each stage of the surgical procedure. These staged devices would in turn provide the surgeon with a visual guide to determine the degree of correction achieved through the surgical procedure, as compared to the pre-operative plan. Other variations on the method of the present disclosure are described in the Summary of the Invention and included in the appended claims.

Fabrication methods may comprise the use of a rapid prototyping machine, such as a stereolithography (STL) machine, selective laser sintering (SLS) machine, or a fused deposition modeling (FDM) machine, direct metal laser sintering (DMLS), electron beam melting (EBM) machine, or other additive manufacturing machine. One example of such a rapid prototyping machine is commercially available from 3D Systems and known as Model SLA-250/50. The rapid prototyping machine selectively hardens a liquid, powdered or other non-hardened resin or metal into a three-dimensional structure, which can be separated from the remaining non-hardened resin, washed/sterilized and used directly as the apparatus. The prototyping machine receives the individual digital data sets and produces one structure corresponding to each of the desired apparatus.

Generally, because stereolithographic machinery produces a resin, which may have less than optimal mechanical properties (which may not be generally acceptable for a particular surgical use), the prototyping machine may alternatively be used to produce a mold. After the model is prepared, a conventional pressure or vacuum molding machine may be used to produce the apparatus from a more suitable material, such as stainless steel, titanium alloy, aluminum alloy, chromium alloy, PEEK, carbon fiber, or other metals or metal alloys.

According to another alternative embodiment, the system and method may comprise providing the data set(s) to a CNC machine, which in turn may be utilized to manufacture a custom milled apparatus from one of the more mechanically sound materials listed above. In yet another alternative embodiment, volume manufacturing of apparatus in accordance with the embodiments described herein may also be achieved, for example, where a particular orientation or insertion trajectory is common among a large grouping of patients.

According to one particular embodiment of the present disclosure, a system and method is provided for fabricating apparatus for use with a variety of surgical procedures associated with a patient's spine. Individuals who suffer degenerative disc disease, natural spine deformations, a herniated disc, spine injuries or other spine disorders often require surgery on the affected region to relieve the individual from pain and prevent further injury. Such spinal surgeries may involve removal of damaged joint tissue, insertion of a tissue implant and/or fixation of two or more adjacent vertebral bodies, with the surgical procedure varying depending on the nature and extent of the injury.

For patients with varying degrees of degenerative disc disease and/or nerve compression with associated lower back pain, spinal fusion surgery, or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra.

Fusion may occur in the lumbar, thoracic or cervical spine region of a patient. Fusion requires tools for accessing the vertebrae and implanting the desired implant, any bioactive material, etc. Such procedures often require introduction of additional tools and/or instruments, including drills, drill guides, debridement tools, irrigation devices, vises, clamps, cannulae, retractors, distracters, cutting tools, cutting guides and other insertion/retraction tools and instruments. The insertion, alignment and placement of these tools, instruments and fixation devices are critical to the success of the operation. As such, providing a customized and patient-specific tool or instrument increases the likelihood that the surgical procedure will be successful.

Figure 3:
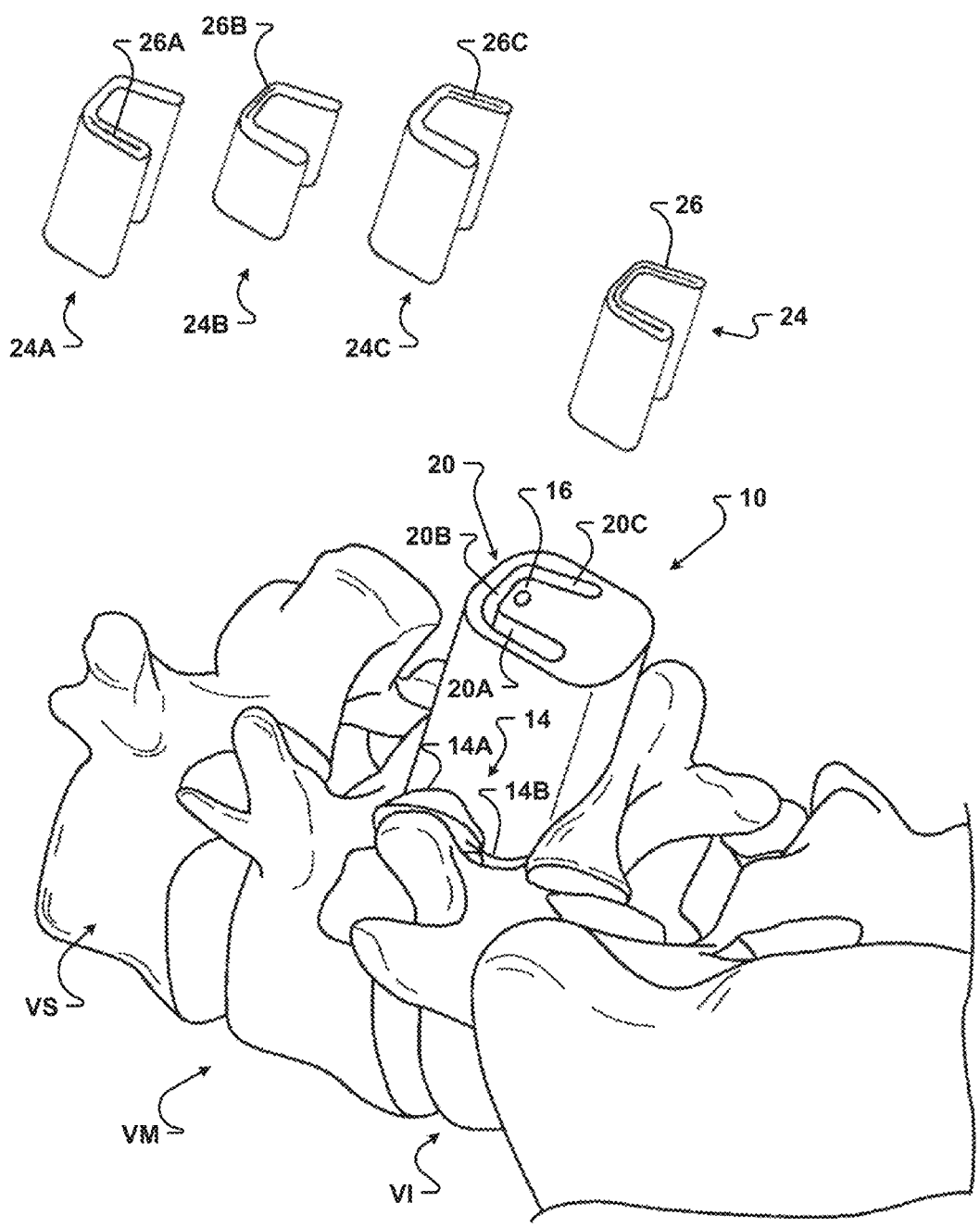

FIG. 3 is a perspective view of an apparatus for facilitating a surgical procedure according to an embodiment of the present disclosure. In this embodiment, the apparatus formed by the system and method described above comprises a cutting guide 10. The guide 10 can be used to orient a cutting tool to alter and, optionally, remove portions of the anatomy of the patient. A variety of cutting tools, including (but not limited) routers, burrs, and osteotome may be used with the guide.

The guide 10 illustrated in FIG. 3 is a laminectomy guide adapted to facilitate the use of surgical cutting instruments to alter the patient's lamina. However, guides of the present invention may be adapted for use in procedures to alter any portion of the patient's anatomy. In one embodiment, the guides of the present invention may be used in procedures to alter posterior portions of the patient's anatomy, including without limitation facet joints, transverse processes, articular processes, and spinous processes of a patient.

In the embodiment of the present invention illustrated in FIG. 3, the guide 10 is adapted to fit directly to aspects of a patient's anatomy. More specifically, the guide is positioned proximate to a medial vertebrae VM between a superior and inferior vertebrae VS, VI. Thus, the laminectomy cutting guide 10 also comprises a lower patient-contacting surface 14 which permits the laminectomy cutting guide 10 to mate with one or more vertebral bodies. The patient specific surface 14 can be specific to any portion of the patient's anatomy, such as lamina, transverse processes, articular processes, spinous processes, etc. Alternatively, the guide 10 can be interconnected to a frame as described in more detail below. Surface 14 may be adapted to at least partially hook around a portion of the patient's anatomy. For example, the surface 14 may comprise multiple portions 14A, 14B that are adapted to contact two different planes formed by two distinct portions of the patient's anatomy. In this manner, the surface 14 provides a reference to align the guide 10 with a predetermined portion of the patient's anatomy.

A single guide 10 may target one portion of the lamina. Alternatively, the guide may be sized to facilitate a procedure targeting more than one portion of the patient's anatomy, including, for example, both sides of the lamina substantially simultaneously.

The laminectomy cutting guide 10 illustrated in FIG. 3 further comprises at least one alignment channel 16 for inserting a guide wire or other securing element, and a cutting slot 20 for directing the path of a blade or other cutting edge. The slot 20 can have any shape determined to guide cuts for a planned surgical procedure for a particular patient. For example, the slot may have a shape to guide instruments to provide straight, concave, convex, or 'chevron' shaped cuts. In one embodiment, the slot includes multiple portions 20A, 20B, 20C.

The cutting slot 20 may be sized or shaped to receive a particular cutting tool and to prevent the use of an inappropriate tool. Additionally, the slot may be shaped to guide a cut around a neural element of the patient or to prevent a cut into a neural element. Accordingly, the slot 20 can be used to guide instruments along a presurgically planned pathway while controlling instrument orientation and depth. Further, the width of the slot may change to control the size of a cutting tool that fits through the slot. For example, slot portion 20A may have a different dimension than portions 20B, 20C. In one embodiment of the present invention, slot portion 20A has a different width than slot portions 20B, 20C.

Stops may be formed in the slot 20 to limit or control the depth of insertion of the cutting tool. The stops may be specific to the patient's anatomy and allow for protection of neural elements of the patient. The slot 20 may also be keyed to ensure depth control while cutting. For example, the slot may include a key that alters the depth of cutting by the tool as the tool is guided through the slot. The key may correspond to a feature, such as a protrusion 144 on the tool 140, described in more detail in conjunction with FIG. 5, that limits the depth of insertion of the tool.

Optionally, a sleeve 24 or an insert is provided for the slot 20. The insert 24 includes a slot 26 for a cutting tool. The sleeve 24 separates and protects the guide 10 from the cutting tool. For example, if the guide 10 is formed of a material that may be cut by the cutting tool, the size and shape of the slot 20 could be changed by the cutting tool. The insert 24 is provided to prevent the cutting tool from altering the slot 20. In this manner, the insert may prevent deviation from a planned surgical procedure.

It will be appreciated that the insert 24 may have any size and shape selected to be at least partially received in the slot 20. Further, the insert may project at least partially from the proximal side of the guide 10. In one embodiment, the insert 24 has a cross-sectional profile substantially the same as the cross-sectional profile of the slot 20. The insert 24 may have a length that is the same as, or similar to, the depth of the slot.

In one embodiment, the slot 20 may be sized to receive more than one sleeve 24. Each sleeve may be adapted to guide a different tool or define a different cut. For example, a first sleeve may be introduced into the slot to guide a first tool to create a first cut. The first sleeve may then be replaced by a second sleeve introduced into the slot. The second sleeve may guide a second tool to create a second cut. The second sleeve may have a different size and shape than the first tool. In one embodiment, the second cut alters the first cut. Alternatively, in another embodiment, the second cut does not intersect the first cut.

The insert 24 may be formed of any material that is of sufficient strength that breaking and/or flaking of the insert material is avoided. Accordingly, the insert may withstand the effects of high-speed cutting tool without damaging the insert or permitting material from the insert to become deposited in the cutting site as well as re-use of the insert. The insert material must also withstand the high temperatures encountered during sterilization. In one embodiment the insert is formed of a metal or metal alloy, although other materials are contemplated. One benefit of a metallic insert is the ability to "trephine" or machine a cutting surface to permit the distal end of the insert to "bite" into the bone and provide means for fixation of the insert. Forming a trephine on the distal end may provide further stabilization of the guide during a cutting operation. In another embodiment, the insert is formed of any material that is harder than the material of the guide.

The insert 24 may be adapted to receive different types and sizes of tools. Additionally or alternatively, the insert may be operable to receive only one particular tool. Inserts can also be provided to ensure cuts are performed in a preplanned sequence. For example, when the slot of a guide has a compound shape, such as slot 20 with three different portions, the surgical plan may include a first operation through slot portion 20A followed by operations through portion 20B and then 20C. Accordingly, a first insert 24A may be provided to receive a tool in portion 20A through slot 26A while blocking access to slot portions 20B, 20C. After the first operation is completed, the first insert may be replaced with second and third inserts 24B, 24C to allow access to slot portions 20B, 20C. One of the inserts, for example, insert 24B, may have a different length that the other inserts.

Additionally or alternatively, the insert may 24 include stops to limit an angle of use of the cutting tool during the surgical procedure. Indicia may be positioned on the guide and the inserts to indicate a sequence of use conforming to the sequence of operations in which the guide is to be used. The indicia may also indicate a tool to be used, a direction of a cut to be performed, or a particular portion of the patient's anatomy targeted by a cut.

The alignment channel 16 may receive a fixture, such as a pedicle screw, to temporarily fix the guide 10 to the patient's spine. Placing a fixture through the channel 16 can increase stability of the guide during use of the guide in a cutting procedure. Optionally, the channel 16 may comprise a cannula adapted to receive a tool, such as a tool for forming a bore in the patient's anatomy. Thus, in one embodiment, the alignment channel 16 may optionally comprise a bore adapted to guide an instrument or a fixation device.

In one embodiment, the cutting guide 10 designed following acquisition of a scan of the patient's anatomy with a medical imaging device. The scan may be performed by a CT scanner, an MRI scanner, or any other medical imaging device. The scan is segmented into 3D models of each vertebra. These 3D models are then modified in CAD to simulate the correction desired by the surgeon. Once the desired correction is appropriately simulated, a guide 10 is generated that will allow the surgeon to make the planned corrections intraoperatively. The guides may then be manufactured through 3D printing, rapid prototyping, or an alternative method for creating patient-specific features as described above.

Although shown in FIG. 3 as a generally rectangular prism, it is expressly understood that other geometrical shapes for the laminectomy cutting guide 10 are equally as practical, and considered within the scope of the disclosure. The cutting guides of the present invention can be used as physical cutting guides. Additionally, the cutting guides may be used as an aid to indicate to surgeons the angle and location of osteotomy cuts so that neural elements in the patient's spine are not harmed. The guides may also be used pre-surgically on models of the patient's anatomy to test or practice the planned surgical procedure. At least a portion of the proximal end of the guide is configured to extend outside of the patient during a surgical procedure.

Figure 4A:
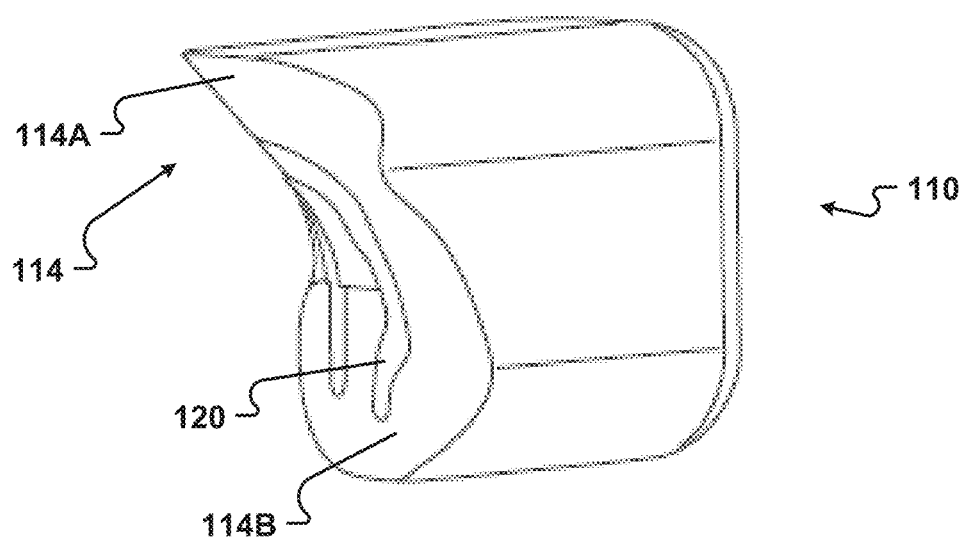
Figure 4B:
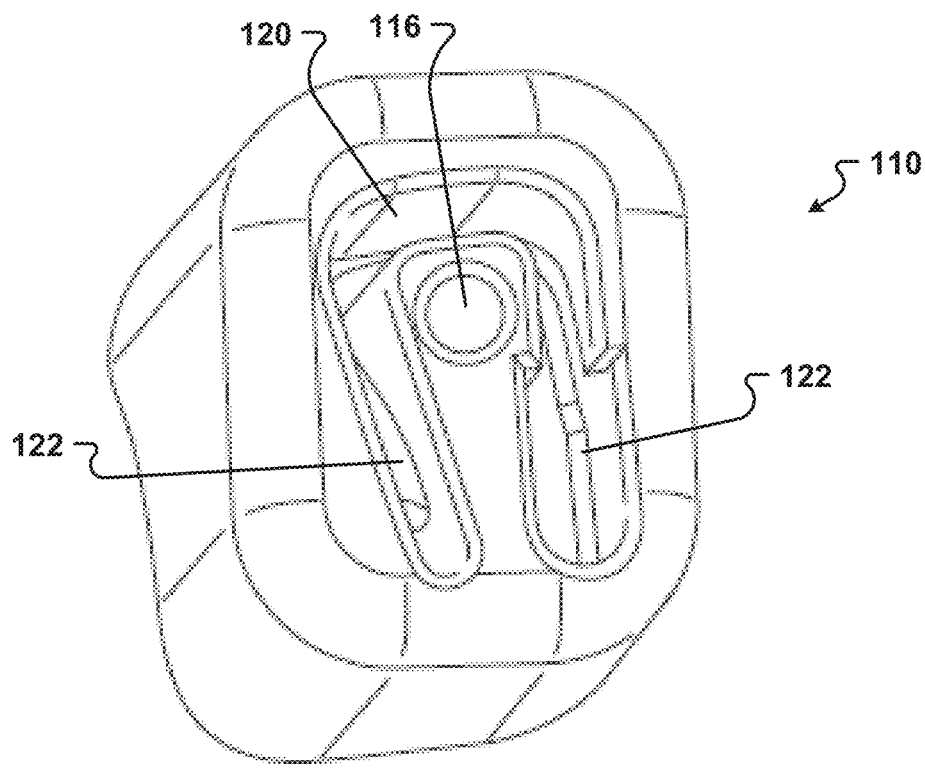

Referring now to FIGS. 4A-4B, further illustrations of a cutting guide 110 (similar to the guide 10 depicted in FIG. 3 above), are provided. According to one embodiment, the cutting guide 110 comprises a plurality of patient-specific contacting surfaces 114 about at least one surface of the cutting guide and an alignment channel 116. The contacting surfaces may comprise portions 114A, 114B adapted to hook at least partially around portions of the patient's anatomy. In one embodiment, the contacting surfaces 114 are adapted to conform to cut surface generated by removal of a portion of the patient's anatomy. The cutting guide further comprises, in a preferred embodiment, a patient-specific slot or "track" 120 for facilitating insertion of a cutting instrument (as shown in FIGS. 5A-C) and controlling the depth of insertion for that instrument to prevent unnecessary cutting of the underlying surface during a particular surgical procedure by further providing one or more instrument contacting surfaces 122.

According to the embodiment shown in connection with FIGS. 4-6, the cutting guide 110 may be provided for a laminectomy. According to other embodiments, the patient-specific guide may be fabricated for use in performing a corpectomy, a Pedicle Subtraction Osteotomy (PSO), a Smith-Peterson Osteotomy (SPO), a Vertebral Column Resection (VCR), or an Asymmetric Osteotomy (in either the sagittal or coronal plane), among others.

These patient-specific cutting guides may be fabricated from patient anatomical data, and may assist in performing complex procedures with greater certainty in their outcomes. For example, certain osteotomies, specifically PSO and SPO, require a great deal of surgical skill and are often time consuming. This is due in part to the intimate relationship of the vascular and neural elements to the boney structures, which create navigational challenges for a surgeon to safely and efficiently resect the bone during one of these procedures. This is especially true from a posterior approach. By using a patient-specific guide, a surgeon may confirm positioning and alignment of the cutting trajectory and path prior to initiating the procedure, and in furtherance of the disclosure provided above in relation to FIGS. 4-6, may also provide a degree of depth control essential for avoiding contact with vascular and neural elements.

In one embodiment, the cutting tool 140 associated with the cutting guide 110 shown in FIGS. 4-6 is typical of the type of tools currently used in surgical procedures today. According to another embodiment, a specialty cutting bur or tip 142 may be included with the instrument to facilitate further control of the location and depth of the instrument, as described in further detail below. For example, as shown in FIGS. 5A-5C, the cutting portion of the instrument may have a protrusion 144 that prevents greater insertion of the instrument 140 into the cutting guide 110 than required for the patient-specific procedure. In one embodiment, the position of the protrusion 144 on the cutting tip 142 may be adjusted by a user. The protrusion 144 may be of any form adapted to interact with contact surfaces 122 of the slot 120 to control the use of the cutting tool 140. In one embodiment, the protrusion 144 is a bearing. In another embodiment, the protrusion is a track ball. In still another embodiment, the protrusion is generally disc-shaped.

Figure 6A:
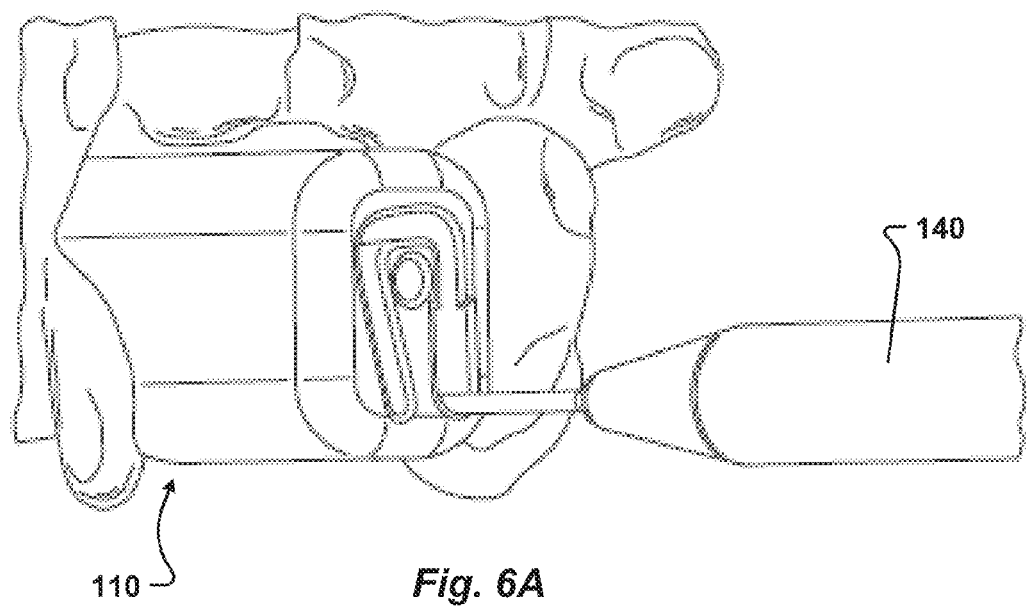
Figure 6B:
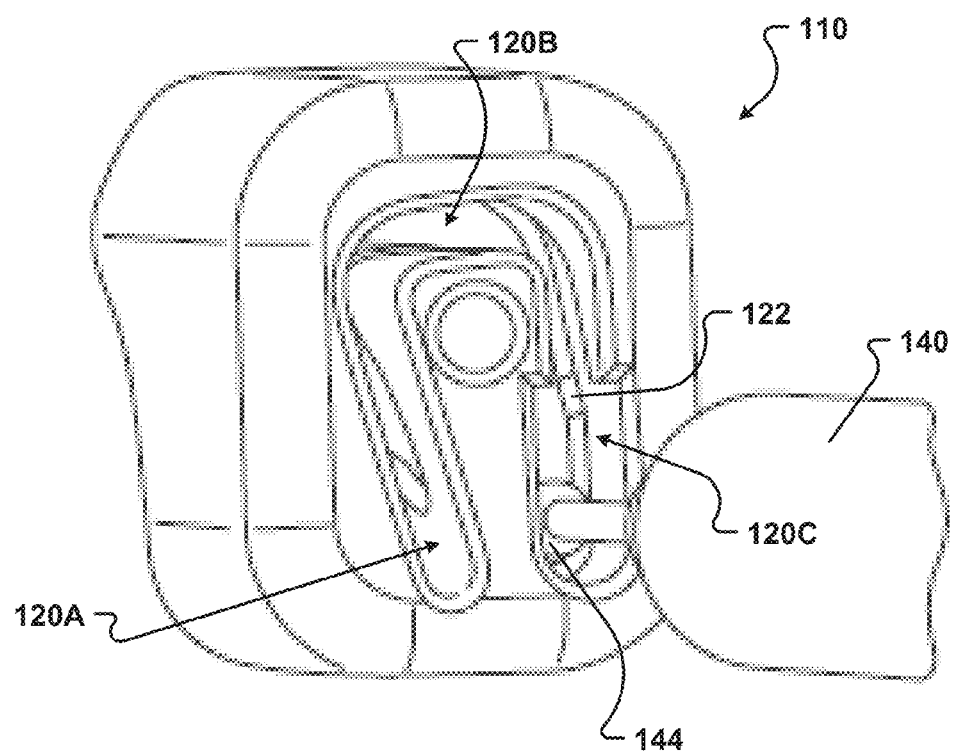

As shown in greater detail in FIGS. 6A-6B, the protrusion 144 may be inserted into a first portion 120C of the "track" 120 of the cutting guide 110, but not permitted to insert a second or third deeper portions 120A, 120B of the "track" of a cutting guide (through which the cutting surface is permitted to travel), thereby insuring proper depth of the cutting instrument. Further geometrical configurations other than those shown in FIGS. 6A-6B may be provided that allow the protrusion 144 to move horizontally with respect to the top surface of the cutting guide, and in some instances laterally and downwardly into the track 120 of the cutting guide. In this embodiment, the cutting instrument 140 would therefore be permitted to move at a certain depth about a patient's anatomy in a certain location of the "track" 120 of the cutting guide, but achieve a greater depth at yet other locations about the "track" 120 of the cutting guide 110. Thus, the depth permitted with respect to the instrument relative to the cutting guide may be variable about the "track" 110 of the cutting guide.

It will be appreciated by one of skill in the art that the size and location of the surfaces 122 may be altered as desired. Accordingly, in other embodiments of the present invention, the instrument 140 may be inserted and removed from different portions of the track 120, or from two or more portions of the track. Further, in one embodiment, the track 120 and the instrument 140 include protrusions that interact to permit the tool to be inserted in only a first portion of the track, for example portion 120C, and removed from only a second portion of the track, such as portions 120A or 120B.

Other benefits achieved from the use of these patient-specific cutting guides include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Referring now to FIGS. 7A-7F, a guide sleeve 210 of another embodiment of the present invention is described. The sleeve 210 is adapted for use in a posterior osteotomy, also known as a Smith-Petersen Osteotomy (SPO) or a "ponte osteotomy" procedure. As will be appreciated by one of skill in the art, during a posterior osteotomy, a portion of bone is removed from the back of the patient's spine. Portions of the posterior ligament and facet joints may also be removed from targeted portions of the patient's spine. The osteotomy may be performed at one or multiple locations along the spine to correct the alignment of the patient's spine.

In one embodiment of the present invention, a surgical guide 246, guide sleeve 248 and drilling insert or sleeve 249 assembly according to an embodiment of the present disclosure is positioned proximate to a targeted portion of the patient's anatomy. The drill sleeve 249 (placed through the patient-matched guide sleeves 248 and into the bone at opposing, dissimilar angles) provides additional fixation of the guide 246 to the vertebra V.

The guide 246 is used to introduce a bore (not illustrated) into the pedicle for the guide sleeve 210. The trajectory of the bore is specifically planned and controlled by sleeve 248 for the drilling sleeve 249. The placement of bore is selected in such a way that neural elements are protected from the tool 247 inserted through the drilling sleeve 249. The trajectory of the bore is selected to be a predetermined distance away from the neural elements so that the tool 247 is a safe distance away. In one embodiment, the bore is at least 0.25 mm away from the patient's neural elements. However, it will be appreciated that any predetermined distance separating the bore from neural elements may be used. In another embodiment, the distance is from about 0.1 mm to about 3 mm.

Referring now to FIGS. 7C-7G, once the pedicle is cannulated, the surgical guide 246 may be removed from the vertebrae V. A guide sleeve 210 is inserted to a controlled depth within the bore. The cutting tool 240 is inserted into a cannula 225 of the sleeve 210 and activated. The tool includes a surface 242 that cuts from the interior to the exterior of the pedicle. In one embodiment of the present invention, the guide sleeve 210 includes an aperture 218 for the cutting surface 242. The aperture 218 may be spaced from the distal end of the guide sleeve 210 by a predetermined amount to control the depth of the cut. In another embodiment, the aperture is positioned at the distal end of the sleeve 210.

The cutting surface 242 may be mechanically or electrically actuated. The cutting surface 242 may comprise a reciprocating or a rotating blade, or any other type of cutting tool. In one embodiment, the orientation or length of the cutting surface 242 may be altered by the surgeon during the surgical procedure. Optionally, in another embodiment of the present invention, the tool is operable to ablate portions of the pedicle to complete the cut. For example, the tool may comprise a laser adapted to burn through portions of the pedicle from within the bore. In another embodiment, the tool may comprise a heated surface to burn or otherwise remove portion of bone or tissue. Once the cut has been made, the posterior column of the vertebra can be removed.

Referring now to FIGS. 8A-8D, an embodiment of a guide 310 comprising a frame 330 is illustrated. The guide 310 is adapted for use in a posterior osteotomy, although other procedures are contemplated. The frame 330 may have a patient-specific shape. For example, the frame may be adapted to flex or snap into a position in contact with a transverse process T or other portion of the patient's anatomy. Alternatively, the frame 330 may be designed to be used in surgical procedures for any patient.

In use, the frame 330 is interconnected to fixtures 334 positioned in predetermined portions of the patient's anatomy, such as the patient's vertebrae, V. In one embodiment, as illustrated, the vertebrae V include an inferior vertebra VI, a medial vertebra VM, and a superior vertebra VS. The fixtures 334 may be pedicle screws. Although two screws 334 in each of the inferior and superior vertebra VI, VS are illustrated in use with the frame of the embodiment of FIG. 8, it will be appreciated that any number, including fewer screws, may be used with the frame. The size and shape of the frame 330 may be selected to only permit the frame to be interconnected to the screws when the frame is in a pre-planned orientation. For example, the embodiment of the frame 330 illustrated in FIG. 8A has a shape that only permits the frame to be interconnected to the four pedicle screws 334 when the frame is in one predetermined orientation. Accordingly, the shape of the frame is adapted to ensure proper alignment of the frame and the guide, limiting the possibility of misuse of the frame and guide.

The pedicle screws 334 may be placed in the vertebrae using any tool or guide. Pre-existing pedicle screws from a previous surgery may be used with the frame. One or more of the pedicle screws may also be positioned using a pedicle screw guide of an embodiment of the present invention, for example, the guide 246 described above. Other embodiments of pedicle screw guides are described in the Applicant's co-pending U.S. patent application Ser. No. 14/298, 634 which is incorporated herein in its entirety.

The frame 330 serves multiple purposes. For example, the frame may retract soft tissue in the surgical area. Further, reference points or indicia may be provided on the frame 330 for docking the osteotomy guide 310. The indicia may indicate a planned orientation or alignment of the guide. The shape of the frame 330 may only permit docking of the guide when the guide is in a pre-planned orientation with respect to the targeted vertebrae.

The frame 330 may also be used to distract the vertebrae in a target area of the patient's spine by a predetermined amount. The distraction provided by the frame may ensure a cut is formed at a predetermined angle. The distraction may also be necessary to provide access to a predetermined portion of the patient's anatomy. Once interconnected to the pedicle screws 334, the frame 330 may also prevent unintended movement of the vertebrae during the surgical procedure. The frame may also be planned such that it increases the distraction of the construct to provide the surgeon with a larger window through which the surgery can be completed. In this embodiment the frame connects the superior vertebra VS (above the osteotomy location of the medial vertebra VM) to the inferior vertebra VI (below the osteotomy location). In one embodiment, the frame is positioned lateral to the pedicles so that the posterior anatomy of the medial vertebra VM is substantially unobstructed by the frame 330. It will be appreciated by one of skill in the art that the frame may be sized to span any number of vertebra.

Once the frame 330 is interconnected to the pedicle screws, the guide 310 is interconnected to the frame. The guide 310 is presurgically planned to align on the frame with targeted portions of the medial vertebrae VM in a patient-specific location so that cuts are made accurately.

Although the embodiment of the guide 310 illustrated in FIGS. 8B-8D is shown as one piece, it will be appreciated that in other embodiments the guide could include multiple pieces or a series of cutting guides that are placed in a specific order to generate a series of planned cuts. In embodiments of guides comprising multiple pieces, each piece of the guide may be keyed to interconnect in a specific order and location to other pieces of the guide. In one embodiment, the guide 310 does not contact the patient's anatomy. Said another way, the guide 310 is adapted to float over a surgical area when the guide is interconnected to the frame 330. In another embodiment, at least a portion of the guide 310 is adapted to contact the patient's anatomy.

The guide may include slots 320 and apertures 328. The aperture 328 may be positioned to prevent contact with portions of the patient's anatomy. For example, the guide 310 of the embodiment illustrated in FIGS. 8B-8D includes and aperture 328 to at least partially receive the spinous process S of the medial vertebra VM. The aperture 328 and surfaces of the guide proximate to the patient's anatomy may include patient specific contours adapted to substantially conform to predetermined portions of the patient's anatomy. In this manner, the alignment of the guide with a planned portion of the patient's anatomy may be enhanced. The patient specific contact contours may also improve the stability of the guide 310 during the procedure.

The slots 320 are positioned and have sizes to guide tools used during the surgical procedure, similar to the slots 20, 120 of the guides 10, 110 described above. The slots 320 may have shapes and be positioned at a variety of angles to guide tools, including cutting tools. Each slot 320 may have a unique size and orientation. Thus, slots may be adapted to receive different tools, or only one specific tool. Features, such as protrusions, may be formed in the slot and interact with features of the tools to control the depth of insertion of the tool, direction of use of the tool, and insertion and removal points of the tool. Inserts, similar to the insert 24 described above, may be formed to be positioned in the slots 320 to prevent damage to the slots or to ensure proper use of tools during the procedure.

Although not illustrated, it will be appreciated that one or more cannula or bores may be associated with the guide 310. For example, in one embodiment, the guide includes a bore the same as, or similar to, the alignment channels 16, 116 described above.

Referring now to FIGS. 9A-9G, still another embodiment of a guide 410 of the present invention is illustrated. The guide 410 is adapted for use in pedicle subtraction osteotomies (PSO) and asymmetrical pedicle subtraction osteotomies (APSO) for a single vertebral level. The size and shape of the guide may be selected to fit the guide across the surface of the vertebra V.

The guide may comprise one piece adapted to target one portion of the vertebra. Alternatively, the guide may be formed in two or more pieces to target a variety of locations of the vertebra. The pieces can guide an ordered sequence of cuts in the vertebra. In one embodiment, the pieces may be interconnected in sequence during the surgical procedure to form the guide 410.

In one embodiment, the guide 410 may fit directly to the posterior aspects of a patient's anatomy, such as lamina, transverse processes, articular processes, spinous processes, etc. Accordingly, a variety of patient matching surfaces 414 may be provided on the guide. Additionally or alternatively, the guide 410 could also fit to a surface of the spine that has previously been cut. In one embodiment, the previous cut may be performed using an initial guide of the present invention. The initial guide is adapted to guide a cutting tool used to generate a surface of the vertebrae. The guide 410 may be designed to fit to the surface generated using the initial guide. Additional cuts in the altered vertebrae can then be performed using the guide 410. Alternatively, the guide 410 may be interconnected to a frame 330 as described above.

The guide 410 includes slots 420 to guide surgical tools, including cutting tools such as routers, burrs, and other similar device, along a track to aid in removal of pedicles. The slots 420 may be the same as, or similar to, the slots of guides 10, 110 described above. The slots have a size and orientation selected to constrain cutting tools to presurgically planned entry points and angles of cuts for the procedure. As will be appreciated, the slots may be oriented in a plane transverse to the proximal surface portion of the guide. The slots can be planned to guide tools to make cuts that are substantially linear, concave, convex, curvilinear, or "chevron" shaped. Further, as described above, the slots may receive sleeves and can include stops and keys.

Optionally, the guide 410 includes an alignment channel or cannula 416. The cannula 416 is adapted to guide a fixture tool or anchor, such as fixture 434, into the vertebra. It will be appreciated that the cannula 416 may be positioned in a variety of locations on the guide. Further, more than one cannula can be provided.

In one embodiment, as illustrated in FIGS. 9E-9G, the guide 410 is anchored to the vertebrae by an anchor 434. After the cuts 450 (illustrated in FIG. 9G) have been completed in the pedicle of the vertebrae V, the entire cut portion of the pedicle can be removed along with the guide 410 by pulling the anchor 434 away from the vertebrae V.

FIGS. 10A-10E illustrate another embodiment of a guide 510 of the present invention. In one embodiment, the guide 510 is adapted for use in PSO and APSO procedures. The guide is sized to partially span adjacent superior VS and inferior VI vertebrae. Similar to the guide 410 described above, guide 510 includes patient specific contact surfaces 514 adapted to substantially conform to the patient's anatomy. For example, in one embodiment, the distal surface 515 of the guide includes patient specific contours. At least one portion of the distal surface 515 may be adapted to contact a cut surface formed by removal of a portion of the patient's anatomy. A number of apertures may be formed through the guide to target, avoid, or align with, predetermined portions of the patient's anatomy.

An aperture 528 is formed through the guide 510. The aperture has a shape selected to allow the spinous process S to at least partially pass through the guide. Patient specific surfaces 514 may be formed within the aperture 528.

The guide further includes a pedicle aperture 529. The pedicle aperture 529 has a pre-planned shape to at least partially receive the pedicle P of the patient. The pedicle aperture may include interior surfaces that are patient specific. A surgeon may insert cutting tools into the aperture 529 to remove portions of the pedicle P. The pedicle aperture may be shaped to prevent over insertion of a tool into the vertebrae. Further, keys may be formed around the aperture 529. In conjunction with a protrusion formed on the tool, such as the protrusion 144 described above, the key may control or alter the depth of insertion of the tool as the surgeon move the tool around the aperture.

The guide 510 may also include a cutting track 520. The track 520 is similar to slots 20, 120 described above and may receive a guide sleeve, similar to sleeve 24. In one embodiment of the present invention, the cutting track 520 is adapted to target facet capsules of each of the superior VS and inferior VI vertebrae. The surgeon may use the cutting track 520 to separate the adjacent facet capsules of the adjacent vertebrae. As will be appreciated, other cutting tracks or cutting slots may be provided on the guide to control other planned cuts.

Although not illustrated, the guide 520 may include a cannula similar to cannula 16, 416 describe above. A fixture implanted in the vertebrae may be received in the cannula to at least temporarily interconnect the guide 520 to the vertebrae. Optionally, the cannula may be adapted to guide an instrument, including a boring instrument.

Referring now to FIGS. 11A-11E, still another embodiment of a guide 610 of the present invention is illustrated. The guide 610 is similar to guide 510. The distal surface 615 of the guide may include patient specific contact surfaces. At least one of the contact surfaces may be adapted to substantially conform to an unaltered portion of the patient's anatomy. Another portion of the distal surface may be adapted to substantially conform to a portion of the patient's anatomy altered, for example, by a cut. An aperture 628 adapted to at least partially receive the spinous process S may be provided. The aperture 628 may include patient specific surface 614.

The guide 610 is adapted to target each pedicle P of a vertebrae V. Accordingly, the guide includes two pedicle apertures 629. The apertures are the same as, or similar to, the pedicle aperture 529 of the guide 510 describes above. In one embodiment, each pedicle aperture 629A, 629B may have a unique shape specific to the patient's anatomy.

Voids 617 may also be formed in portions of the guide to align the guide with the vertebrae V. The voids may be in various positions. Further, the voids may extend partially or completely through the guide 610. In addition, a protrusion 619 may extend from the distal surface 615 of the guide. The protrusion may be adapted to fit to a selected portion of the posterior of the vertebrae. Optionally, the void or the protrusion may at least partially hook around a portion of the patient's anatomy. In this manner, the void 617 and protrusion 619 contact distinct portions of the patient's anatomy compared to other portions of the distal surface 615. The void and protrusion thus provide reference to indicate when the guide is positioned in a predetermined position in relation to the patient's anatomy. Said another way, the void 617 or protrusion 619 will prevent the guide 610 from seating properly when the guide is in an improper position. Thus, the guide will not be stable, providing tactile feedback to the user that the guide is not in the correct position. In one embodiment, the protrusion 619 is adapted to fit the guide to a portion of a transverse process or a lamina. Each void 617 or protrusion 619 may further include patient specific surfaces.

Referring now to FIGS. 12A-12C, a guide 710 of another embodiment of the present invention is illustrated. In one embodiment, the guide 710 is adapted for use in a PSO or an APSO procedure. Portions of the posterior of the superior vertebrae VS, medial vertebrae VM, and the inferior vertebrae VI (such as the transverse process, spinous process, lamina, and/or pedicles) are removed by cuts 750 prior to the use of the guide 710.

A frame 730 is interconnected a portion of the patient's spine. The frame generally comprises a medial member 732 connecting two transverse members 733. In one embodiment, the frame is interconnected to the superior vertebrae VS and the inferior vertebrae VI. Pedicle screws 734 positioned in the superior and inferior vertebrae may be used to secure the frame to the vertebrae.

The frame 730 may be similar to, and include the features of, the frame 330 described above. Thus, the frame 730 may preserve an existing amount of distraction. In one embodiment, the frame is used to preserve the relationship between the medial vertebrae VM and the adjacent superior and inferior vertebrae VS, VI. Alternatively, the frame is adjustable in order to change the distraction of the construct as necessary. For example, in another embodiment of the present invention, the medial member 732 of the frame may have a length that is adjustable during a surgical procedure. Changing the length of the medial member 732 increases or decreases the distance between the transverse members 733. The medial member 732 may comprise a first portion that fits within, or adjacent to, a second portion. The medial member may further comprise a rack and pinion system, threads, or other means for altering the length of the medial member to provide a desire amount of distraction between vertebrae VS, VM, VI.

As will be appreciated by one of skill in the art, the frame may have different shapes and sizes. For example, in another embodiment, the frame 730 may comprise two medial members. Each medial member 732 may have a length that is independently adjustable. Still other embodiments of the frame are contemplated for use with the guide of the present invention.

Once the frame is in place, the guide 710 is interconnected to the frame. In one embodiment, at least a portion of the guide 710 is adapted to contact a cut surface 750 of a patient's vertebrae. Another portion of the guide 710 may have patient-specific surface adapted to conform to an uncut portion of the patient's vertebrae.

The guide includes cutting tracks 720. The tracks 720 are similar to the other slots described herein, including, without limitation, slots 20, 120, 320. After the guide is interconnected to the frame, the tracks are used to guide cuts into the vertebrae along a predetermined trajectory. Each track 720A, 720B may have a unique patient specific shape. Further, track 720A may have a size and width adapted to receive a specific tool that is different than the tool associated with track 720B.

In one embodiment, the guide 710 includes two tracks to separate the pedicle from the medial vertebrae VM. The tracks may enable the separation of the pedicle in a single cut. The guide 710 may include apertures to guide cuts in other portions of the vertebrae VS, VM, and VI similar to guides 510, 610.

Although not illustrated, the guide 710 may also include cannula similar to cannula 16, 416 describe above. The cannula may receive a fixture interconnect the guide to the targeted vertebrae VM. Optionally, the fixture may be placed in a portion of the vertebrae, such as the pedicle, planned for removal by cuts guided by the tracks 720. In this manner, after the cuts are completed, the guide 710 can be removed from the frame to remove the severed portions of the pedicle. In another embodiment, the cannula is adapted to guide an instrument, such as a boring device.

Referring now to FIGS. 13-14, embodiments 810A, 810B of guides of embodiments of the present invention are illustrated. The guides are adapted fit to a cut surface 850 of a vertebrae VM that has been formed by removing a portion of the vertebrae. The surface 850 may be formed by a cut guided by another any other guide of the present invention. The guides 810A, 810B may also include patient-specific surfaces 814 that are adapted to substantially conform to predetermined portions of the vertebrae. A first portion 814A may be adapted to contact and substantially conform to a cut surface 850 of the patient's anatomy. A second portion 814B of the guide may include patient specific contours adapted to substantially conform to an unaltered portion of the patient's anatomy. The second portion 814B may generally hook around the patient's anatomy. In this manner, the second portion 814B contacts a different plane of the patient's anatomy compared to portion 814A.

The guides can have a variety of sizes and shapes. In one embodiment, the guides 810 have a size selected to fit at least partially across the surface of the vertebra. Additionally or alternatively, each guide may include armatures. The armatures may interconnect the guides 810 to a fixture, such as a screw, located in the vertebrae VM or in an adjacent superior or inferior vertebrae VS, VI. The armatures may also contact the vertebra in various locations. Further, the guides 810 may include a cannula similar to cannula 16, 116, 416. The cannula may receive a fixture to interconnect the guide to one of the vertebrae at least during the surgical procedure. Optionally, the cannula may be used to interconnect the guide 810 to a frame such as frames 330, 730. In another embodiment, the cannula are adapted to guide an instrument.

The guides 810 include slots 820 to target portions of the vertebrae. The slots may be the same as, or similar to, the slots of any other guide described herein. The slots may have any orientation and size. In one embodiment, the slots 820A, 820B are positioned in planes that are not parallel to each other. Each slot may have a unique size and may be associated with a specific tool. Further, the slots may receive sleeves, similar to sleeves 24, formed of a durable material, such as a metal, to prevent damage to the guide. The sleeves also prevent the cutting tool guided by the slot from changing the dimensions of the slot.

Although the guides 810 illustrated in FIGS. 13-14 include two slots, it will be appreciated that the guides may include any number of slots. Further, the guides may include slots to target both sides of a vertebra. In another embodiment, different guides 810 may be formed to target each of the posterior sides of the vertebrae. In this embodiment, the two guides for each side of the vertebrae may be keyed. The keys enable the guides to be interconnected together during the procedure. In this manner a guide can be assembled that targets both sides of the vertebrae while still protecting neural elements. The keys may optionally be adapted to require a specific assembly sequence of the individual guides.

A recess 854 is formed in a portion of the guides 810. The recess 854 has a cross-sectional shape selected to at least partially wrap around a neural element N, such as the spinal cord, of the patient. In one embodiment, the recess 854 has a shape similar to a "C" or a vaulted ceiling. The recess 854 includes an interior surface 856, illustrated in FIG. 13A, that is spaced from an interior surface of the slots 820. In this manner, the recess protects the neural element N from inadvertent damage as a tool is guided in the slot to form a cut in the vertebrae.

Referring now to FIG. 14, guide 810B is similar to guide 810A. Additionally, guide 810B includes a second recess 854A. The second recess is shaped to protect a second neural network, N2, such as a nerve root, from damage.

Referring now to FIGS. 15A-15E, another guide 910 of an embodiment of the present invention is illustrated. Guide 910 is similar to guides 810A, 810B. In one embodiment, the guide 910 is adapted for use to make final cuts 950 required during a pedicle subtraction osteotomy (or APSO).

The guide 910 generally comprises a radiused corner 958, a recess 954, and guide slots 920. After portions of the vertebrae have been removed exposing a neural network N, such as the spinal cord, the guide 910 is placed between the spinal cord the vertebrae VM. The radiused corner 958 of the guide is shaped to push the neural elements to create a space for the guide between the spinal cord and the vertebrae. The neural element N is then received in the recess 954 which protects the neural element from damage during cutting performed using the guide 910. The guide includes patient-specific features 914 that allow it to fit in a predetermined location. These features may match with the patient's anatomy (the anterior portion of the spinal canal) or may match to the cutting surfaces 950 generated with earlier guides.

The slots 920 are similar to slots of all embodiments of guides of the present invention described herein. Further, sleeves may be placed in the slots 920 to prevent damage or alteration of the slots by cutting tools used in the surgical procedure. The slots may align with previously completed cuts. In this manner, new cuts guided by the slots will intersect the previous cuts so that a portion of the vertebrae may be removed. In one embodiment, the slots 920 are aligned to complete a cut to remove a medial portion of the vertebral body. Although the slots 920 are illustrated on only one side of the guide, it will be appreciated that slots may be formed on each side of the guide. Further, the guide may include a bore or a cannula adapted to guide an instrument or fixation device.

Referring now to FIGS. 16-21, embodiments of models of the present invention are illustrated. The models are adapted for use during a surgical procedure, such as an osteotomy, as a reference for the surgeon. The method described in conjunction with FIGS. 1-2 may be used to form the models. For example, after the patient's anatomy is imaged, such as by CT image or other imaging device, a computer model of the anatomy is formed. The models may then be designed with patient-specific features and apertures or surfaces aligning with operations to be performed during the surgical procedure. The models include presurgically planned corrections to the patient's anatomy. For example, the models may include indications of angles and starting locations of multiple cuts required to make planned corrections to patient's alignment. The model can includes surfaces and indications aligning with cuts of any size and shape, including cut that are straight, concave, convex, curvilinear, or 'chevron' shaped. Further, the models can be designed to be modular such that separate portions are interconnected to form the finished model during a surgical procedure. This may be beneficial for models designed to fit around, or conform to, portions of the patient's anatomy with complex exterior contours.

The models are then manufactured by any method. In one embodiment, the models are manufactured using a rapid manufacturing process such as 3D printing, although other processes are contemplated. The models can be fit to the patient's anatomy during surgery to help the surgeon visualize the correct angles and starting locations for cuts, including osteotomy cuts. In one embodiment, the models include cannula. The cannula are adapted to receive fixtures adapted to at least temporarily interconnect the model to portions of the patient's anatomy. Fixtures may also be received in the cannula to interconnect portions of a modular model together.

Referring now to FIGS. 16A-16E, an embodiment of a model 1002 of the present invention is illustrated. The model 1002 is designed to include patient specific surfaces 1014 substantially conforming to a portion of the posterior surface of the vertebrae. In one embodiment, the model is adapted to at least partially fit around a portion of the vertebrae that is planned to be removed during the surgical procedure. In another embodiment, at least a portion of the model is adapted to substantially conform to, or "hook" to, a predetermined portion of the patient's anatomy, such as the vertebrae. Said another way, the model may be adapted to bias into a predetermined orientation with respect to the patient's anatomy. Accordingly, the material of the model 1002 may be selected to allow a surgeon bend or stretch the model 1002 to hook around the patient's anatomy. In one embodiment, the model 1002, or portions thereof, may be manufactured from a material that is at least partially flexible or deformable. In another embodiment, the model is manufactured from a material with shape memory, such as Nitinol. In this manner, when properly aligned with the patient's anatomy as planned, the model 1002 may be releasably retained in a predetermined alignment with respect to the patient's anatomy.

The model 1002 is adapted to indicate entry points and angles of the planned cuts. In one embodiment, the model includes indicia that indicated the entry points. In another embodiment, at least one exterior surface of the model is parallel to the plane of a planned cut. For example, in the embodiment of the model 1002 illustrated in FIG. 16E, exterior surface 1013 is substantially parallel to the plane of a cut planned to remove the spinous process S. Although not illustrated, the model may include slots and cannula to guide cuts and bores into portions of the vertebrae. As will be appreciated, the size and shape of the model 1002 may vary as planned to guide any variety of cuts. For example, if the thickness of the guide 1002 illustrated in FIG. 16E is increased, less of the spinous process S will be removed by a cut guide by surface 1013. In the alternative, more of the spinous process S can be removed by decreasing the height of the guide.

Referring now to FIGS. 17A-17F, still another model 1102 of the present invention is illustrated. Model 1102 is adapted for use in an asymmetrical pedicle subtraction osteotomy in one embodiment of the present invention. Model 1102 is similar to model 1002. Thus, the model may include indicia and other indications of entry points and angles of cuts. However, model 1102 further includes an aperture 1128 that fits around a portion of the vertebrae planned to be removed. In one embodiment, the aperture 1128 has a shape that is asymmetric around a vertical axis substantially parallel to the shorted sides of the model 1102. The aperture 1128 thus forms a window that indicates the bone intended for removal during the asymmetrical pedicle subtraction osteotomy. In one embodiment, proximal surface 1113 of the model 1102 is about parallel to the plane of a cut planned to remove a predetermined portion of the spinous process S.

As will be appreciated, the model and the aperture 1128 may be of any size and shape. The model also includes a variety of patient matched surfaces 1114 associated with portions of the patient's anatomy similar to the patient specific surfaces 1014 of model 1002. Further, the patient specific surfaces may be formed in voids 1117 formed in the model. The voids are adapted to align the model with the patient's anatomy. The model 1102 may further include projections 1119 with patient specific surfaces 1114 adapted to mate with portions of the patient's anatomy. The combination of voids 1117 and projections 1119 may decrease the possibility of improper placement of the model 1102 in relation to the patient's anatomy.

FIGS. 18A-18C illustrate a model 1102A of another embodiment of the present invention. Model 1102A is similar to model 1102. However, the aperture 1128A has a different shape that is substantially symmetric about a vertical axis. The aperture 1128A thus forms a window that indicates the bone intended for removal. As will be appreciated, the model and the aperture 1128A may be of any size and shape. In one embodiment, model 1102A is thicker than model 1102. Accordingly, model 1102A may be designed for a procedure in which less of the spinous process S is planned to be removed compared to in a procedure using model 1102.

The model 1102A also includes a variety of patient specific surfaces associated with portions of the patient's anatomy similar to the patient specific surfaces 1114 of model 1102. Further, voids and projections may be formed on the model 1102A similar to the voids and projections of model 1102 described above.

Referring now to FIGS. 19A-19E, still another model 1202 of an embodiment of the present invention is illustrated. The model 1202 generally comprises a first portion 1208 and a guide portion 1210. In one embodiment, the first portion and the guide portion are integrally formed as one piece. In another embodiment, portions 1208, 1210 are individual pieces adapted to be interconnected before or during a surgical procedure. The features 1260, 1262 are provided to align and interconnect the guide portion 1210 to the first portion 1208. In one embodiment, the features comprise projections 1260 formed on one of the portions adapted to be retained in bores 1262 formed in the other portion. Although the projections are illustrated on the guide portion and the bores are illustrated on the first portion, it will be appreciated the guide portion and the first portion may each comprise projections and corresponding bores. Further, other features adapted to interconnect portions 1208, 1210 are contemplated and may be used with the model of the present invention.

The first portion 1208 is similar to models 1002-1102 described above. Accordingly, the first portion generally includes patient specific surfaces 1214, voids 1217, protrusions 1219, and an aperture 1228 that are the same as or similar to the corresponding features of other models and guides described herein.

The guide portion 1210 generally includes tracks 1220 for guiding cutting tools, similar to the slots of all embodiments of the guides described herein. Thus, the tracks 1220 may be of any size and shape. Additionally, the tracks may be sized to receive sleeves and may include stops and keys to guide a direction of use of the cutting tool or limit the depth of insertion of the tool. Further, the tracks 1220 may have an asymmetric alignment.

Referring now to FIGS. 20-21, still more embodiments of models 1302A, 1302B of the present invention are illustrated. The models are adapted to dock to a frame 1330. The frame 1330 may be the same as, or similar to, the frames 330, 730 described above. Accordingly, models 1302 are adapted to fit with either pre-existing or planned pedicle screws 1334. The models may optionally contact a surface 1350 of the medial vertebrae VM prepared in a previous cutting procedure. However, as will be appreciated by one of skill in the art, the models are not required to contact the medial vertebrae.

The models 1302A, 1302B generally include apertures 1328 and voids 1317 for interconnection to the frame. In one embodiment, the model 1302A includes a closed aperture 1328. Accordingly, the model 1302A is generally interconnected to a medial portion of the frame 1330 before the frame is interconnected to the pedicle screws 1334.

Further, the models may include a recess 1354 similar to recess 854, 954 described above. The recess has a cross-sectional shape similar to at least partially wrap around a neural element, including the spinal cord of the patient. The models may also include indicia that indicate a location to begin a cut and an angle of the cut.

Model 1302A is generally comprised of two portions 1307A, 1307B. Each portion includes a leg or medial surface 1309 that indicates an angle of a planned cut. For example, medial surfaces 1309 are generally in a plane that is parallel to a place formed by a planned cut into the vertebrae. Thus, the space between portions 1307A, 1307B generally indicates the shape of a portion of the vertebrae VM that will be removed. In one embodiment, the medial surface 1309 includes a distal portion with patient specific contours 1314. The patient specific contours may substantially conform to a cut portion 1350 of the patient's anatomy. Optionally, the distal portion of medial surface 1309 may be adapted to contact and substantially conform to an uncut portion of the patient's anatomy.

In contrast, model 1302B comprises one piece. Angles of planned cuts are indicated by legs or exterior surfaces 1309 of the model 1302B proximate to the superior and inferior vertebrae VS, VI. Accordingly, the shape of the model generally indicates the shape of a portion of the vertebrae VM planned for removal. In addition, model 1302B has a void 1317 with an opening for interconnection to the frame 1330. Accordingly, the model 1302B may be added and removed from the frame without disassembling the frame 1330. In one embodiment, distal portions of the surface 1309 include patient specific contours 1314.

Referring now to FIGS. 22A-22F, still another embodiment of a model 1402 of an embodiment of the present invention is illustrated. Model 1402 is similar to model 2, described above in conjunction with FIG. 1. The model 1402 may be formed according to the method of FIG. 2 or by any other method.

Model 1402 is a patient specific three-dimensional model of grouping of vertebrae of the patient. The model is created for use in planning and performing a surgical procedure that includes removal of a section 1405 of the patient's spine. In one embodiment, the model is adapted for a spinal osteotomy procedure.

The section 1405 of the spine to be removed during the surgery is formed as a separate piece from other portions of the model. A handle may be interconnected to the removable section 1405. In this manner, the removable section 1405 may be separated from, or returned to, position in the model 1402.

The removable section 1405 may be used as a template or measurement jig during surgery. A portion of the removable section 1405A could be cut away to avoid contact with neural elements of the patient during surgery, as illustrated in FIG. 22C. The removed portion may conform to portions of the vertebrae of the patient removed during the surgery. Thus, the distal end of the modified section 1405A can be adapted to substantially align with surfaces of the target vertebrae.

The superior VS and inferior VI portions of the spine may also be formed as separate pieces. Thereafter the superior and inferior portions may be interconnected. In one embodiment, spine portions VS, VI are interconnected by a hinge 1464. However, it will be appreciated by one of skill in the art that other means may be used to interconnect the superior and inferior spine portions. For example, in another embodiment, a flexible member can be used to interconnect spine portions VS, VI. In another embodiment, a ball and socket joint may be provided to interconnect the spine portions VS, VI.

After the removable section 1405 of the model is withdrawn, the superior and inferior spine portions VS, VI can be repositioned, as illustrated in FIG. 22D, to demonstrate the corrected alignment of the spine provided by the procedure. The model 1405 may indicate that different, or additional, procedures will be required to correct a spinal abnormality.

To further visualize the alignment of the patient's spine before and after the planned procedure, indicators 1466A, 1466B may be interconnected to the superior and inferior spine portions VS, VI, respectively, as illustrated, for example, in FIGS. 22E-22F. In one embodiment, the indicators comprise rods with a curvilinear shape. It will be appreciated that the indicators may comprise different forms. The indicators simulate how the sagittal alignment of the patient's spine is altered by the presurgically planned osteotomy angles.

A variety of patient specific verification tools, illustrated in FIGS. 23-26, can be preoperatively planned and manufactured in order to aid in verifying final sagittal and/or coronal alignment and/or confirm screw placement. The verification tools are unique to each patient and may contain patient matching surfaces, implant contacting surfaces, and/or capability to mate with a guide. The verification tools of the present invention described in conduction with FIGS. 23-26 offer visual or tactical feedback to the surgeon during or after a surgical procedure.

Referring now to FIGS. 23-24, tools 1501A, 1501B of embodiments of the present invention are illustrated. The tools are adapted to verify coronal alignment during a surgical procedure. Said another way, the tools 1501 are used by a surgeon to verify that planned correction of the spine was substantially generated.

The tools 1501A, 1501B are designed using patient specific data and may be manufactured by any method. In one embodiment, the tools are designed and manufactured as described above in conjunction with FIGS. 1-2. The tools 1501 generally comprise armatures 1570 extending from a medial body 1572. The medial body 1572 simulates a planned coronal alignment.

Some of the armatures may be interconnected to portions of the patient's anatomy. In one embodiment, illustrated in FIGS. 23A-23D, the armatures may be interconnected to pedicle screws positioned in at least one of the ilium and the sacrum. In another embodiment, the tool 1501B is interconnected to only the sacrum.

The screws may be from a previous procedure or placed specifically to interconnect the tools 1501 to the patient's anatomy. Optionally, in another embodiment, the medial body includes patient specific contact surfaces selected to substantially match the posterior surface of the sacrum. Thus, the medial body 1572 may be retained on the sacrum with or without the use of pedicle screws.

An armature 1570A may be adapted to extend from the medial body to one or more superior vertebrae. The armature 1570A may have a non-linear shape adapted to substantially align with predetermined portions of the superior vertebrae when the planned correction of the spine is generated. In one embodiment, the armature 1570A is adapted to align with a posterior portion of the spinous processes S of number of superior vertebrae. Optionally, the armature 1570A may contact portions of the superior vertebrae when the planned correction is generated. In one embodiment, the tool 1501A comprises five armatures 1570 extending from the medial body 1572. In another embodiment, the tool 1501B includes three armatures 1570 extending from the medial body.

In another embodiment, the tool 1501 includes an electronic alignment indicator. The electronic indicator may comprise a light source or a laser aligned to produce a visible beam indicating the planned position of one or more vertebrae. The electronic indicator may be positioned in the medial body or on an armature.

Yet another embodiment of a tool 1601 of an embodiment of the present invention is illustrated in FIGS. 25A-25E. The tool 1601 is similar to tools 1501 and is also used to verify coronal alignment during a surgical procedure. The tool generally comprises an armature 1670 interconnected to a guide 1646. In one embodiment, the armature 1670 extends from a medial body 1672 of the guide. The medial body 1672 may include a fixture for interconnecting the armature 1670 to the guide 1646. The guide may be a sacroiliac guide. In one embodiment of the present invention, the guide 1646 is similar to guide 246 described above. Alternatively, in another embodiment, the guide is one of the guides described hereinafter in conjunction with FIGS. 27-33.

The armature 1670 may be integrally formed with the guide 1646. Optionally, the armature and the guide may be formed as separate pieces and interconnected before or during the surgical procedure. The curvilinear shape of the armature 1670 is adapted to indicate the planned sagittal and coronal alignment of patient's spine after the surgical procedure is completed, as illustrated in FIGS. 25D-25E. Similar to armature 1570A described above, the armature 1670 has a length selected to extend proximate to a number of superior vertebrae. The armature may have a shape that is proximate to, or contacts, portions of a number of vertebrae.

Referring now to FIGS. 26A-26B an embodiment of an alignment assembly 1700 of an embodiment of the present invention is illustrated. The assembly 1700 generally comprises armatures 1770 interconnected to a medial body 1772.

The medial body may have a predetermined shape and size. In one embodiment, the medial body 1772 has an arcuate shape. The medial body 1772 includes indicia 1774 that indicate a relative alignment of the patient's vertebrae. The indicia may comprise a series of lines. The lines may be graduated to indicate predetermined angles or distances. The medial body may be an existing tool, such as the scale of a protractor or a ruler. In one embodiment, the indicia 1774 include projections 1776 indicating a planned correction.

At least one of the armatures 1770 is moveably interconnected to the medial body 1772. In one embodiment, the armatures 1770 include a proximal portion forming a pointer. The pointer 1771 indicates the position of the armature on the indicia of the medial body 1772.

A distal portion of each armature is interconnected to fixtures (not illustrated) placed in vertebrae of the patient. The fixtures may comprise pedicle screws. Optionally, the armatures 1770 may have features adapted to be received directly in a cannula formed in vertebrae. In one embodiment, one armature is interconnected a medial vertebrae VM and a second armature is interconnected to a superior vertebrae VS. However, other interconnection locations of the armatures are contemplated. For example, in one embodiment of the present invention, one of the armatures 1770 is interconnected to a portion of the medial vertebrae VM.

In use, the alignment assembly 1700 may provide a first reading before the alignment of the spine is altered, as shown in FIG. 26A. After cuts 1750 are formed in the medial vertebrae VM, the alignment of the superior and inferior vertebrae VS, VI can be altered, drawing two cuts edges 1750 of the medial vertebrae VM closer together. A second reading of the alignment of the spine is then provided by the alignment assembly 1700, as shown in FIG. 26B.

Various apparatus formed by the system and method described above and that may be used for a particular fixation related surgery are depicted in FIGS. 27-33 and 40 which illustrate various embodiments of patient-specific guides of the present invention. The guides may be used for navigation of one or more of a cortical bone trajectory, a pedicle screw trajectory, and other trajectories in the spine of a patient. As will be appreciated by one of skill in the art, the cortical bone trajectory, unlike the pedicle screw trajectory, has a medial entry point and diverges superior and laterally (or "up and away") when advancing anteriorly through the pedicle. Additionally, the cortical bone trajectory allows for a greater amount of fixation in cortical bone as opposed to pedicle screw trajectories which achieve fixation mostly in cancellous bone. Each of the guides illustrated in FIGS. 27-33 and 40 can interface with any vertebra level or more than one vertebra level, including without limitation the cervical, thoracic, lumbar, and sacrum. Further, each of the guides include at least one cannulae. The cannulae may include a bore adapted to guide one or more guide wires, drill bits, taps, and screws. Optionally, a cannula may be devoid of a bore. The cannula without a bore is adapted to provide stability as other portions of the guide are used in a surgical procedure. Additionally or alternatively, the guides may comprise secondary and/or tertiary cannulae adapted to guide one or more of the group comprising guide wires, drill bits, taps, screws, couplings, and other instrumentation including without limitation tools adapted to harvest bone grafts. The cannulae may be of a variety of lengths. In one embodiment, at least a portion of the proximal end of the cannulae and the guide is configured to extend outside of the patient during a surgical procedure.

Any of the guides may include a track or slot adapted to guide an instrument operable to remove a predetermined portion of a vertebrae. The slot may include patient-specific depth control, angle, and orientation. Accordingly, any of the guides described in FIGS. 27-33 and 40 may include slots that are the same as, or similar to, slots 20, 120, 320, 420, 520, 720, 820, or 1220. In one embodiment, the slots are formed in place of bores of the guides.

The guides may further comprise the ability to accept one or more measurement devices for facilitating the surgeon/user in identifying landmarks, surrounding boney anatomy, placement of implanted devices, or for surgical planning Each of the guides may be adapted for use with a specific vertebrae of the patient. The guides may be formed according to the method of FIG. 2 or by any other suitable method. Any of the guides of FIGS. 27-33 and 40 may be used with, or include, tools, guides, wings, bodies, and patient-contacting surfaces. In one embodiment, at least a portion the guide is reusable.

Referring now to FIGS. 27-28 in detail, a patient-specific guide 1810 of an embodiment of the present invention is illustrated. The guide 1810 may comprise a spanning member or medial body 1812, arms 1814, a cannulae 1816, and a patient-matched leg 1824. In one embodiment of the present invention, the guide 1810 includes two arms 1814, two cannulae 1816, and two legs 1824. However, the guide 1810 of the present invention may include any number of cannulae and legs. The cannulae 1816 and legs 1824 may all have different lengths. Additionally, the angle and orientation of each cannulae and leg can be varied to match the anatomy of the patient, or to avoid a portion of the patient's anatomy. In one embodiment of the present invention, the cannulae 1816 have a generally cylindrical shape.

Although the guide 1810 illustrated in FIGS. 27-28 generally shows the cannulae 1816 and legs 1824 interconnected with two arms 1814, one of skill in the art will appreciate that the cannulae 1816 and legs 1824 may be interconnected in any number of ways. For example, in one embodiment, the cannulae 1816 may be interconnected by a curved medial body. Optionally, in one embodiment, the cannulae 1816 and legs 1824 may be formed as separate pieces that are individually located with respect to the patient's anatomy and then interconnected during the surgical procedure.

The cannulae 1816 are configured to contact one or more of the lamina, pars interarticularis, and aspects of the transverse process and the superior articular process of the patient. Cutouts 1817 may optionally be formed on a portion of the cannulae 1816 to prevent the guide 1810 from contacting the spinous process of the patient, or to avoid other patient anatomy. In alternate embodiments, cutouts 1817 may comprise one or more patient-matched surfaces or features for contacting in a complementary fashion the surrounding patient anatomy. In certain embodiments, cutouts 1817 may be oriented to achieve greater visibility to the surgeon/user, or to facilitate placement of one or more instruments or other devices as described herein. In further alternate embodiments, cutouts 1817 are not provided with the cannulae. In one embodiment, the cutouts 1817 may be adapted to provide a patient specific contour to match the spinous process or other unique patient anatomical feature and provide yet another surface for ensuring alignment and seating of the guide.

The cannulae may include a generally hollow bore 1820 adapted to guide instruments and fixation devices in the cortical trajectory. The bore 1820 of each cannulae 1816 can have an internal diameter that corresponds to a particular instrument or fixation device to prevent the use of the incorrect instrument or device. Thus, the dimensions of the bores of two cannulae may be different. The internal diameter of the bore 1820 may be selected to prevent the instrument or device from advancing into the cannulae 1816 beyond a predetermined distance, thereby providing a hard stop. Alternatively, a protrusion, key, notch, or void may be formed on the cannulae or in the bore to one or more of: prevent the use of the incorrect instrument or device; prevent an incorrect orientation of the correct tool or device; and prevent over insertion of the tool or device. For example, in one embodiment of the present invention, the cannulae bore 1820 may include an instrument contact surface, similar to the surface 122 of guide 110, that is associated with a feature of the tool, similar to the protrusion 144 of tool 140, to control the depth or orientation of insertion of the tool.

Further, the cannulae 1816 may have a varying length and may be made longer or shorter depending on the geometry of the cannulae 1816, the patient's anatomy, the purpose of the guide 1810, etc. For example, if a greater depth of a particular instrument or fixation device is required, the cannulae 1816 may be shorter to accommodate further penetration of the instrument or fixation device into patient's vertebrae.

Thus, the cannulae may be adapted to prevent the instrument or fixation device from advancing too far into the boney anatomy of the patient. For example, in one embodiment of the present invention, the bore 1820 of the cannulae 1816 may facilitate and guide a drill bit or any other suitable instrument to drill and tap a pilot hole in the cortical trajectory. Accordingly, in one embodiment, the cannulae 1816 is manufactured out of, or the bore 1820 is lined with, a metal or metal alloy that is of sufficient strength and brittleness that breaking and/or flaking is avoided. Further, at least the interior surfaces of the bore 1820 may withstand the effects of high-speed drilling without damaging the bore 1820 or the cannulae 1816 or permitting material from the cannulae 1816 to become deposited in the drilling site, as well as facilitating re-use of the cannulae. The material of the cannulae is also selected to withstand temperatures used to sterilize surgical instruments.

After the pilot hole is created, the bore 1820 may further guide insertion of a fixation device, such as a cortical screw (such as fixture 734 described above), into the pilot hole. In another embodiment of the present invention, the bore 1820 of the cannulae 1816 may be adapted to receive one or more inserts 1854 of varying lengths or a guide wire. The inserts 1854 may be sized with external diameters for mating with the interior diameter of the cannulae bore 1820. The insert 1854 may have an interior aperture 1856 running longitudinally through the insert for accommodating a drill bit or tap, for example, of varying sizes. In practice, the insert may facilitate and guide a drill bit for creating a pilot hole for further insertion of a fixation device, such as a screw.

As shown in FIG. 27E, the inserts 1854 may have a varying length, and may be made longer or shorter depending on the geometry of the guides 1810, the patient's anatomy, the purpose of the insert, etc. For example, if a greater depth of a particular drill is required, the insert 1854A may be shorter to accommodate further penetration of the drill bit into the patient's vertebrae. Likewise, the interior aperture 1856 of the insert 1854 may have varying diameter depending on the precise tool or instrument that is intended to be used with the insert. In this manner, a surgeon may ensure that he or she is using the proper tool, such as a drill or tap, with each of the inserts (which may further include one or more indicia to indicate the location or specific use intended for said insert) when performing a surgical procedure. For further illustration of the principles described above see inserts 1854C and 1854D which depict an insert with a 4.5 millimeter aperture 1856C diameter for placement of a tap instrument and a ⅛ inch aperture diameter 1856D for use in connection with a ⅛ inch drill bit, respectively.

The inserts 1854 described above may also include patient-specific contacting surfaces 1858, for further matching the insert 1854, in addition to the cannulae 1816, with the patient-specific anatomy. This allows greater stability and positioning of the insert 1854, and the cannulae 1816 with the insert 1854 included, in the proper location. In addition, for inserts 1854 used in connection with a drill bit or other vibrating or oscillating tool, these patient-matching surfaces 1858 would also prevent the distal end of the drill bit from "walking" or moving on the surface of the vertebral body when creating the initial pilot hole, thereby reducing the risk of incorrect trajectory of a fixation device.

The insert 1854E may further comprise a key or notch 1860 about one surface of the generally cylindrical body of the insert, which is configured to mate with a cutout or slot 1862 on the guide sleeve 1816 of the guide 1810. In this manner, the proper rotation/orientation of the insert 1854 is insured when guiding the insert into the cannulae bore 1820 of the guide sleeve cannulae 1816.

The insert 1854 may comprise a surgical drilling sleeves which may be used with a surgical guide according to an alternate embodiment of the present disclosure. Drilling sleeves are generally known in the art, however, the present embodiment relates to custom drill sleeves 1854F, 1854G which may be placed through one or more patient-matched inserts cannulae to provide contact with the boney surface at the distal end 1858 of the drilling sleeve. While custom drill sleeves 1854F, 1854G may be made of any material, in a preferred embodiment the sleeves are manufactured out of a metal or metal alloy that is of sufficient strength and brittleness that breaking and/or flaking of the drill sleeve material is avoided. Accordingly, the drill sleeves 1854F, 1854G may withstand the effects of high-speed drilling without damaging the sleeves 1854F, 1854G or permitting material from the sleeves to become deposited in the drilling site, as well as re-use of the drilling sleeves. The sleeves 1854F, 1854G must also withstand the high temperatures encountered during sterilization. Another benefit of metallic sleeves 1854F, 1854G is the ability to "trephine" or machine with a cutting surface to permit the distal end 1858G of the sleeve to "bite" into the bone and provide means for fixation.

The guide 1810 may include a patient-matched leg 1824 adapted to contact predetermined portions of the patient's anatomy. In one embodiment, the leg 1824 contacts one or more of the inferior articular process, lamina, and the transverse process. Optionally, the guide may include two or more legs. In one embodiment, the leg comprises a distal portion 1824A and a proximal portion 1824B. As will be appreciated, the legs 1824 may also extend from the cannulae 1816. For example, in one embodiment, the leg comprises only a distal portion 1824A extending from the cannula 1816.

Additionally or alternatively, patient-specific contact surfaces 1818, 1826 may be formed on any patient-contacting surfaces of the cannulae 1816 and/or the legs 1824, respectively. The surfaces 1818, 1826 provide a plurality of patient-specific contours for matching with a plurality of anatomical features. For example, the contours and locations of the lower, patient-contacting surfaces 1818, 1826 may be formed by use of data set(s) converted from a MRI, CT, or other imaging scan of the patient as described above in conjunction with FIG. 2. Further, the lower, patient-contacting surfaces 1818, 1826 may comprise dynamic contours having multiple compound radii. Accordingly, the surfaces 1818, 1826 are substantially congruent with the corresponding anatomical features of the vertebrae or other anatomical feature of the patient. Thus, the surfaces 1818, 1826 conform substantially to a predetermined surface of the anatomical feature of the patient where the cannulae 1816 and legs 1824 are to be located during the surgical procedure. Further, with surfaces 1818, 1826, the cannulae and legs would not conform substantially to a different surface of the anatomical feature. In this manner, the surgeon can determine if the guide 1810 is misaligned because the guide will not properly seat on the predetermined surface of the anatomical feature. In one embodiment, at least one of the surfaces 1818, 1826 is adapted to contact a surface of the patient's anatomy previously altered during a surgical procedure.

Further, the surfaces 1818, 1826 may contact or protrude around one or more of, but not limited to, the group comprising: the medial side of the inferior articular process, the lateral sides of the lamina, the junction between the pars and the transverse process, and other anatomical features of the patient. These patient-contacting surfaces 1818, 1826 help position the guide 1810 and keep it in position in a predetermined position and orientation. By protruding at least partially around different portions of the patient's anatomy, the surfaces 1818, 1826 generally hook at least partially around the patient's anatomy. Thus, the surfaces may contact at least two different planes formed by distinct surfaces of the patient's anatomy.

The guide 1810 may further comprise slots 1830 formed in the medial body 1812, arms 1814, cannulae 1816, or the legs 1824. The slot 1830 may be a cutting slot to direct the path of a blade or other cutting instrument as will be appreciated by one of skill in the art. In other embodiments, the slot 1830 may be adapted to receive a measurement aid or tool for facilitating the surgeon/user in identifying landmarks, surrounding boney anatomy, placement of implanted devices, or for surgical planning.

Alternatively, the slot 1830 may be adapted to receive one or more secondary or tertiary cannulae 1840, 1850 as further described in conjunction with FIG. 33. In certain embodiments, the tertiary cannulae 1840, 1850 may further comprise a patient-matched surface or feature for contacting a particular patient anatomical surface or feature. In alternate embodiments, the tertiary cannulae are generally smooth and do not comprise patient-matched surfaces or features.

Optionally, in one embodiment of the present invention, illustrated in FIG. 27D, a cutting guide 10 may be interconnected to the guide 1810A. The cutting guide 10 may be the same as, or similar to, the cutting guides 10, 110 illustrated and described in conjunction with FIGS. 3-6. The guide 10 generally includes a slot 20 adapted to guide a cutting tool. The slot 20 can have any shape determined to guide cuts for a planned surgical procedure for a particular patient. Further, the slot may comprise multiple portions adapted to guide more than one different cut or more than one instrument. The cutting slot 20 may be sized or shaped to receive a particular cutting tool and to prevent the use of an inappropriate tool. Additionally, the slot may be shaped to guide a cut around a neural element of the patient or to prevent a cut into a neural element. The slot 20 may include stops adapted to limit or control the depth of insertion of a cutting tool. Similar to other slots described herein, the slot 20 may be specific to the patient's anatomy. In one embodiment, the slot 20 continues through a portion of the guide 1810A. Said another way, the slot 20 is adapted to prevent contact by a tool or instrument positioned in the slot with other portions of the guide.

The cutting guide 10 may be integrally formed with the guide 1810A. Alternatively, in another embodiment of the present invention, the cutting guide 10 may be releasably interconnected to the guide 1810A. In this manner, the cutting guide 10 may be added to, or removed from, the guide 1810A during a surgical procedure.

The cutting guide 10 may be interconnected to any portion of the guide 1810A. In one embodiment, the cutting guide 10 is interconnected to at least one of a leg 1824 and a cannula 1816 of the guide 1810A. Optionally, the cutting guide 10 may be interconnected to an arm 1814 or the medial body 1812. As will be appreciated, the cutting guide 10 and slot 20 may have any predetermined orientation with respect to the guide 1810A. Thus, the cutting guide 10 or the slot 20 may be rotated in any orientation other than the orientation illustrated in FIG. 27D.

Optionally, as illustrated in FIG. 27D, a cannula 1816A of the guide may be devoid of a bore. The cannula 1816A has a shape and size to provide stability as bore 1820 or cutting slot 20 are used to guide instruments during a surgical procedure.

According to one embodiment, the guide 1810 may further comprise one or more indicia for identifying the guide for a particular patient, a level of the patient's spine, or other indicia indicating the direction, orientation, use, or purpose of the guide. The guide 1810 may take on other shapes, orientations, thicknesses, etc. without deviating from the novel aspects of this disclosure. Similarly, guide 1810 may be of any size and may comprise extensions or handles to aid in grasping or manipulating the guide 1810 as desired.

Referring now to FIGS. 29A-C, another patient-specific guide 1910 of an embodiment of the present invention is illustrated. The guide 1910 comprises a medial body 1912 and at least one cannulae 1916. In one embodiment, the guide 1910 is formed as two separate pieces that may be individually positioned in contact with a predetermined feature of the patient's anatomy and then interconnected during the surgical procedure. The two portions 1912A, 1912B of the medial body are adapted be interconnected. In one embodiment, the medial body 1912B includes a coupling 1913 adapted to releasably interconnect the individual pieces of the guide 1910 together. Accordingly, in one embodiment, the two portions of the guide may be interconnected by positioning the coupling 1913 in a corresponding void in medial body 1912A. The coupling may be held in the void by friction. Additionally or alternatively, a biasing force may be provided to retain the coupling 1913 in the void. In one embodiment, the coupling and void comprise a snap. In another embodiment, the medial body may include magnets. Optionally, in still another embodiment, the medial body portions 1912A, 1912B may be interconnected by a flexible or expandable member, such as a hinge or a biasing member of any type, including a spring. It will be appreciated by one of skill in the art that the medial body portions 1912A, 1912B may be interconnected by any other suitable means. Optionally, in another embodiment of the present invention, the guide 1910 is formed as one integral piece.

The cannulae 1916 are the same as or similar to the cannulae 1816 described above in conjunction with FIGS. 27-28. In one embodiment, the cannulae 1916 has a generally cylindrical shape. In like manner, the cannulae 1916 are configured to contact one or more of the patient's lamina, pars, and aspects of the transverse process and the superior articular process or other portions of the patient's anatomy. The cannulae may be formed without a bore. In another embodiment, the cannulae 1916 may include a bore 1920 similar to bore 1820. The bore 1920 comprises a predetermined internal diameter that is adapted to receive a particular instrument or fixation device to prevent the use of the incorrect instrument or device. The internal diameter of the bore 1920 may be selected to prevent the instrument or device from advancing into the cannulae 1916 beyond a predetermined distance, thereby providing a hard stop. Additionally, the bore 1920 may have a shape adapted to align the tool or fixation device in a predetermined orientation of use.

Further, the cannulae may be of any length based at least in part on the specific patient's anatomical features, preferences of the surgeon, orientation of the guide 1910, and the type of tool or fixation device associated with the cannulae 1916.

Thus, the cannulae may be adapted to prevent the instrument or fixation device from advancing too far into the boney anatomy of the patient or otherwise being misused. For example, in one embodiment of the present invention, the bore 1920 of the cannulae 1916 may facilitate and guide a drill bit or any other suitable instrument to drill and tap a pilot hole in the cortical trajectory. After the pilot hole is created, the bore 1920 may further guide insertion of a fixation device, such as a cortical screw, into the pilot hole. In another embodiment of the present invention, the bore 1920 may be adapted to receive one or more inserts 1854 or guide wires in a manner similar to that illustrated and described in conjunction with FIGS. 27-28, above.

Additionally or alternatively, patient-specific contact surfaces may be formed on any patient-contacting surfaces 1918 of the cannulae 1916 and/or the contacting surfaces 1926 of the medial body 1912. The surfaces 1918, 1926 provide a plurality of patient-specific contours for matching with a plurality of anatomical features, as described in greater detail above. The surfaces 1926 of the medial body 1912 may contact at least the front of the spinous process. The surfaces 1918 of the cannulae 1916 are adapted to contact or protrude around one or more of, but not limited to, the group comprising: the medial side of the inferior articular process, the lateral sides of the lamina, the spinous process, and the junction between the pars and the transverse process, and other anatomical features of the patient. These patient-contacting surfaces 1918, 1926 help position the guide 1910 and keep it in position in a predetermined position and orientation.

Although not illustrated in FIG. 29, the guide 1910 may further comprise slots formed in the medial body 1912 or the cannulae 1916. The slots may be the same as or similar to slots 1830. The slots are adapted to direct the path of a blade or other cutting instrument in a manner similar to cutting slots 20-820 of all embodiments described above. Alternatively, the slots of guide 1910 may be adapted to receive one or more secondary or tertiary cannulae as further described in conjunction with FIG. 33. The guide 1910 may take on other shapes, orientations, thicknesses, etc. without deviating from the novel aspects of this disclosure. For example, the guide 1910 may include one or more legs similar to legs 1824. The legs may extend from one or more of the medial body 1912 and the cannulae 1916. In one embodiment, at least one of the cannulae include a lower leg portion 1824A. Similarly, guide 1910 may be of any size and may comprise extensions or handles to aid in grasping or manipulating the guide 1910 as desired. In another embodiment, the guide 1910 is adapted to receive a cutting guide 10 in a manner similar to guide 1810A illustrated in FIG. 27D.

Referring now to FIGS. 30A-B, a patient-specific guide 2010 of still another embodiment of the present invention is illustrated. The guide 2010 generally comprises a cannulae 2016 and one or more legs 2024.

The cannulae 2016 is the same as or similar to the cannulae described above in conjunction with FIGS. 27-28. Although only one cannulae 2016 is illustrated in FIG. 30, it will be appreciated by one of skill in the art that the guide 2010 may have any number of cannulae. The cannulae 2016 includes a bore 2020 similar to bores 1820, 1920. The bore 2020 comprises a predetermined internal diameter to receive a particular instrument or fixation device. Accordingly, the bore 2020 may prevent the use of the incorrect instrument or device and prevent to incorrect use of the instrument or device. Thus, the internal diameter of the bore, the shape of the bore, and/or a feature formed on or in the bore may be selected to prevent the instrument or device from advancing into the cannulae 2016 beyond a predetermined distance, thereby providing a hard stop. The length of the cannulae 2016 may also be increased or decreased based at least in part on the instrument or device associated with the cannulae 2016, the orientation of the guide with respect to the patient's anatomy, and preferences of the surgeon. Thus, the cannulae may be adapted to prevent the instrument or fixation device from advancing too far into the boney anatomy of the patient. For example, in one embodiment of the present invention, the bore 2020 of the cannulae 2016 may facilitate and guide a drill bit or any other suitable instrument to drill and tap a pilot hole in the cortical trajectory. After the pilot hole is created, the bore 2020 may further guide insertion of a fixation device, such as a cortical screw, into the pilot hole. In another embodiment of the present invention, the bore 2020 may be adapted to receive one or more inserts 1854 or guide wires in a manner similar to that illustrated and described above.

Additionally or alternatively, the cannulae 2016 may include a second bore. The second bore may be oriented in a different for placement of a temporary fixation device. Optionally, the cannulae may include a track or slot adapted to guide an instrument operable to remove a predetermined portion of a vertebrae. The slot may include patient-specific depth control, angle control, and orientation. The slot may be the same as, or similar to, any of the slots described herein. For example, the slot may be similar to slots 20, 120, 320, 420, 520, 720, 820, or 1220.

In one embodiment of the present invention, the cannulae 2016 has a length such that the distal or terminal end 2018 of the cannulae 2016 does not contact the patient's anatomy. Said another way, the terminal end 2018 of the cannulae 2016 is adapted to float above a predetermined portion of the patient's anatomy. In another embodiment of the present invention, the cannulae 2016 has a different length such that the terminal end 2018 of the cannulae 2016 intentionally contacts a predetermined portion of the patient's anatomy. Continuing this example, patient-specific contact surfaces may be formed on the terminal end 2018 of the cannulae 2016. Thus, the terminal end 2018 of the cannulae 2016 may optionally provide still another guide surface to align and/or stabilize the guide 2010 in a predetermined orientation during a surgical procedure.

The legs 2024 of the guide 2010 may each comprise a different length. Additionally, the position and alignment of the legs 2024 with respect to the cannulae 2016 may vary based on patient specific anatomical features, a panned orientation of the guide 2010, or a preference of the surgeon. The legs 2024 are adapted to contact predetermined portions of the patient's anatomy. In one embodiment, one or more of the legs 2024 may be adapted at least partially conform to, or hook around, a predetermined portion of the patient's anatomy. Accordingly, the guide 2010, or portions thereof, may be made of a material selected to allow a surgeon bend or deform the guide 2010 to fit around the patient's anatomy. In one embodiment, the legs 2024, or portions thereof, are manufactured from a material that is at least partially flexible or deformable. In another embodiment, at least a portion of the legs 2024 are manufactured from a material with shape memory, such as Nitinol. In this manner, the guide 2010 may be aligned with the patient's anatomy by a surgeon as planned with at least a portion of a leg 2024 hooked around the patient's anatomy. Accordingly, the legs may provide a bias force to releasably retain the guide 2010 in a predetermined alignment with respect to the patient's anatomy.

In one embodiment of the present invention, the guide 2010 comprises three patient-matched legs 2024 adapted to create a patient specific surface to align the cannulae 2016 in a predetermined orientation. However, it will be appreciated by one of skill in the art that the guide 2010 may include any number of legs 2024.

Although illustrated in FIG. 30 as having a generally linear shape, it will be appreciated by one of skill in the art that one or more of the legs 2024 may have a curvilinear shape. Thus, the shape, length, and orientation of the legs may be customized to contact predetermined portions of the patient's anatomy while avoiding contact with other features of the patient's anatomy or to prevent obstruction of the surgeon's view during a surgical procedure. Accordingly, in one embodiment, at least one of the legs includes a curved shape, or a cutout similar to cutouts 1817 described above in conjunction with FIGS. 27-28, to prevent unintended or inadvertent contact between the guide 2010 and the spinous process or another anatomical feature of the patient. Alternatively, in another embodiment, at least one of the legs may include a curved shape or cutout with patient-matched surfaces adapted to create still another patient specific contact surface to one or more of align and stabilize the guide 2010.

In one embodiment, at least one of the legs 2024 contacts one or more of the group comprising the inferior articular process, lamina, superior articular process, the transverse process, and another anatomical feature. The terminal ends 2026 of the legs 2024 may include patient-specific contact surfaces the same as or similar to contact surfaces 1826, 1926 described above in conjunction with FIGS. 27-29. Additional patient specific contact surfaces may also be formed on one or more other surface of the legs 2024. Although not illustrated, the contact surfaces 2026 may include protrusions adapted to one or more of: align the guide 2010 in a predetermined position with respect to the patient's anatomy, hook around a portion of the patient's anatomy, prevent unintended or inadvertent movement of the guide 2010 during a surgical procedure, and displace soft tissue. In one embodiment, the contact surfaces 2026 comprise relatively thin extensions. The contact surfaces 2026 may contact or protrude around one or more of the medial side of the inferior articular process, the lateral sides of the lamina, the junction between the pars and the transverse process, and the superior articular process. Optionally, at least one of the contact surfaces 2026, or a portion of one of the legs, may be adapted to contact a surface of the patient's anatomy that has been altered during a surgical procedure.

Although not illustrated in FIG. 30, the guide 2010 may further comprise slots formed in one or more of the cannulae 2016 and the legs 2024. The slots may be the same as or similar to slot 1830 and adapted to direct the path of a blade or other cutting instrument in a manner similar to the slots described above. Alternatively, the slots of guide 2010 may be adapted to receive one or more secondary or tertiary cannulae as further described in conjunction with FIG. 33. The guide 2010 may take on other shapes, orientations, thicknesses, etc. without deviating from the novel aspects of this disclosure. For example, in one embodiment of the present invention, one leg 2024 may extend from another one of the legs 2024. Similarly, guide 2010 may be of any size and may comprise extensions or handles to aid in grasping or manipulating the guide 2010 as desired. Further, the guide 2010 may be adapted to interconnect to a frame, such as frame 330, 730, 1330. In another embodiment, the guide 2010 may interconnect to a frame prior to, or after, one or more of the guides 310, 710, 1302. In this manner, the guide 2010 may be used in conjunction with one or more of guides 310, 710, 1302 without placing additional fixtures in the patient's anatomy.

Various guides as described herein may be provided to facilitate or control a device (by way of example, a screw) entry point, angular trajectory, height, and/or head orientation. This is desirable particularly with placement of screws, as it permits the surgeon/user to optimize spinal screw head alignment for subsequent rod insertion across multiple boney landmarks. Additionally, by controlling screw placement, a patient specific rod (described in more detail below) may be designed and manufactured to either match the pre-planned screw placement, or offer angular corrections in order to optimize curvature of the spine. Additional benefits of the various guides described herein include improving device fixation, and/or preventing unwanted contact between devices and patient anatomy (e.g. the patient's spinal cord). The further use of methods described above, including the use of software analytics, may further aid in determining screw placement and orientation to achieve the ideal screw placement and/or rod shape. For example, the use of various guides described herein to achieve desired screw head placement and orientation in turn provides improved alignment or a secondary device, such as a rod (described in more detail hereinafter), with the screws heads. This benefit in turn allows the surgeon/user to achieve optimal sagittal and/or coronal alignment, which assists in rod placement and improves correction of the patient's anatomy.

Referring now to FIGS. 31A-C, another patient-specific guide 2110 of another embodiment of the present invention is illustrated. The guide 2110 generally comprises a medial body 2112 and at least one cannulae 2116.

The medial body 2112 comprises a distal surface 2113 adapted to contact predetermined portions of the patient's anatomy. In one embodiment, the distal surface 2113 is adapted to contact one or more of the group comprising the inferior articular process, lamina, spinous process, pars, the transverse process, and other features of the patient's anatomy. Thus, the distal surface 2113 of the medial body 2112 provides a patient specific surface to align the guide 2110 in a predetermined orientation. Optionally, one or more of the lateral surfaces 2111 may have patient specific shapes adapted to contact, or interconnect to, other portions of the patient's anatomy. For example, the guide 2110 may include extensions or legs, similar to legs 2024, adapted to hook around, portions of the patient's anatomy. The legs may be made of a flexible or deformable material, including Nitinol. In one embodiment, the legs are adapted to provide a bias force to "hook" the guide in a predetermined orientation with respect to the patient's anatomy.

Further, the surface 2113 may comprise two or more surfaces 2113A, 2113B adapted to contact different portions of the patient's anatomy. Accordingly, the surfaces 2111, 2113A, 2113B can form a complex shape selected to provide a substantially tight fit of the guide 2110 to the patient's anatomy to one or more of: prevent unintended or inadvertent movement of the guide 2110 during the surgical procedure and position the guide 2110 in a predetermined position with respect to the patient's anatomy. The distal surface 2113 may further include a relief portion 2115 to prevent unnecessary contact with the patient's anatomy to avoid unnecessary or unintended tissue dissection or damage. Optionally, one or more of the surfaces 2111, 2113A, 2113B may have a shape or protrusion adapted to displace soft tissue.

The cannulae 2116 is the same as or similar to the cannulae described above in conjunction with FIGS. 27-30. It will be appreciated by one of skill in the art that the guide 2110 may have any number of cannulae. In one embodiment of the present invention, the guide 2110A includes two cannulae 2116, 2116A. Further, the cannulae may each have a different orientation to target different portions of the patient's anatomy. The cannulae generally pass from the proximal surface of the guide 2112 to the distal surface 2113. Further, although illustrated protruding from the proximal surface of the guide 2112, one of skill in the art will appreciate that the cannulae 2116 may terminate at a point substantially level with the proximal surface of the guide. Additionally, the cannulae may have any predetermined orientation with respect to the medial body 2112 of the guide 2110. In one embodiment, the cannulae has an orientation that passes through the proximal surface and the distal surface of the guide. In another embodiment of the present invention, at least one end of the cannulae 2116A passes through a lateral surface 2111 of the guide 2110.

The cannulae 2116, 2116A include a bore 2120 similar to bores 1820, 1920, 2020. The bore 2120 comprises a predetermined internal diameter or shape to receive a particular instrument or fixation device. Accordingly, the bore 2120 may prevent the use of the incorrect instrument or device. The bore 2120 may also be adapted to prevent the improper use of an instrument or device. Thus, the internal diameter or the shape of the bore 2120 may be selected to prevent the instrument or device from advancing into the cannulae 2116 beyond a predetermined distance, thereby providing a hard stop. In this manner the cannulae may be adapted to prevent the instrument or fixation device from advancing too far into the boney anatomy of the patient. For example, in one embodiment of the present invention, the bore 2120 of the cannulae 2116 may facilitate the placement of one or more of a guide wire, securing element, and a pin in a cortical trajectory. In one embodiment, the bore 2120 facilitates the placement of a guide wire that may be used to guide drills, taps, and fixation devices such as screws. The guide wire may be a K-wire known to those of skill in the art. The guide 2110 may further be adapted to receive a sleeve or an insert as described above.

During a surgical procedure, two or more guides 2110 may be used. As illustrated in FIG. 31C, each guide may be positioned in contact with different portions of the patient's anatomy. Further, although not illustrated in FIG. 31, the individual guides 2110B, 2110C can be interconnected together before or during the surgical procedure. Accordingly, in one embodiment of the present invention, guides 2110B, 2110C include a structure similar to the medial body 1912 described above in conjunction with FIG. 29 adapted to releasably interconnect the guides together. In another embodiment, the guides 2110B, 2110C include a structure similar to the arm 1814 to permanently interconnect the guides together.

Although not illustrated in FIG. 31, the guide 2110 may further comprise slots formed in the medial body 2112. The slots may be adapted to direct the path of a blade or other cutting instrument in a manner similar to cutting slot as will be appreciated by one of skill in the art. Alternatively, the slots of guide 2110 may be adapted to receive one or more secondary 2140 or tertiary cannulae 2150 as further described in conjunction with FIG. 33. The guide 2110 may take on other shapes, orientations, thicknesses, etc. without deviating from the novel aspects of this disclosure. For example, the guide 2110 may include one or more legs similar to legs 1824, 2024. Similarly, guide 2110 may be of any size and may comprise extensions or handles to aid in grasping or manipulating the guide 2110 as desired.

In one embodiment, the guide 2110 may be interconnectable to a frame similar to guide 2010. Accordingly, the guide 2110 may be used with one or more frames 330, 730, 1330 before, or after, one or more of guide 310, 710, 1302, and 2010.

Referring now to FIGS. 32A-C, a patient-specific guide 2210 of yet another embodiment of the present invention is illustrated. The guide 2210 generally comprises a medial body 2212, a cannulae 2216, one or more legs 2224, and a second leg or bridge 2230.

The cannulae 2216 may be the same as or similar to the cannulae described above in conjunction with FIGS. 27-31. Although two cannulae 2216 are illustrated in FIG. 32, it will be appreciated by one of skill in the art that the guide 2210 may have any number of cannulae. Further, each cannulae 2216 has a predetermined length that may be shorter or longer than the length of a different cannulae of the guide. The cannulae 2216 may include a bore 2220 similar to bores 1820, 1920, 2020, 2120. The bore 2220 comprises a predetermined internal diameter adapted to receive a particular instrument or fixation device. Accordingly, the bore 2220 may prevent the use of the incorrect instrument or device. The shape and/or the internal diameter of the bore 2220 and the length of the cannulae 2216 may be selected to one or more of: prevent the instrument or device from advancing into the cannulae 2216 beyond a predetermined distance, prevent the use of the incorrect instrument or device, and ensure proper alignment and use of the correct instrument or device. Thus, the cannulae may be adapted to prevent the instrument or fixation device from advancing too far into the boney anatomy of the patient. For example, in one embodiment of the present invention, the bore 2220 of the cannulae 2216 may facilitate and guide a drill bit or any other suitable instrument to drill and tap a pilot hole in the cortical trajectory. After the pilot hole is created, the bore 2220 may further guide insertion of a fixation device, such as a cortical screw, into the pilot hole. In another embodiment of the present invention, the bore 2220 may be adapted to receive one or more inserts of any variety of sizes. The inserts, described above, may facilitate and guide a drill bit or other tool, such as a tap.

Optionally, in one embodiment of the present invention, a sleeve may be inserted into the bore 2220 of the cannulae 2216. The sleeve may be similar to the sleeves 24 and inserts 1854 described herein and may be comprised of the same or similar materials. The sleeve may have an outer-diameter that is at least slightly greater than the interior diameter of the cannulae bore. Accordingly, the sleeve may be held in position within the bore by a press fit. In one embodiment, the sleeve cannot be removed after insertion within the bore. In this manner, it is possible to prevent miss-use of the cannulae bore. Alternatively, the sleeve may be used to sequence the use of tools and instruments associated with the cannulae. For example, in one embodiment, the cannulae bore may have an internal diameter or shape adapted to receive a first tool. A sleeve may have a bore with an internal diameter or shape adapted to receive a second tool. The sleeve bore may prevent insertion of the first tool. In this manner, the sleeve will prevent use of the first tool at an inappropriate or unintended time. Further, when the sleeve has an outer diameter that prevents removal of the sleeve from the cannulae bore, the sleeve prevents use of the first tool after the sleeve bore has been used to guide the second tool.

In one embodiment, the sleeve is adapted for use with an instrument. In another embodiment, the interior diameter of the sleeve bore is substantially equal to the outer diameter of the sleeve. Thus, the sleeve may be very thin. In still another embodiment, the sleeve bore may include keys, tracks, or protrusions adapted to guide a feature on an exterior surface of an instrument received by the cannulae. The sleeves may be sized to fit within the bore of an cannulae described herein.

In one embodiment of the present invention, the cannulae 2216 have a length such that the distal or terminal ends 2218 of the cannulae 2216 do not contact the patient's anatomy. Said another way, the terminal ends 2218 of the cannulae 2216 are adapted to float above predetermined portions of the patient's anatomy. In another embodiment of the present invention, one or more of the cannulae 2216 have a length such that the terminal end 2218 of the cannulae 2216 intentionally contacts one or more of the lamina, pars, the transverse process, the superior articular process of the patient, and a different anatomical feature of the patient. Continuing this example, patient-specific contact surfaces may be formed on the terminal end 2218 of the cannulae 2216 as well as other surface of the cannulae. Thus, the terminal ends 2218 of the cannulae 2216 and other surfaces may optionally provide still other guide surfaces to align and/or stabilize the guide 2210 in a predetermined orientation during a surgical procedure.

The legs 2224 of the guide 2210 may each comprise a different length. Additionally, the position and alignment of the legs 2224 with respect to the cannulae 2216 may vary based on patient specific anatomical features or the surgeon's preference. The legs 2224 are adapted to contact predetermined portions of the patient's anatomy. In one embodiment of the present invention, the guide 2210 comprises two patient-matched legs 2224 adapted to create a patient specific surface to align the cannulae 2216 in a predetermined orientation. However, it will be appreciated by one of skill in the art that the guide 2210 may include any number of legs 2224.

Although illustrated in FIG. 32 as having a generally linear shape, it will be appreciated by one of skill in the art that one or more of the legs 2224 may have a curvilinear shape. Thus, the shape, length, and orientation of the legs may be customized to contact predetermined portions of the patient's anatomy while avoiding contact with other features of the patient's anatomy. Accordingly, in one embodiment, at least one of the legs includes a curved shape, or a cutout similar to cutouts 1817 described above in conjunction with FIGS. 27-28, to prevent unintended or inadvertent contact between the guide 2210 and the spinous process, the lamina, or another anatomical feature of the patient. Alternatively, in another embodiment, at least one of the legs 2224 may include a curved shape or cutout with patient-matched surfaces (similar to surfaces 1926 described above in conjunctions with FIG. 29) adapted to create other patient specific contact surfaces to one or more of align and stabilize the guide 2210.

In one embodiment, at least one of the legs 2224 contacts one or more of the group comprising the inferior articular process and the lamina. The terminal ends 2226 of the legs 2224 may include patient-specific contact surfaces the same as or similar to contact surfaces 1826 described above in conjunction with FIGS. 27-28. Additional patient specific contact surfaces may also be formed on one or more other surface of the legs 2224. Although not illustrated, the contact surfaces 2226 may include protrusions adapted to one or more of: align the guide 2210 in a predetermined position with respect to the patient's anatomy, prevent unintended or inadvertent movement of the guide 2210 during a surgical procedure, and displace soft tissue. In one embodiment, the contact surfaces 2226 comprise relatively thin extensions.

The second legs or bridge 2230 is adapted to contact one or more of the spinous process and the lamina of the patient. In the embodiment of the present invention illustrated in FIG. 32, the bridge 2230 extends medially from the cannulae 2216. In another embodiment, the bridge 2230 extends medially from the legs 2224. The bridge 2230 may be formed as a single piece and include a longitudinal cavity. The longitudinal cavity may be formed by use of data set(s) converted from an MRI or CT scan of the patient as described above in conjunction with FIG. 2. In this manner, the longitudinal cavity is adapted to substantially mate with the contours of a predetermined portion of the patient's anatomy. In one embodiment, the longitudinal cavity is adapted to contact the contours of the spinous process of a particular vertebral body of the patient. In another embodiment, the bridge 2230 is formed of two separate portions 2230A, 2230B. In all embodiments of the present invention, the bridge 2230 includes one or more contact surfaces 2234 adapted to mate with the contours of one or more of the spinous process, the lamina, and other anatomical features. Thus, the bridge 2230 facilitates one or more of ensuring a predetermined alignment of the guide 2210 and preventing inadvertent or unintended movement of the guide 2210 during a surgical procedure.

The guide 2210 may also include extensions adapted to hook at least partially around, or too, a portion of the patient's anatomy. For example, in one embodiment of the present invention, one or more of the medial body 2212, the legs 2224, and the bridge 2230 may have a shape adapted hook to the patient's anatomy. In another embodiment, a portion of the guide 2210, such as one of the legs, medial body, or the bridge, may comprise a flexible or bendable material as previously described. In use, a surgeon may bend or alter the guide 2210 to hook to the patient's anatomy.

Although not illustrated in FIG. 32, the guide 2210 may further comprise slots formed in one or more of the medial body 2212, the cannulae 2216, and the legs 2224. The slots may be the same as or similar to slot 1830 and adapted to direct the path of a blade or other cutting instrument in a manner similar to cutting slot described above. Alternatively, the slots of guide 2210 may be adapted to receive one or more secondary or tertiary cannulae 2240, 2250 as further described in conjunction with FIG. 33. As will be appreciated, the guide 2210 may also include a cutting guide 10. The cutting guide 10 may be interconnected to any portion of the guide 2210, similar to the cutting guide 10 illustrated in FIG. 27D.

The guide 2210 may take on other shapes, orientations, thicknesses, etc. without deviating from the novel aspects of this disclosure. For example, in one embodiment of the present invention, one leg 2224 extends from another one of the legs 2224. In another embodiment, at least one of the legs 2224 extends from the medial body 2212. Similarly, guide 2210 may be of any size and may comprise extensions or handles to aid in grasping or manipulating the guide 2210 as desired.

Referring now to FIG. 33, still another embodiment of a patient-specific guide 2310 of an embodiment of the present invention is illustrated. Guide 2310 is substantially the same as guide 1810 described above in conjunction with FIGS. 27-28. Accordingly, the guide 2310 may comprise a medial body 2312, arms 2314, cannulae 2316, and patient-matched legs 2324 the same as or similar to body 1812, arms 1814, cannulae 1816, and patient-matched legs 1824 of guide 1810. In one embodiment of the present invention, the guide 2310 includes two arms 2314, two cannulae 2316, and two legs 2324. However, the guide 2310 of the present invention may include any number of cannulae and legs. The cannulae 2316 and legs 2324 can each have different lengths. Additionally, the angle and orientation of each cannulae and legs can be varied to match the anatomy of the patient.

The guide 2310 may further comprise slots 2330 formed in one or more of the medial body 2312, arms 2314, cannulae 2316, and the legs 2324. The slots 2330 may be cutting slots to direct the path of a blade or other cutting instrument as described above. Alternatively, the slots 2330 may be adapted to receive one or more secondary 2340 or tertiary cannulae 2350.

The secondary and tertiary cannulae 2340, 2350 may be positioned in the slots 2330 to target a predetermined portion of one or more of a second level and a third level anatomical feature of the patient. In one embodiment, the cannulae 2340, 2350 are adapted to target one or more predetermined portions of the cervical spine (i.e., C1-S1 and ilium). The cannulae 2340, 2350 include a bore 2320 the same as or similar to bores 1820, 1920, 2020, 2120, and 2220 described above in conjunction with FIGS. 27-32. Accordingly, the bore 1820 can guide one or more of a guide wire, a drill bits, a tap, a fixation device (such as a screw), and other instrumentation, including without limitation, tools for harvesting bone grafts. Further the bore and/or the cannulae 2340, 2350 may have a length, shape, protrusion, and/or a diameter selected to prevent the use of the improper tool or device, prevent improper use of a predetermined tool or device, and ensure proper use of the predetermined tool or device.

Optionally, in another embodiment of the present invention, the secondary and tertiary cannulae 2340, 2350 may include a track or slot. The slot may be adapted to guide an instrument operable to remove a predetermined portion of a vertebrae. The slot may include patient-specific depth control, angle control, and orientation. In one embodiment of the present invention, the slot of the cannulae 2340, 2350 is the same as, or similar to, any of the slots described herein. For example, the cannulae 2340, 2350 may include a slot similar to slots 20, 120, 320, 420, 520, 720, 820, or 1220.

The ends of the cannulae 2340, 2350 may include patient specific contact surfaces as previously described in conjunction with FIGS. 27-32. Additionally, the angle and orientation of each cannulae 2340, 2350 can be varied to match the anatomy of the patient. The tertiary cannulae 2350 may be interconnected to a secondary cannulae 2340. The cannulae 2340, 2350 may be releasably interconnected to the guide 2310 before or during a surgical procedure. The cannulae 2340, 2350 may include an extension 2344 or multiple extensions 2344A to engage the slots 2330 formed on the guide 2310. Each of the slots 2330 may have a different shape, width, depth, and orientation adapted to receive a predetermined cannulae 2340, 2350 in a specific orientation. Alternatively, in one embodiment, the cannulae 2340, 2350 are formed with the guide 2310 as one integral piece.

With respect to the embodiments shown and described in relation to FIGS. 35-39, a variety of mechanical characteristics may be incorporated into coupling devices and rods without departing from the spirit of the disclosure made herein. Applicant incorporates by reference U.S. Patent Publication No. 2009/0105760 in its entirety, which is co-pending and names Dr. George Frey as the sole inventor, for the purpose of further supplementing the disclosure and providing additional support for various mechanical characteristics capable of being employed in the coupling device. In addition, methods of forming and shaping rods used in surgical procedures are disclosed in U.S. Pat. Nos. 9,044,285, 8,721,651, 8,607,603, 8,549,888, 8,540,719, 8,298,242, 7,957,831, 7,454,939, 6,644,087, 6,221,077, 6,035,691, 6,006,581, 5,490,409, U.S. Pat. Pub. No. 2015/0127053, U.S. Pat. Pub. No. 2015/0047410, U.S. Pat. Pub. No. 2014/0137618, U.S. Pat. Pub. No. 2013/0110174, U.S. Pat. Pub. No. 2008/0086127, U.S. Pat. Pub. No. 2007/0227216, U.S. Pat. Pub. No. 2005/0262911, U.S. Pat. Pub. No. 2004/0243481, U.S. Pat. Pub. No. 2004/0144149, WIPO Pub. No. WO 2014/143762, WIPO Pub. No. WO 2014/088801, and WIPO Pub. No. WO 2009/035358 which are each incorporated by reference in their entirety to further supplement and provide additional support to the present disclosure.

Referring now to FIGS. 35-39, embodiments of patient-specific rods and methods of forming and shaping the rods are described. More specifically, locations of fixation devices (e.g. pedicle screws, cortical bone screws, spinal hooks) to be used in a surgical procedure is determined. The locations of the fixation devices includes, but is not limited to, entry point of each fixation device, the trajectory and orientation of each fixation device, and the size and type of the fixation devices. The trajectory may be determined from the use of scanning equipment described above, and selected based on optimal patient anatomy, bone density, etc. The diameter, size, and height of the rod or other implant is considered when determining the locations of the fixation devices. The entry points and locations of each fixation device are mapped in three dimensions in reference to a given origin. Screw head location may be with or without correction of the patient's abnormality.

The map of the fixation devices is used to presurgically plan the contours of a rod. The rod planning can be conducted manually by a surgeon or technician or automatically conducted by a software algorithm that uses information such as angles, lengths, radii, etc. to generate the optimal correction for a patient. The rod planning may also consider a surgeon's preferred "textbook" or preferred correction as well as physical limitations of the patient's anatomy (e.g. resistance from soft tissue).

The rods 2420 may have any size or shape for any planned surgical procedure. Rods of a different shapes, sizes, and materials may be used together in one surgical procedure. In one embodiment, at least one rod has a generally cylindrical shape. In another embodiment, a rod has at least one generally planar surface. In yet another embodiment, a rod 2420 has a cross-sectional configuration that is one of: V-shaped, W-shaped, polygonal-shaped, and tapered. In one embodiment, the rod is a spinal fusion rod. However, one of skill in the art will appreciate that the rods and methods of forming them described herein may be used in conjunctions with other surgical procedures.

The map of the fixation devices is used to form a rod for use in the surgical procedure. In one embodiment of the present invention, a patient specific rod that is pre-bent is manufactured. The patient specific rod has a shape substantially aligning with the head or tulip of each screw trajectory included in the map of the fixation devices. The patient specific rod can be manufactured or formed by any suitable method, including by a 3D printer (SLA or SLS as a template, out of metal, polyetheretherketone (PEEK), or any other material suitable for use in an implant for a patient), manufactured using a rod bending machine (out of metal to be used as template or implant), machined, or manufactured using an equivalent process. In one embodiment of the present invention, the patient specific rod is manufactured using the method described above in conjunction with FIG. 2. In another embodiment, the patient specific rod is designed using a computer aided design (CAD) process.

The patient specific rod has a shape that substantially aligns with the planned locations and orientations of screw heads intended to interconnect the rod to the patient's anatomy. The patient specific rod can be planned to be produced with bends or contours in three dimensions to match a planned contour of the patient's spine. In one embodiment the patient specific rod only matches the patient's pre-operative anatomy and the planned screw locations. This allows the surgeon to induce any desired correction by making additional bends to the baseline (pre-operative) curvature of the rod. In another embodiment of the present invention, the patient specific rod substantially matches the planned screw locations and also accounts for preoperatively planned correction of the patient's deformity (accounting, for example, for sagittal and/or coronal alignment of the patient's spine). Optionally, the surgeon may manually reshape the patient specific rod to generate any additional desired correction to the patient's spine.

In another embodiment, the map of the fixation devices is used to manufacture a rod template as described above in conjunction with FIG. 2. The rod template has a shape substantially matching the planned locations and orientations of the screw heads. A generic rod is then manually re-shaped by the operator to substantially conform to the rod template and form a patient specific rod. In one embodiment, the rod template includes a recess adapted to receive the generic rod. In another embodiment, the rod template includes a number of protrusions adapted to receive the generic rod which is then bent to align with the planned screw locations. In one embodiment, the generic rod has no patient-specific contours before being manually re-shaped.

Figure 34A:
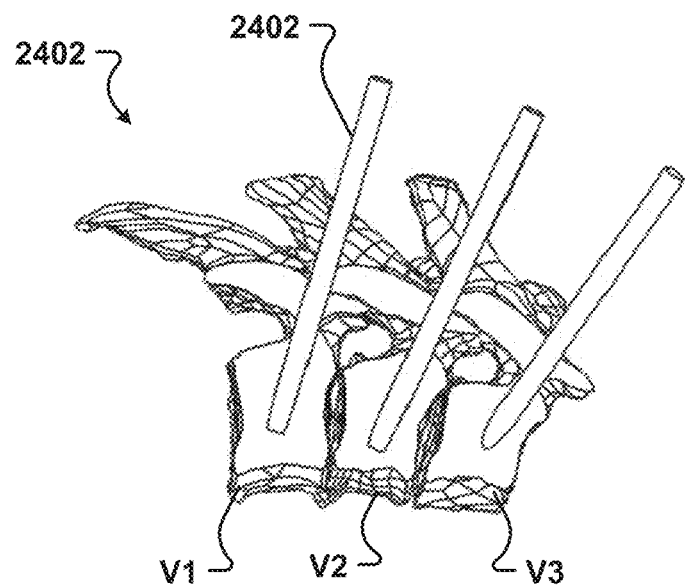
Figure 34B:
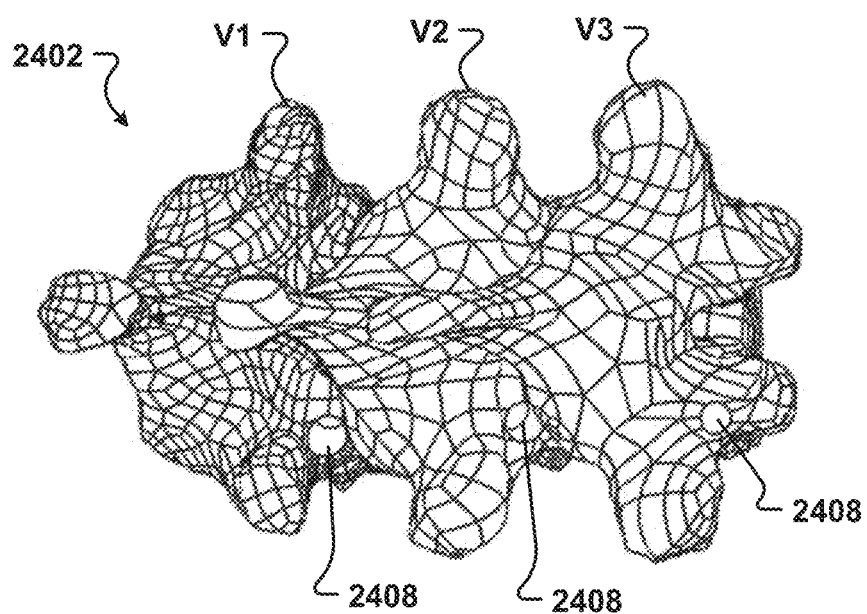

Referring now to FIGS. 34A-34B, a patient-specific bone model 2402 of one embodiment of the present invention is used to form a rod 2420 prior to, or during, a surgical procedure. The model 2402 is generated from patient imaging data (CT, MRI, etc.) and converted to 3D CAD or FEM models. The data for the model may also be captured by an optical system.

Here, the underlying anatomy is a portion of the patient's spine. Although only three vertebrae V1-V3 are included, the model 2402 may include any number of the patient's vertebrae. Further, one of skill in the art will appreciate that the model 2402 may be made to represent any predetermined portion of the patient's anatomy. The model may include a reproduction of the deformity associated with these levels of the patient's spine.

The model 2402 provides a user with both a visual and tactile representation of the patient's anatomy for creating a patient-specific rod, including one or more predetermined screw trajectories. During design of the model, cylindrical members 2404 may be used with the model 2402 to represent planned screw trajectories. The user may manipulate the members 2404 during the design of the model to change the location and trajectory of each screw.

The modeling of predetermined screw trajectories assists in the orientation and placement of the rod. Further, the model 2402 may help the surgeon determine the shape and length of the rod necessary to correct the patient's deformity as well as different positions and alternate arrangement of the planned screws. By using the model 2402, a user may also identify changes to the shape of the rod necessary to correct the patient's anatomy.

Planned screw locations and trajectories may be simulated by bores 2408 in the model 2402. Each screw may have a different planned trajectory. Although the bores 2408 are illustrated with a generally cylindrical shape, it will be appreciated by one of skill in the art that the bores 2408 may have any predetermined shape. Further, the bores 2408 may have a predetermined depth and diameter. In one embodiment, each bore has a unique cross-section. In another embodiment, the screw trajectories are designed using generic cylinders in the CAD system.

After the screw trajectories and locations are determined, the model 2402 is generated. In one embodiment of the present invention, the model is formed using any 3D printing process or rapid prototyping process as will be appreciated by one of skill in the art. In another embodiment, the model 2402 may be formed as describe above in conjunction with FIG. 2. In still another embodiment, the vertebra V1-V3 of the model 2402 are flexibly interconnected to enable movement of the model 2402.

Figure 34C:
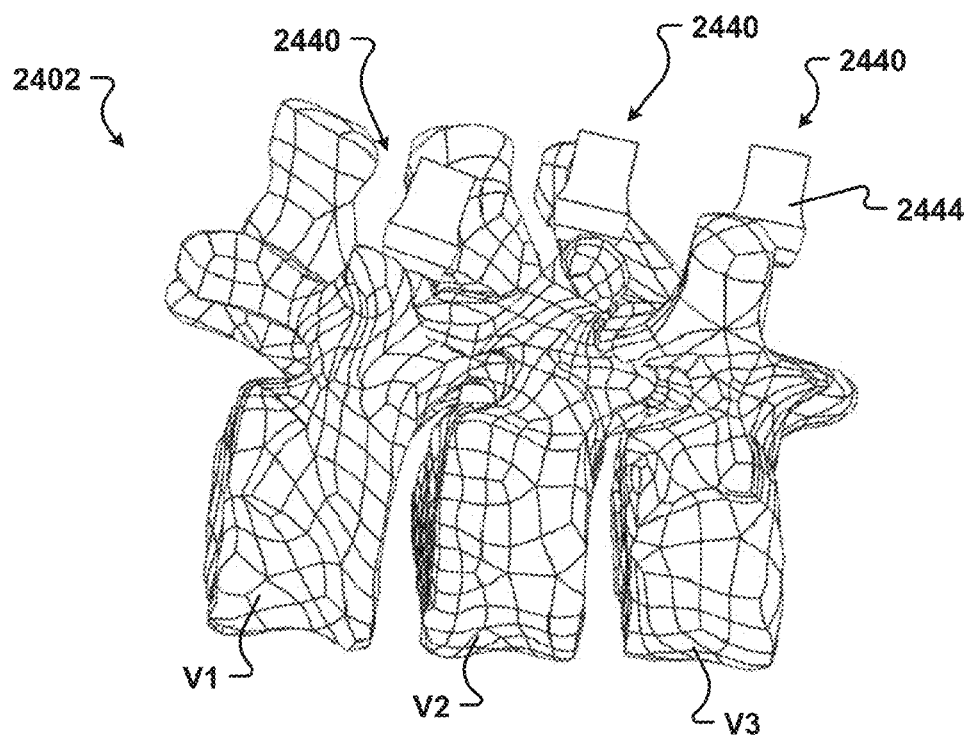
Figure 34D:
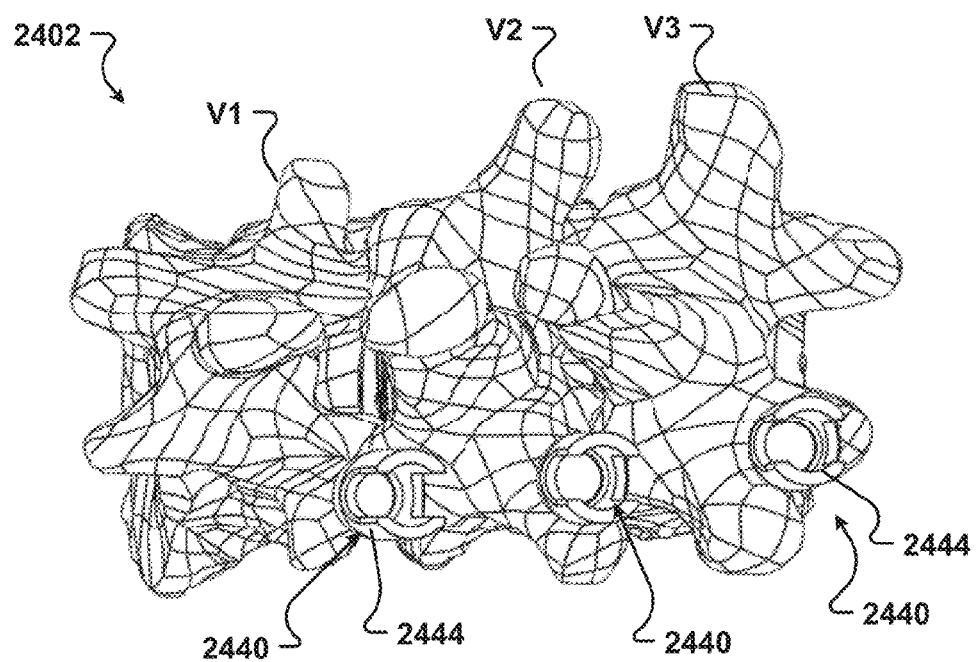

Referring now to FIGS. 34C-34D, one or more pegs 2440, described in more detail below in conjunction with FIG. 36, may be positioned in the bores of the model 2402. The positions of the pegs 2440 and the orientation of the peg head 2444 may be altered to adjust the planned screw orientation. For example, the body of one or more of the pegs 2440 may be advanced or withdrawn at least partially in the bore 2408 to alter the location of the peg head 2444. Alternatively, the pegs 2440 or the heads 2444 may be rotated or pivoted with respect to the model 2402. Further, a peg with a different size body may be used to change the planned shape of the rod. Optionally, in one embodiment of the present invention, the pegs 2440 may be integrally formed with the bone model 2402 with the heads 2444 in a predetermined position.

Figure 34E:
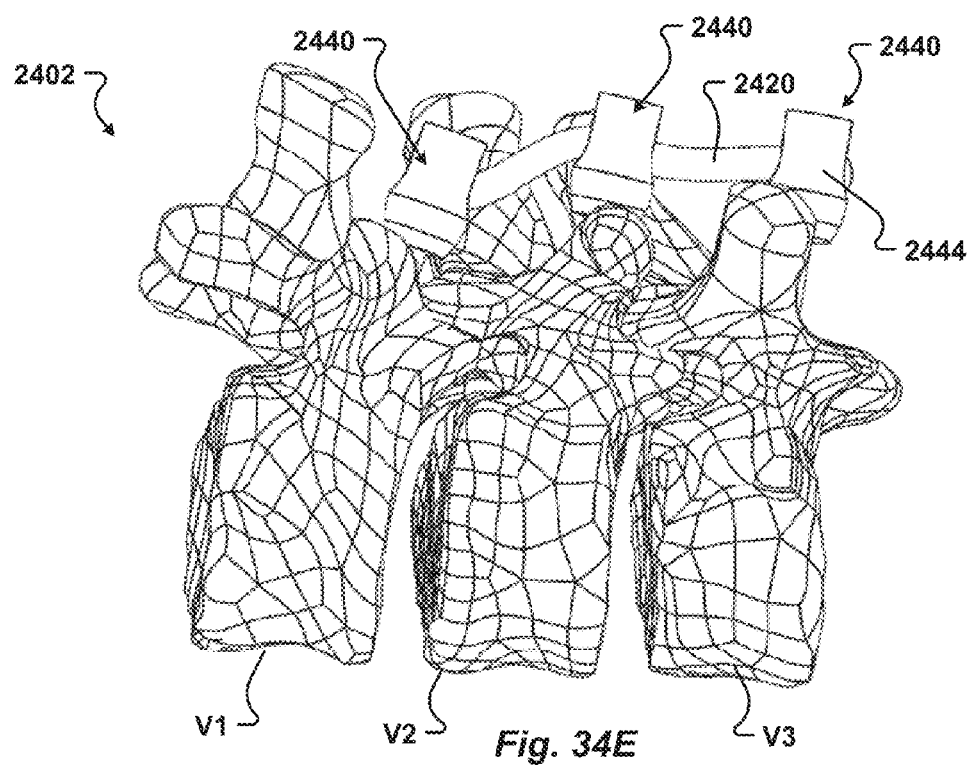
Figure 34F:
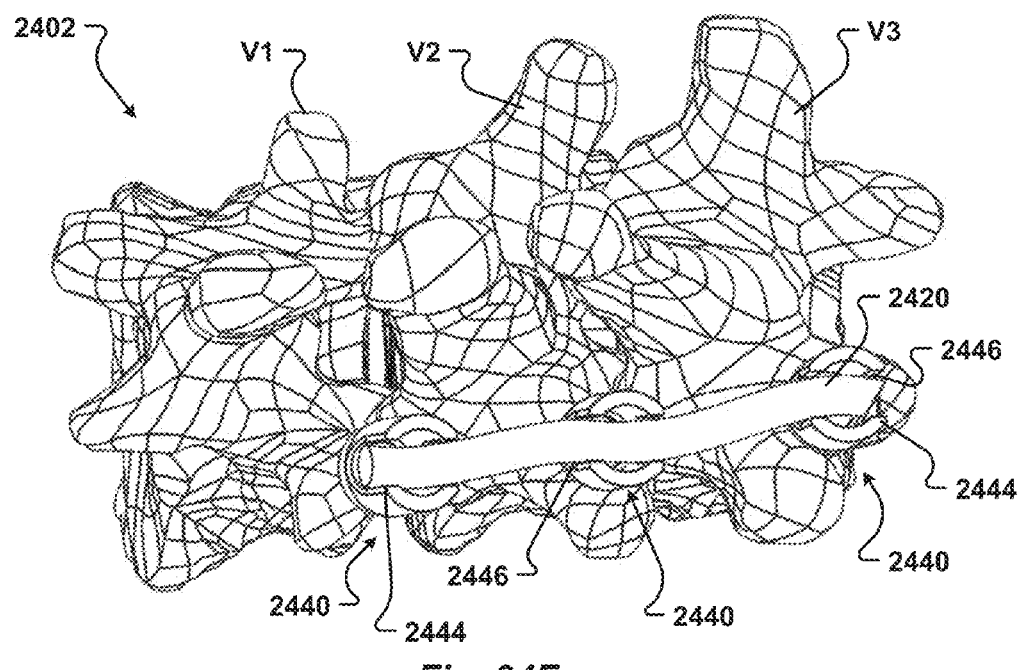

Referring now to FIGS. 34E-34F, the model 2402 with the pegs 2440 is used as a template by the surgeon (or other operator) to presurgically bend rods 2420 to the planned shape. Placing the rod 2420 on the model 2402 as illustrated in FIGS. 34E-34F permits the surgeon to determine the length and orientation (including curvature) of the fixation rod required to correct the deformity or otherwise treat the patient. The model 2402 may also assist the user in other aspects of the surgical procedure. For instance, placing the rod on the model allows the surgeon to visualize the difference in height of each level of the patient's spine and differences from one level to the next and also allow the user to visualize whether the rod is misaligned or requires modification to correct the patient's deformity. For example, the surgeon may identify unwanted contact between the patient's anatomy and either the screws or the rod.

The surgeon may also receive tactile feedback when placing the rod on the model 2402, such as a clip or snap when the rod is properly aligned with, and received by, the pegs. As described above, the model 2402 may be flexible to reproduce movement of the patient's spine. When the rod is placed on the model, the surgeon can move the model to determine if rod and screws optimally correct the patient's deformity.

The surgeon can use the model 2402 to preoperatively generate desired correction in the rod for either a generic rod or a patient specific rod. For example, as previously described, a generic rod may be bent by the surgeon until it fits substantially in the planned screw locations represented by the heads 2444 of the pegs 2440. The generic rod is bent by any suitable method as will be appreciated by one of skill in the art. In one embodiment, after the generic rod 2420 is bent it is retained within the recesses 2446 of the heads 2444. Thus, when adjusted to the appropriate shape, the rod may "click" into place and can be locked once the user has finished their adjustments to achieve optimal fit and correction of the patient's anatomy.

Alternatively, the rod may be a patient specific rod manufactured with bends pre-formed to substantially match the shape of the rod to the planned screw locations. For example, as illustrated in FIGS. 34E-34F, the patient specific rod 2420 may align with the planned screw locations without further adjustment by the surgeon. However, after placing the patient specific rod on the model 2402 with the pegs, the surgeon may determine that the shape of the rod should be further adjusted. This can be accomplished by removing the rod 2420 from the model 2402 and bending the rod by any method. In one embodiment, the rod may be bent manually by the surgeon's hands. In another embodiment, a tool may be used to bend the rod. The surgeon may manipulate the rod 2420 and move the vertebrae V1-V3 of the model 2402 to visualize the correction in the model itself until the desired alignment of the vertebrae is achieved. The rod 2420 may then be used in a surgical procedure.

Referring now to FIG. 35A, a configurable template 2502 according to an embodiment of the present invention is illustrated. The template 2502 includes peg holders 2508 adapted to retain pegs 2440 is predetermined positions. The pegs 2440 represent the positions and orientations of fixation implants, such as screws, in the map of fixation devices planned to be used in a surgical procedure. The location, orientation, and height of each peg may be adjusted using the template 2502. The pegs 2440 can have various lengths and configurations in order to account for the height and orientation of each planned screw. The heads 2444 or entire pegs 2440 may be rotated to simulate planned placement of spinal fixation devices.

In one embodiment peg holders 2508 protrude from the surface of the template 2502 and the pegs 2440 fit onto the holders. In another embodiment, the peg holders 2508 comprise a plurality of voids sized to receive at least a portion of a peg. In one embodiment, the holders 2508 are arranged in a grid of rows and columns. In one embodiment, the template 2502 is a generic device, such as a peg-board. In another embodiment, the pegs may be slidingly retained by the template. Thus, the position and alignment of one or more of the pegs may be altered by the user. In still another embodiment, the template may be modeled within a CAD system. The coordinates and sizes of the pegs may then be modeled in the CAD system. When an appropriate amount of correction is provided by a rod by the pegs, the data related to the pegs are saved in the CAD system. The pegs and rod, or rod template, may then be manufactured as described below.

Referring now to FIG. 35B, pegs 2440 are arranged in predetermined positions on the template 2502 according to the planned surgical positions of the screws. A sufficient number of pegs necessary to provide inflection points of the rod in three-dimensional space may be used with the template 2502. In one embodiment, arranging the pegs on the template comprises preparing a map to identify the location and trajectory of each screw. The map is used to determine entry points of the planned trajectory of each of the screws. The entry points are mapped in three dimensions in reference to a given origin. The coordinates and height of the entry points is used to orient the pegs on the template 2502 to substantially duplicate the presurgically planned screw trajectory for a specific patient.

In one embodiment, the screw map is created using a CAD or FEM program or other planning tool. The location of the entry points can then be exported as a CAD file and re-mapped into a second CAD file containing the template 2502. By referencing the origin of the entry points to a given location within the template file, the entry point locations can be oriented such they have a known location in relation to the template 2502.

In another embodiment, the template 2502 and pegs 2440 are manufactured after the screw map with the screw locations and orientations has been created. The template 2502 is then manufactured with a number of peg holders 2508 in the positions of the planned screw locations. The number of peg holders may be equal to the number of screws planned to be used in the surgical procedure. Each peg holder 2508 may have a unique cross-sectional profile corresponding to the cross-sectional profile of a corresponding portion of the body of one of the pegs 2440. Further, each peg may have a unique length and head orientation. In one embodiment, the length and head orientation of the pegs is determined from the screw map. In this manner, each peg 2440 may be placed in the correct location and orientation.

When the pegs are in the predetermined arrangement on the template 2502, the template can be used to adjust a rod 2420 as illustrated in FIGS. 35C-35E. A surgeon or other user can then change the orientation or location of one or more of the pegs 2440. The surgeon may then bend the rod 2420 to correspond to the new positions of the pegs 2440 to change the shape of the rod 2420. Each rod 2420A, 2420B may have unique contours and a different length and size.

The rod 2420 can be a generic rod, described above, that is bent to substantially align with the heads 2444 of the pegs. When the generic rod is substantially aligned with the heads, it will fit with the planned screw trajectories without further correction. However, the surgeon can change the shape of the rod 2420, for example, to alter the amount of correction provided by the rod.

Alternatively, the template 2502 can be used to modify the shape of a pre-manufactured patient specific rod. When the pegs are arranged on the template according to the screw map, the patient specific rod will substantially align with the heads of the pegs. In one embodiment of the present invention, the patient specific rod is retained in recesses 2446 of the heads 2444. Thus, the patient specific rod will fit with the planned screw trajectories without manual bending by the surgeon. However, as described above, the surgeon may optionally change the shape of the patient specific rod as necessary, desired, or for any other reason.

Referring now to FIG. 36, pegs 2440 of embodiments of the present invention are illustrated. The pegs are used with used in conjunction with the models 2402 and templates 2502 of the present invention to simulate surgical screws adapted to hold the rods 2420. The pegs generally include a body 2448 and a head 2444.

The body 2448 has a size and shape to be engaged by a bore 2408 of the model 2402 or a holder 2508 of the template 2502. In one embodiment, the body 2448 has a size selected to frictionally engage the interior surface of a bore 2408 or a holder 2508 to retain the peg in a selected orientation with respect to the model 2402 or the template 2502. In another embodiment, the shape of the body 2448 is selected to prevent unintended rotation or movement of the peg in relation to the model 2402 or the template 2502. In one embodiment, the cross-sectional shape of the body is one of round, triangular, and square.

The head 2444 is adapted to receive a rod 2420. In one embodiment, the head includes a receiver or recess 2446 adapted to releasably interconnect the rod 2420 to the peg. In one embodiment, the recess 2446 has a generally U-shaped cross-section. However, it will be appreciated by one of skill in the art that the recess may have any other cross-sectional configuration, including, for example, V-shaped, W-shaped, polygonal-shaped, or tapered.

The head 2444 may be stationary or movably interconnected to the body 2448. For example, in one embodiment, the peg 2440A includes a head and body that are formed as one integral piece.

In another embodiment, the peg 2440B includes a head 2444 and body 2448 that are formed separately. The head and body may be joined by suitable techniques known in the art. In one embodiment, the pegs 2440B include an extension 2550 of the head 2444 for insertion into complementary receiver 2552 of the body 2448. Alternatively, one or more tabs may be formed on one of the head or the body and complementary slots on the other of the head and body for receiving the tabs. Bodies 2448 of a variety of lengths may interchangeably be used with the head to adjust the length of the peg 2440B. Further, the orientation of the recess 2446 may be modified by rotating one of the head and the body.

In yet another embodiment, the peg 2440C includes a head 2444 pivotally interconnected to the body 2448. Further, the head 2444 can be moved around one or more axis with respect to the body. Accordingly, the head may be capable of monoaxial or polyaxial movement.

The pegs may be made of any desired material, including plastic, metal, and wood and combinations thereof. In one embodiment, a peg 2440 is manufactured by a 3D printing process. In another embodiment, a peg 2440 is machined.

Referring now to FIGS. 37A-37B, an embodiment of a template 2602 of a surgical tool, instrument or device is provided. The template 2602 may be customized or contoured as described above in conjunction with FIG. 2 to conform to a specific patient's anatomy. In certain embodiments, the template 2602 may provide a surgeon with a particular dimension, shape, orientation, etc. for a device such as a rod 2420.

A map or plan of the locations and orientations of fixation devices that are planned to be used in a surgical procedure is created, as described above. The map includes planned screw trajectories in relation to a specific portion of the patient's anatomy. Patient specific bone models, the same as or similar to model 2402, may be used to create the screw map. Optionally, in another embodiment of the present invention, a template 2502 and pegs 2440 may be used to create the screw map. In another embodiment, the screw map is created using a CAD program or other planning tool.

The map plan is used to create a patient-specific rod. In one embodiment, the rod 2420 is machined using the screw map. In another embodiment, the CAD program uses the screw map to model the rod by connecting each individual planned screw head. This generates a digital model of a rod that will fit into the planned screw locations. The CAD program can then create a template 2602 that includes a negative 2608 of the rod. In one embodiment, the shape of the negative 2608 does not include correction of the deformity of the patient. In another embodiment, the shape of the negative 2608 includes at least some correction of the patient's deformity.

The template 2602 and the negative are manufactured using any suitable manufacturing method. In one embodiment, the template is manufactured using any 3D printing system as described above or developed in the future.

The surgeon may use this negative template 2602 to manually generate three-dimensional patient-specific contours in a generic rod 2420. Once the rod fits in the negative 2608 of the template, it will fit with the planned screw trajectories. Additional correction can be added by the surgeon as necessary or desired. Alternatively, a patient specific rod may be formed with contours that substantially fit in the negative 2608 without additional shaping by the surgeon. The surgeon may then bend the patient-specific rod to alter the shape of the rod. For example, the surgeon may add additional correction to the rod, or change the amount of correction in the rod to correct the patient's deformity.

The template 2602 may optionally include indicia to indicate a position of use, portions of the patient's anatomy, direction, orientation, or the purpose of the rod. The embodiment of the template illustrated in FIG. 37 includes indicia to indicate an alignment of the template. In one embodiment, indicia 2610A indicates a posterior direction and an anterior direction. The template may also include indicia 2610B to identify portions of the patient's anatomy, such as a level of the patient's spine. For example, indicia 2610B is associated with the L5 vertebrae and indicia 2610C is associated with the T3 vertebrae. As will be appreciated by one of skill in the art, any number and type of indicia can be provided associated with different portions of the patient's anatomy.

Referring now to FIGS. 38A-38B, an example of a rod 2420 formed according to one embodiment of the present invention is illustrated in relation to a patient's spine. The screws used to interconnect the rod to the patient's spine have been removed for clarity. After the rod is shaped as described above, the surgeon may further adjust the shape of the rod during a surgical procedure.

Referring now to FIG. 39, an embodiment of a method 2704 of configuring a rod 2420 for use in a surgical procedure is illustrated. A general order for the steps of the method 2704 is shown in FIG. 39. The method 2704 can include more or fewer steps or can arrange the order of the steps differently than those shown in FIG. 39. Hereinafter, the method 2704 shall be explained with reference to the embodiments of the present invention described above in conjunction with FIGS. 34-38.

Generally, the method 2704 starts 2708 by obtaining data of the patient's anatomy. The data can be obtained from one or more of a radiographic imaging machine, a fluoroscopy, an ultrasonic machine, or a nuclear medicine scanning device. Once captured, the data is converted into a digital model at step 2712. The digital model can be produced using known software tools and used in a CAD program. At step 2716, the size, location and orientation of fixtures, such as screws, is planned using the digital model. Optionally, at step 2720, a model 2402, a configurable template 2502, or template 2602 with a rod negative may be produced as described above in conjunction with FIGS. 34-37.

A rod 2420 is produced at step 2724. The rod may be a patient-specific rod with pre-formed bends or contours produced using the planned screw placement. Alternatively, a patient-specific rod can be produced using additional data obtained using one of the models or templates from step 2720. The rod may also be a generic rod without a patient specific shape. Optionally, in step 2728, a generic rod 2420 may be reshaped to fit the model 2402, configurable template 2502, or negative template 2602.

At step 2732 the surgeon determines if additional shaping or correction of the rod is necessary. For example, the surgeon may use one or more of the model 2402 or templates 2502-2602 to adjust the shape of either a pre-formed patient-specific rod or a generic rod. The shape may be adjusted to change the amount of correction of the patient's deformity provided by the rod, to avoid a portion of the patient's anatomy, or due to the surgeon's preferred correction or technique. If additional correction is necessary or desired, the method proceeds YES to step 2736 and the rod is reshaped. If no additional correction is necessary or required, the method proceeds NO to step 2740 and the rod ready for use in a surgical procedure. Optionally, at step 2744, the rod may be used in a surgical procedure.

Referring now to FIGS. 40A-B, yet another patient-specific guide 2810 of an embodiment of the present invention is illustrated. The guide 2810 is similar to guide 1810 described above and comprises similar features. In one embodiment, guide 2810 comprises a medial body 2812 and at least one cannulae 2816.

The guide may comprise individual pieces adapted to be assembled by a surgeon before, or during, a surgical procedure. Accordingly, in one embodiment, the medial body 2812 is formed as two separate portions 2812A, 2812B. The portions 2812A, 2812B may be individually positioned in contact with a predetermined feature of the patient's anatomy. Further, the portions are adapted to be interconnected at joint 2815 in a manner similar to guide 1910 described above. In one embodiment, one portion of the medial body 2812 includes a coupling adapted to releasably interconnect the individual portions 2812A, 2812B of the guide 2810 together. The coupling may be the same as, or similar to, coupling 1913. Accordingly, in one embodiment, the two portions 2812A, 2812B of the guide may be interconnected by positioning the coupling in a corresponding void in the other portion of the medial body. The coupling may be held in the void by friction. Additionally or alternatively, a biasing force may be provided to retain the coupling in the void. In one embodiment, the coupling and void comprise a snap. In another embodiment, the medial body may include magnets. Optionally, in still another embodiment, the medial body portions 2812A, 2812B may be interconnected by a flexible or expandable member, such as a hinge or a biasing member of any type, including a spring. It will be appreciated by one of skill in the art that the medial body portions 2812A, 2812B may be interconnected by any other suitable means. Optionally, in another embodiment of the present invention, the guide 2810 is formed as one integral piece.

The guide 2810 may include features adapted to be grasped or manipulated by a surgeon. In one embodiment, protrusions 2829 are formed on a portion of the guide 2810. The protrusions may be of any shape or size selected facilitate grasping of the guide in a surgical environment. In one embodiment, the protrusions 2829 are formed on a portion of the medial body 2812. The protrusions may comprise ridges or bumps. In one embodiment, the protrusions comprise three generally parallel ridges formed on opposing sides of each portion 2812A, 2812B of the medial body.

The cannula 2816 is the same as, or similar to, the cannulae 1816 described above in conjunction with FIGS. 27-28. In one embodiment, the guide 2810 comprises two cannulae 2816. However, it will be appreciated that the guide may include any number of cannulae. Each cannulae 2816 may have a generally cylindrical shape. Other shapes of the cannulae are contemplated. The cannulae 2816 are configured to contact one or more of the patient's lamina, pars, and aspects of the transverse process and the superior articular process or other portions of the patient's anatomy. Further, the cannulae may be of any length based at least in part on the specific patient's anatomical features, preferences of the surgeon, orientation of the guide 2810, and the type of tool or fixation device associated with the cannulae 2816.

At least one of the cannulae 2816 may include a bore 2820 similar to bore 1820. The bore 2820 comprises a predetermined internal diameter that is adapted to receive a particular instrument or fixation device. The internal diameter may also be selected to prevent the use of the incorrect instrument or device. The bore diameter may also prevent the instrument or device from advancing into the cannulae 2816 beyond a predetermined distance, thereby providing a hard stop. Additionally, the bore 2820 may have a shape adapted to align the tool or fixation device in a predetermined orientation of use. Thus, the cannulae may be adapted to prevent the instrument or fixation device from advancing too far into the boney anatomy of the patient or otherwise being misused. For example, in one embodiment of the present invention, the bore 2820 of the cannulae 2816 may facilitate and guide a drill bit or any other suitable instrument to drill and tap a pilot hole in the cortical trajectory. After the pilot hole is created, the bore 2820 may further guide insertion of a fixation device, such as a cortical screw, into the pilot hole. In another embodiment of the present invention, the bore 2820 may be adapted to receive one or more inserts 1854 or guide wires in a manner similar to that illustrated and described in conjunction with FIGS. 27-28, above.

In one embodiment, the bore 2820 is oriented in a cortical bone trajectory. In another embodiment comprising a bore 2820 in each of the cannulae 2816, the bores may be oriented to target different portions of the patient's anatomy. In still another embodiment, each bore 2820 of two or more cannulae is oriented in a cortical bone trajectory.

The cannulae 2816 may optionally include extensions 2819. The extensions are adapted to wrap at least partially around a predetermined portion of the patient's anatomy. In one embodiment, the extensions 2819 are adapted to wrap at least partially around one of the pars and the superior articular process. The extensions may have any size or shape. In one embodiment, the extensions 2819 are positioned proximate to a distal end of the cannulae 2816. In another embodiment, the extensions 2819 have a shape that wraps around a portion of the exterior of the cannulae. The extensions 2819 may also project at least partially beyond the distal end of the cannulae.

The guide 2810 may take on other shapes, orientations, thicknesses, etc. without deviating from the novel aspects of this disclosure. For example, the guide 2810 may include one or more legs 2824 similar to legs 1824. The legs may extend from one or more of the medial body 2812 and the cannulae 2816.

Additionally or alternatively, patient-specific contact surfaces may be formed on any patient-contacting surfaces 2818 of the cannulae 2816, including the extensions 2819, the legs 2814, and/or the contacting surfaces 2826 of the medial body 2812. The surfaces 2818, 2826 provide a plurality of patient-specific contours for matching with a plurality of anatomical features, as described in greater detail above. The surfaces 2826 of the medial body 2812 may contact at least a portion of the spinous process.

The surfaces 2818 of the cannulae 2816 and the surfaces 2818 of the extensions 2819 and legs 2824 (when present) are adapted to contact or protrude around one or more of, but not limited to, the group comprising: the medial side of the inferior articular process, the lateral sides of the lamina, the spinous process, and the junction between the pars and the transverse process, and other anatomical features of the patient. These patient-contacting surfaces 2818, 2826 help position the guide 2810 and keep it in position in a predetermined position and orientation.

Although not illustrated in FIG. 40, the guide 2810 may further comprise slots formed in the medial body 2812 or the cannulae 2816. The slots may be the same as or similar to slots 1830. In one embodiment, the slots are adapted to direct the path of a blade or other cutting instrument in a manner similar to cutting slots 20-820 of all embodiments described above. Alternatively, the slots of guide 2810 may be adapted to receive one or more secondary 2840 or tertiary cannulae 2850 as further described in conjunction with FIG. 33. In another embodiment, the guide 2810 is adapted to receive a cutting guide 10 in a manner similar to guide 1810A illustrated in FIG. 27D. The cutting guide 10 may be received by a slot formed in one or more of the medial body, cannulae, and legs. Optionally, the cutting guide 10 may be integrally formed with the guide 2810.

Although the devices described above have been illustrated for use with certain guide screws and/or instruments, it is expressly understood that the devices may be used with a variety of other implantable and non-implantable apparatus, including by way of example, medial-to-laterally placed transpedicular screws (commonly referred to as cortical bone trajectory screws). Other screws and instruments may be used with the surgical devices described above without departing from the spirit of the disclosure, and are considered to be within the scope of the appended claims.

With respect to the embodiments described above, it is expressly understood that such embodiments may be incorporated for use in practicing the novel methods described herein. In certain embodiments, those methods may comprise greater or fewer steps than as described above. By way of example, but not limitation, one step for use with the various embodiments described above may comprise the use of various technologies for capturing a patient's unique morphology, and subsequently mapping and/or planning the fabrication of a device comprising one or more "patient matched" surfaces or features for complementing that unique morphology. Further, such devices may be further optimized with respect to the unique data associated with the patient, such that the device may be matched with specific devices for use during the surgical procedure, or oriented around the patient's own anatomy to achieve, for example, one or more desired insertional trajectories (which may be verified in a pre-operative setting). Variations on this step, and the inclusion or exclusion of additional steps described herein are expressly contemplated by the present disclosure.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A patient-specific guide for use in a surgical procedure, comprising:
    a medial body having a proximal portion and a distal portion;
    a first cannula and a second cannula, each of the cannulae with proximal and distal portions, at least one of the first cannula and the second cannula further comprising a bore oriented in a direction determined from the anatomical features of a patient, the bore adapted to guide an instrument or a fixation device in a cortical bone trajectory; and
    a surface of one or more of the medial body, the first cannula, and the second cannula including patient-specific contours determined from the patient's anatomy and configured to contact and substantially conform to at least a first subcutaneous anatomic feature of a vertebra of the patient.

2. The patient-specific guide of claim 1, further comprising a leg extending from at least one of the first and second cannulae, the leg including a second surface including patient-specific contours determined from the patient's anatomy and configured to contact and substantially conform to a second anatomic feature of the patient.

3. The patient-specific guide of claim 1, further comprising at least one leg extending from the medial body, the at least one leg including a second surface including patient-specific contours determined from the patient's anatomy and configured to contact and substantially conform to a second anatomic feature of the patient.

4. The patient-specific guide of claim 1, wherein the surface with the patient-specific contours is adapted to hook at least partially around vertebral anatomy selected from the group consisting of: a lamina, a pars interarticularis, an aspect of a transverse process, a spinous process, an inferior articular process, and a superior articular process.

5. The patient-specific guide of claim 1, wherein the medial body comprises a first portion releasably interconnected to a second portion.

6. The patient-specific guide of claim 1, further comprising at least a third cannula having a bore that is oriented in a direction determined from the anatomical features of the patient, the bore adapted to guide an instrument or a fixation device.

7. The patient-specific guide of claim 6, wherein the direction of the bore of the third cannula is not parallel to the bore of the at least one of the first and second cannula.

8. The patient-specific guide of claim 6, wherein the third cannula is releasably interconnected to the guide.

9. The patient-specific guide of claim 1, further comprising a cutting guide interconnected to a portion of the guide, the cutting guide including a track having patient-specific depth control, angle, and orientation adapted to guide an instrument operable to remove a predetermined portion of the vertebrae.

10. A patient-specific guide for use in a surgical procedure, the guide adapted to contact a predetermined portion of a vertebra of a patient, comprising:
    a body with a proximal portion and a distal portion, the body having at least one of a bore and a track oriented in a predetermined trajectory determined from anatomical features of the patient, the bore or track adapted to guide an instrument or a fixation device in one of a cortical bone trajectory, a pedicle screw trajectory, a cortical trajectory, a sacral pedicle trajectory, a sacral alar trajectory and an S2-alar-iliac trajectory; and
    at least two legs extending from the body, a portion of each leg comprising patient-specific contours determined from the patient's anatomy and configured to contact and substantially conform to at least a first subcutaneous anatomic feature of the vertebra of the patient.

11. The patient-specific guide of claim 10, wherein at least a portion of one of the legs is adapted to hook at least partially around, and substantially conform to, a second anatomic feature of the patient.

12. The patient-specific guide of claim 10, further comprising a frame, the frame configured to be fixed to screws placed in at least one vertebrae of the patient, wherein the body of the guide is adapted to interconnect to the frame.

13. The patient-specific guide of claim 10, wherein the track has patient-specific depth control, angle, and orientation adapted to guide an instrument operable to remove a predetermined portion of the vertebrae.

14. The patient-specific guide of claim 13, further comprising a second track formed in the body.

15. The patient-specific guide of claim 10, the body further comprising a second bore that is oriented in a direction for placement of a temporary fixation device.

16. A patient-specific positioning template for use in a surgical procedure, comprising:
  a body having a proximal portion and a distal portion, the distal portion shaped to substantially conform to a predetermined portion of a vertebrae of a patient, the body having at least one of a bore and a track oriented in a direction determined from anatomical features of the patient, the bore or track adapted to guide an instrument or a fixation device in one of a cortical bone trajectory, a pedicle screw trajectory, a cortical trajectory, a sacral pedicle trajectory, a sacral alar trajectory and an S2-alar-iliac trajectory; and
  an extension of the distal portion of the body configured to hook at least partially around, and substantially conform to, at least a second predetermined portion of the vertebrae of the patient.

17. The patient-specific positioning template of claim 16, wherein the extension of the body is designed to hook at least partially around vertebral anatomy selected from the group consisting of: a lamina, a pars interarticularis, an aspect of a transverse process, a spinous process, an inferior articular process, and a superior articular process.

18. The patient-specific positioning template of claim 16, wherein the track has patient-specific depth control, angle, and orientation adapted to guide an instrument operable to remove a predetermined portion of the vertebrae.

19. The patient-specific positioning template of claim 18, further comprising a second track formed in the body.

20. The patient-specific positioning template of claim 16, further comprising a cannula with a second bore that is oriented in a direction for placement of a temporary fixation device.

21. The patient-specific positioning template of claim 16, wherein the distal portion of the body of the template is shaped to substantially conform to cut surfaces generated by removal of a portion of the patient's vertebrae.

22. The patient-specific positioning template of claim 16, further comprising a frame, the frame configured to be fixed to screws placed in at least one vertebrae of the patient, wherein the body of the template is adapted to interconnect to the frame.

* * * * *